United States Patent

Ueno et al.

[11] Patent Number: 5,594,016
[45] Date of Patent: Jan. 14, 1997

[54] NAPHTHALENE DERIVATIVES

[75] Inventors: Hiroaki Ueno, Tokyo-to; Takayuki Oe, Yokohama; Ichiro Suehiro, Machida; Fumiko Nakamura, Tsukuba, all of Japan

[73] Assignee: Mitsubishi Chemical Corporation, Tokyo, Japan

[21] Appl. No.: 546,732

[22] Filed: Oct. 23, 1995

Related U.S. Application Data

[63] Continuation-in-part of Ser. No. 171,709, Dec. 22, 1993, abandoned.

[30] Foreign Application Priority Data

Dec. 28, 1992 [JP] Japan ................... 4-349172

[51] Int. Cl.$^6$ .................................. A61K 31/425
[52] U.S. Cl. ..................... 514/369; 514/320; 514/381; 548/184; 548/185; 548/191; 548/252; 548/253
[58] Field of Search .......................... 514/369, 381, 514/320; 548/184, 185, 191, 252, 253

[56] References Cited

U.S. PATENT DOCUMENTS

| | | | |
|---|---|---|---|
| 4,572,912 | 2/1986 | Yoshioka et al. | 548/184 |
| 4,868,193 | 9/1989 | Lee | 548/252 |
| 4,873,255 | 10/1989 | Yoshioka et al. | 548/183 |
| 5,037,842 | 8/1991 | Goldstein | 548/183 |
| 5,132,317 | 7/1992 | Cantello et al. | 548/183 |
| 5,260,445 | 11/1993 | Hindley | 548/183 |

FOREIGN PATENT DOCUMENTS

| | | | |
|---|---|---|---|
| 0155845 | 9/1985 | European Pat. Off. | 548/183 |
| 0193256 | 9/1986 | European Pat. Off. | 548/183 |
| 0207581 | 1/1987 | European Pat. Off. | 548/183 |
| 0207605 | 1/1987 | European Pat. Off. | 548/183 |
| 0283035 | 9/1988 | European Pat. Off. | 548/183 |

*Primary Examiner*—James H. Reamer
*Attorney, Agent, or Firm*—Wenderoth, Lind & Ponack

[57] ABSTRACT

Naphthalene derivatives represented by the formula (I):

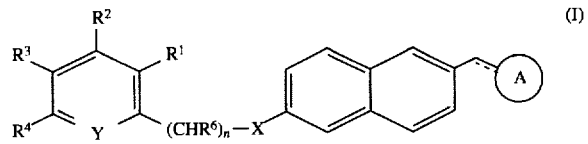

wherein the symbol

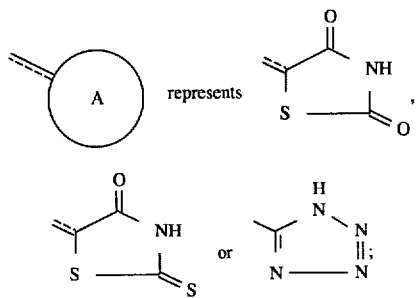

—X— represents —O— or —S—,
=Y— represents =N— or =CR$^5$—, R$^1$, C$^2$, R$^3$, R$^4$ and R$^5$ represent hydrogen, halogen, alkyl and the like,
R$^6$ represents hydrogen, alkyl, aryl and the like,
n represents an integer of 0 to 3, --- represents a single bond or a double bond, which are useful for reducing blood sugar and blood lipid levels are provided.

7 Claims, No Drawings

NAPHTHALENE DERIVATIVES

This application is a continuation-in-part of now abandoned application, Ser. No. 08/171,709, filed Dec. 22, 1993.

BACKGROUND OF THE INVENTION

The present invention relates to novel naphthalene derivatives. In particular, it relates to novel naphthalene derivatives useful for reducing blood sugar and blood lipid levels.

Diabetes is a compound disease caused by hyperglycemia which results from dysfunction of insulin which reduces blood sugar level. Diabetes can be classified into several types based on etiology. Among others, two types of diabetes are most important, one of which is insulin-dependent diabetes mellitus (type I diabetes) which is caused by insulin deficiency and requires insulin supply for the treatment of the disease, and noninsulin-dependent diabetes mellitus (type II diabetes) which is caused by abnormalities of insulin receptors or sugar transporting carriers in spite of sufficient production of insulin.

At present, the treatment of noninsulin-dependent diabetes mellitus is mainly carried out by a combination of ergotherapy, alimentary therapy, and oral administration of anti-hyperglycemic agents, and for more severe conditions, insulin preparations are used. As anti-hyperglycemic agents for oral administration there are used sulfonylureas (for example, tolbutamide, acetohexamide, tolazamide, glibenclamide, etc.) and biguanides. However, biguanides are scarcely used because of their side effects such as lactic acidosis and the like. On the other hand, sulfonylureas show potent anti-hyperglycemic activity but can sometimes induce hypoglycemia. Accordingly, sulfonylureas must be used very carefully. In addition, a phenomenon knows as "secondary failure" is seen during the use of sulfonylureas for a long period of time, which means gradual decrease of effectiveness.

Although a variety of new anti-hyperglycemic agents having less side effects than sulfonylureas have been currently developed, most of them have not been put into practical use due to their insufficient activities and side effects.

In recent years, insulin-resistance ameriolating agents have attracted the attention of people concerned, which reduce blood sugar level by ameriolating insulin-resistance in peripheral tissues, which is one of the causes of noninsulin-dependent diabetes mellitus. However, conventional insulin-resistance ameriolating agents are unsatisfactory because of their insufficient desirable effect and undersirable side effects, and it has long been desired to develop new agents which have more powerful effect and less side effects.

Japanese patent publication (Kokai) No. 48471/1984 discloses thiazolidine derivatives which reduce blood sugar and triglyceride levels in blood plasma. The derivatives are represented by the following formula:

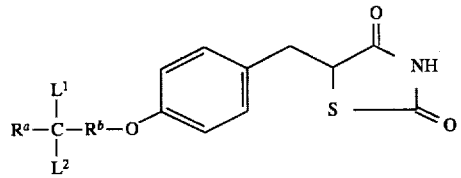

wherein each of $L^1$ and $L^2$ is defined as hydrogen when $R^a$ is a suitably substituted phenyl, and $R^b$ is a bond or a lower alkylene.

Japanese patent publication (Kokai) No. 267580/1988 discloses thiazolidinedione derivatives having an ability of reducing blood sugar and blood lipid levels, which are represented by the following formula:

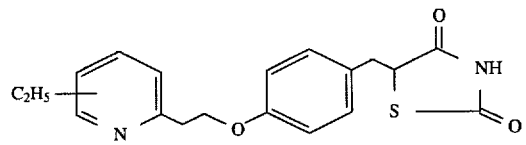

Further, U.S. Pat. No. 4,703,052 describes thiazolidinedione derivatives having an ability of reducing blood sugar and blood lipid levels, which are represented by the following formula:

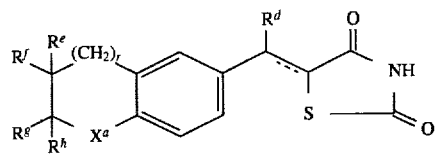

wherein the dotted line is an arbitrary bond; $R^c$ is hydrogen, methyl or ethyl; $X^a$ is O, S, SO, $SO_2$, $CH_2$, CO, CHOH or $NH^h$ ($R^h$ is hydrogen) or acyl group; $R^d$, $R^e$ $R^f$ are hydrogen or methyl; and $R^g$ is a substituted phenyl, benzyl, phenethyl or styryl.

British patent No. 8713861 discloses thiazolidinedione derivatives having an ability of reducing blood sugar and blood lipid levels, which are represented by the following formula:

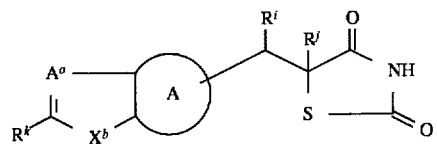

wherein $A^o$ represents nitrogen or $R^l$—C(=)— moietry, $R^k$ represents $R^l$—$Y^a$—Z wherein $R^l$ represents a substituted or a unsubstituted phenyl, pyridyl or oxazolyl group, $Y^a$ represents —$(CH_2)n^a$— ($n^a$ stands for an integer of 0 to 6) and Z represents —$CH_2$—, —CH(OH)— or —CO—; each of $R^i$ and $R^j$ represents hydrogen or $R^i$ and $R^j$ combine together to form a bond; A represents a residue of a benzene ring; and $X^b$ represents O or S).

Further, Japanese patent publication (Kokai) No. 56675/1989 discloses thiazolidinedione derivatives having an ability of reducing blood sugar level, which are represented by the following formula:

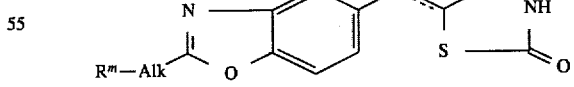

wherein $R^m$ represents phenyl, naphthyl, cycloalkyl or heterocycle, all of which may be substituted; Alk represents a single bond, lower alkenylene, lower alkynylene, or lower alkylene which may be substituted; and the dotted line represents a bond which may be a double bond.

As described above, among thiazolidinedione derivatives having an ability of reducing blood sugar and blood lipid lebels, and which have been disclosed so far, there has been no compound wherein the aromatic ring moiety to which 5-(2,4-thiazolidinedione)-methyl group or 5-(2,4-thiazolidinedione)-methylene group is attached has a naphthalene structure.

On the other hand, U.S. Pat. No. 4,997,948 issued to Zask et al. discloses naphthalenylsulfonyl thiazolidinedione derivatives having an ability of reducing blood sugar level, which are represented by the following formula:

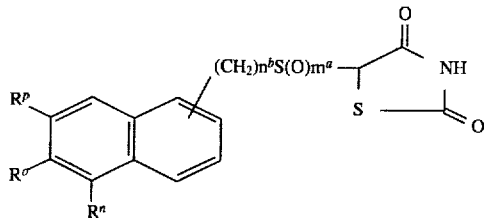

wherein $R^n$ represents hydrogen, bromine, chlorine, trifluoromethyl or difluoroethyl; $R^o$ represents hydrogen, hydroxyl, methoxyl or ethoxyl when $R^p$ represents hydrogen, or both $R^o$ and $R^p$ represent methoxycarbonyloxyl or ethoxycarbonyloxyl; $m^a$ represent 0 or 2; and $n^b$ represents 0 or 1. However, their effect of reducing blood sugar can not be said to be sufficient.

Further, Zask et al., J. Med. Chem., 33 (5): 1418–1423 (1990) discloses thiasolidine derivatives showing the effect of reducing blood sugar level, which are represented by the following formula:

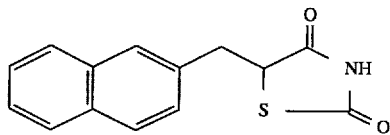

but such compounds can not be said to have sufficient effect on reducing blood sugar level.

Keath et al., J. Med. Chem., 32 (1): 11–13 (1989) discloses tetrazole derivatives showing an effect of reducing blood sugar level, which are represents by the following formula:

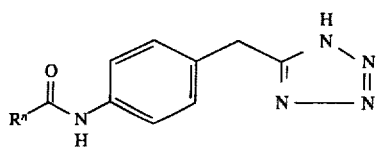

wherein $R^n$ represents $C_1$–$C_{10}$ perfluoroalkyl.

European patent publication No. 393941 discloses naphthalenylalkyl-3H-1,2,3,5-oxathiadiazole-2-oxides showing the blood sugar level reducing effect, which are represented by the following formula:

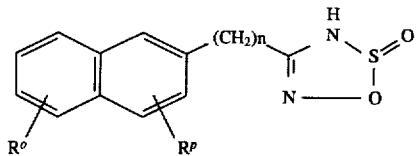

wherein $R^o$ and $R^p$ represent independently hydrogen, lower alkyl having 1 to 6 carbon atoms, lower alkoxyl having 1 to 6 carbon atoms, halogen, ethynyl, nitrile, methylthio, trifluoromethyl, vinyl, nitro or halogen-substituted benzyloxyl; and n represents 0 to 4.

Further, European patent publication No. 343643 discloses a compound represented by the following formula:

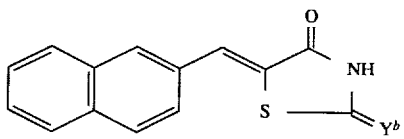

wherein $Y^b$ represents an oxygen atom or sulfur atom, which are compounds having a structure similar to that of the compounds of the present invention. They are different from the compounds of the present invention in the substituents attached to the naphthalene ring. In addition, the above publication describes that the object is to use the compounds for treatment of allergy or inflammation and it refers to nothing for the reduction of the blood sugar and blood lipid levels, which is the object of the present invention.

SUMMARY OF THE INVENTION

The subject matter of the present invention is to provide novel naphthalene derivatives exhibiting an excellent effect on reducing blood sugar and blood lipid levels.

The inventors of the present invention synthesized various compounds and evaluated their effect on reducing blood sugar and blood lipid levels. Consequently, it was found that novel naphthalene derivatives represented by the general formula I are excellent in said effect. The present invention has been accomplished based on such finding.

Namely, the gist of the present invention exists in providing naphthalene derivatives represented by the following formula (I):

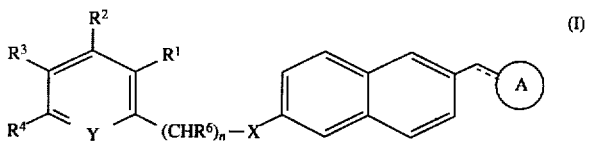

wherein the symbol

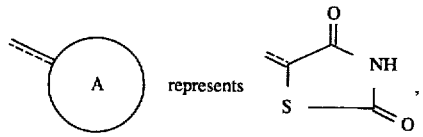 represents 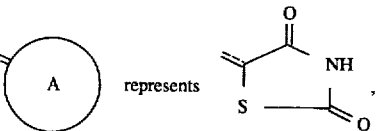,

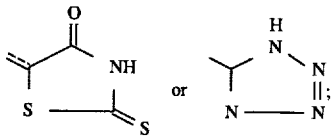

—X— represents —O— or —S—; =Y— represents =N— or =CR$^5$—; each of $R^1$, $R^2$, $R^3$, $R^4$ and $R^5$ represents independently hydrogen, halogen, alkyl, aryl, alkoxy, alkoxyalkoxy, aryloxy, alkanoyloxy, arylcarbonyloxy, carboxy, alkoxycarbonyl, aryloxycarbonyl, carbamoyl, alkylaminocarbonyl, arylaminocarbonyl, amino, alkylamino, alkanoylamino, arylcarbonylamino, ethylenedioxymethyl, formyl, cyano, nitro or trihalomethyl; $R^6$ represents hydrogen, alkyl which may be substituted or aryl which may be substituted; n represents an integer of 0 to 3; and the dotted and solid lines show that the bond may be a single or double bond; or a pharmaceutically acceptable salt thereof.

DETAILED DESCRIPTION OF THE INVENTION

The present invention is described in detailed below. The compound of the present invention is a naphthalene derivatives represented by the following general formula (I):

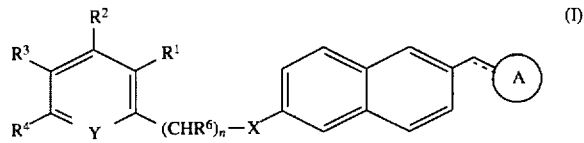

wherein the symbol

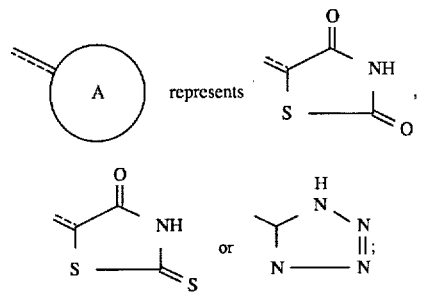

—X— represents —O— or —S—;
=Y— represents =N— or =CR$^5$—; each of R$^1$, R$^2$, R$^3$, R$^4$ and R$^5$ represents independently hydrogen, halogen (fluorine, chlorine, bromine, iodine, etc.), C$_1$–C$_8$ alkyl (methyl, butyl, octyl, etc.), C$_6$ · C$_{12}$ aryl (phenyl, naphthyl, etc.), C$_1$–C$_8$ alkoxy (methoxy, butoxy, octyloxy, etc.), C$_2$–C$_6$ alkoxyalkoxy (methoxymethoxy, methoxyethoxy, ethoxyethoxy, methoxypentoxy, etc.), C$_6$–C$_{12}$ aryloxy (phenyloxy, naphthyloxy, etc.), C$_2$–C$_9$ alkanoyloxy (acetoxy, valeryloxy, hexanoyloxy, etc.), C$_7$–C$_{13}$ arylcarbonyloxy (benzoyloxy, naphthylcarbonyloxy, etc.), carboxy, C$_2$–C$_9$ alkoxycarbonyl (methoxycarbonyl, butyloxycarbonyl, octyloxycarbonyl, etc.), C$_7$–C$_{13}$ aryloxycarbonyl (phenyloxycarbonyl, naphthyloxycarbonyl, etc.), carbamoyl, C$_2$–C$_9$ alkylaminocarbonyl (methylaminocarbonyl, butylaminocarbonyl, octylaminocarbonyl, dimethylaminocarbonyl, dibutylaminocarbonyl, etc.), C$_7$–C$_{13}$ arylaminocarbonyl (phenylaminocarbonyl, naphthylaminocarbonyl, etc.), amino, C$_1$–C$_8$ alkylamino (methylamino, butylamino, octylamino, dimethylamino, dibutylamino, etc.), C$_2$–C$_9$ alkanoylamino (acetylamino, valerylamino, hexanoylamino, etc.), C$_7$–C$_{13}$ arylcarbonylamino (benzoylamino, naphthylcarbonylamino, etc.), ethylenedioxymethyl, formyl, cyano, nitro or trihalomethyl (trifluoromethyl, trichloromethyl, tribromomethyl, triiodomethyl, etc.);

R$^6$ represents hydrogen, C$_1$–C$_8$ alkyl (methyl, butyl, octyl, etc.) which may be substituted by one or more substituents selected from the group consisting of phenyl, halogen (fluorine, chlorine, bromine, iodine, etc.), nitro and cyano, or C$_6$–C$_{12}$ aryl (phenyl, naphthyl, etc.) which may be substitued by one or more substituents selected from the group consisting of C$_1$–C$_8$ alkyl (methyl, butyl, octyl, etc.), halogen (fluorine, chlorine, iodine, etc.), nitro and cyano; n represents an integer of 0 to 3; and the dotted line shows that the bond at the corresponding position may be a double bond; or a pharmaceutically acceptable salt thereof.

Preferred compounds in the present invention include a compound represented by formula (I) wherein each of R$^1$, R$^2$, R$^3$, R$^4$ and R$^5$ represents independently hydrogen, halogen, C$_1$–C$_8$ alkyl, C$_1$–C$_8$ alkoxy, C$_2$–C$_6$ alkoxyalkoxy, C$_2$–C$_9$ alkanoyloxy, C$_7$–C$_{13}$ arylcarbonyloxy, carboxy, C$_2$–C$_9$ alkoxycarbony, carbamoyl, C$_2$–C$_9$ alkylaminocarbonyl, C$_7$–C$_{13}$ arylaminocarbonyl, amino, C$_1$–C$_8$ alkylamino, C$_2$–C$_9$ alkanoylamino, C$_7$–C$_{13}$ arylcarbonylamino, ethylenedioxymethyl, formyl, cyano, nitro or trihalomethyl;

R$^6$ represents hydrogen, C$_1$–C$_8$ alkyl, or C$_6$–C$_{12}$ aryl which may be substituted by halogen.

Especially preferred compounds of the present invention include a compound represented by formula (I) wherein —X— represents —O—; =Y— represents =CR$^5$—; each of R$^1$, R$^2$, R$^3$, R$^4$ and R$^5$ represents independently hydrogen, halogen, C$_1$–C$_5$ alkyl, C$_1$–C$_5$ alkoxy, C$_2$–C$_6$ alkoxyalkoxy, C$_2$–C$_6$ alkanoyloxy, carboxy, C$_2$–C$_6$ alkoxycarbonyl, C$_7$–C$_{13}$ arylaminocarbonyl, amino, C$_2$–C$_6$ alkanoylamino, ethylenedioxymethyl, formyl, cyano, nitro or trihalomethyl; R$^6$ represents hydrogen, C$_1$–C$_5$ alkyl or C$_6$–C$_{12}$ aryl which may be substituted by halogen.

Further, most preferable compounds of the present invention include a compound represented by the formula (I) wherein the symbol

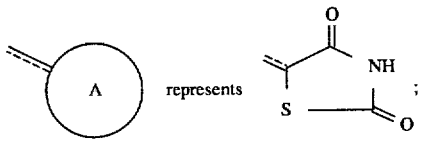

—X— represents —O—; =Y— represents =CR$^5$—; each of R$^1$, R$^2$, R$^3$ and R$^4$ represents independently hydrogen or halogen; R$^5$ represents hydrogen; R$^6$ represents hydrogen; n represents 1; and the bond represented by the dotted and solid lines is a single bond.

Salts with a naphthalene derivatives represented by the above formula (I) include salts with the non-toxic bases, and preferable salts include salts with inorganic bases such as sodium salts, potassium salts and the like, and salts with organic bases such as ammonium salts, trimethylamine salts.

The present invention includes compounds which contain an asymmetric carbon atom. In this case, the present invention also includes the isolated stereoisomers and the mixture of the stereoisomers.

The particular examples of the compounds of the present invention are shown in Tables 1, 2, 3 and 4.

The compounds in Table 1 (compound Nos. 8–614) are represented by the following formula (I-a):

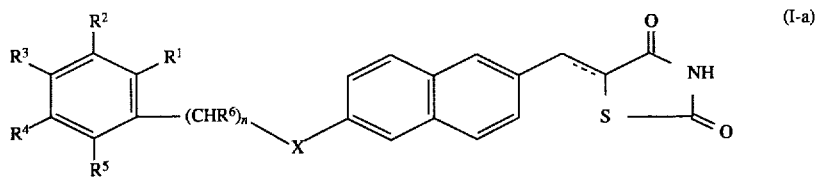

The compounds in Table 2 (compound Nos. 615–718) are represented by the following formula (I-b):

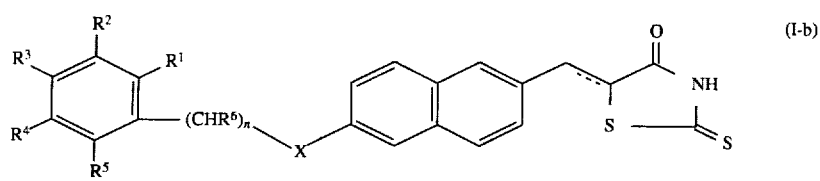
(I-b)

The compounds in Table 3 (compound Nos. 719–770) are represented by the following formula (I-c):

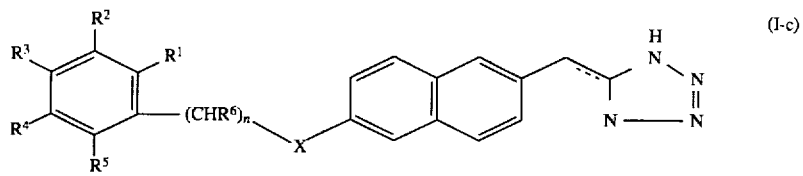
(I-c)

The compounds in Table 4 (compound Nos. 771–822) are represented by the following formula (I-d):

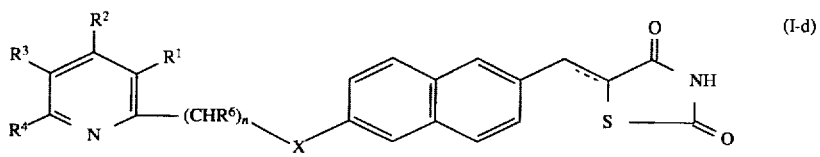
(I-d)

The right hand columns in the tables show the bond represented by the dotted and solid lines is either a single bond or double bond. The letter "n" positioned at the right side of alkyl groups in the tables shows that the corresponding alkyl group is a linear chain.

TABLE 1

| Compound No. | $R^1$ | $R^2$ | $R^3$ | $R^4$ | $R^5$ | $R^6$ | n | X | |
|---|---|---|---|---|---|---|---|---|---|
| 1 | —H | —H | —H | —H | —H | — | 0 | O | |
| 2 | —H | —H | —H | —H | —H | —H | 1 | O | |
| 3 | —H | —H | —H | —H | —H | —H | 2 | O | |
| 4 | —H | —H | —H | —H | —H | —H | 3 | O | |
| 5 | —F | —H | —H | —H | —H | —H | 1 | O | |
| 6 | —H | —F | —H | —H | —H | —H | 1 | O | |
| 7 | —H | —H | —F | —H | —H | —H | 1 | O | |
| 8 | —Cl | —H | —H | —H | —H | —H | 1 | O | |
| 9 | —H | —Cl | —H | —H | —H | —H | 1 | O | |
| 10 | —H | —H | —Cl | —H | —H | —H | 1 | O | A |
| 11 | —Br | —H | —H | —H | —H | —H | 1 | O | single |
| 12 | —H | —Br | —H | —H | —H | —H | 1 | O | bond |
| 13 | —H | —H | —Br | —H | —H | —H | 1 | O | |
| 14 | —I | —H | —H | —H | —H | —H | 1 | O | |
| 15 | —H | —I | —H | —H | —H | —H | 1 | O | |
| 16 | —H | —H | —I | —H | —H | —H | 1 | O | |
| 17 | —CH$_3$ | —H | —H | —H | —H | —H | 1 | O | |
| 18 | —H | —CH$_3$ | —H | —H | —H | —H | 1 | O | |
| 19 | —H | —H | —CH$_3$ | —H | —H | —H | 1 | O | |
| 20 | —C$_2$H$_5$ | —H | —H | —H | —H | —H | 1 | O | |
| 21 | —H | —C$_2$H$_5$ | —H | —H | —H | —H | 1 | O | |
| 22 | —H | —H | —C$_2$H$_5$ | —H | —H | —H | 1 | O | |
| 23 | —C$_3$H$_7$n | —H | —H | —H | —H | —H | 1 | O | |
| 24 | —H | —C$_3$H$_7$n | —H | —H | —H | —H | 1 | O | |
| 25 | —H | —H | —C$_3$H$_7$n | —H | —H | —H | 1 | O | |
| 26 | —CH(CH$_3$)$_2$ | —H | —H | —H | —H | —H | 1 | O | |
| 27 | —H | —CH(CH$_3$)$_2$ | —H | —H | —H | —H | 1 | O | |
| 28 | —H | —H | —CH(CH$_3$)$_2$ | —H | —H | —H | 1 | O | |
| 29 | —C$_4$H$_9$n | —H | —H | —H | —H | —H | 1 | O | |
| 30 | —C$_5$H$_{11}$n | —H | —H | —H | —H | —H | 1 | O | |

TABLE 1-continued

| Compound No. | R¹ | R² | R³ | R⁴ | R⁵ | R⁶ | n | X | 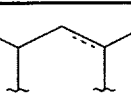 |
|---|---|---|---|---|---|---|---|---|---|
| 31 | $-C_6H_{13}{}^n$ | $-H$ | $-H$ | $-H$ | $-H$ | $-H$ | 1 | O | |
| 32 | $-C_7H_{15}{}^n$ | $-H$ | $-H$ | $-H$ | $-H$ | $-H$ | 1 | O | |
| 33 | $-OCH_3$ | $-H$ | $-H$ | $-H$ | $-H$ | $-H$ | 1 | O | |
| 34 | $-H$ | $-OCH_3$ | $-H$ | $-H$ | $-H$ | $-H$ | 1 | O | |
| 35 | $-H$ | $-H$ | $-OCH_3$ | $-H$ | $-H$ | $-H$ | 1 | O | |
| 36 | $-OC_2H_5$ | $-H$ | $-H$ | $-H$ | $-H$ | $-H$ | 1 | O | A |
| 37 | $-H$ | $-OC_2H_5$ | $-H$ | $-H$ | $-H$ | $-H$ | 1 | O | single |
| 38 | $-H$ | $-H$ | $-OC_2H_5$ | $-H$ | $-H$ | $-H$ | 1 | O | bond |
| 39 | $-OC_3H_7{}^n$ | $-H$ | $-H$ | $-H$ | $-H$ | $-H$ | 1 | O | |
| 40 | $-H$ | $-OC_3H_7{}^n$ | $-H$ | $-H$ | $-H$ | $-H$ | 1 | O | |
| 41 | $-H$ | $-H$ | $-OC_3H_7{}^n$ | $-H$ | $-H$ | $-H$ | 1 | O | |
| 42 | $-OCH(CH_3)_2$ | $-H$ | $-H$ | $-H$ | $-H$ | $-H$ | 1 | O | |
| 43 | $-H$ | $-OCH(CH_3)_2$ | $-H$ | $-H$ | $-H$ | $-H$ | 1 | O | |
| 44 | $-H$ | $-H$ | $-OCH(CH_3)_2$ | $-H$ | $-H$ | $-H$ | 1 | O | |
| 45 | $-OC_4H_9{}^n$ | $-H$ | $-H$ | $-H$ | $-H$ | $-H$ | 1 | O | |
| 46 | $-OC_5H_{11}{}^n$ | $-H$ | $-H$ | $-H$ | $-H$ | $-H$ | 1 | O | |
| 47 | $-OC_6H_{13}{}^n$ | $-H$ | $-H$ | $-H$ | $-H$ | $-H$ | 1 | O | |
| 48 | $-OC_7H_{15}{}^n$ | $-H$ | $-H$ | $-H$ | $-H$ | $-H$ | 1 | O | |
| 49 | $-OCOCH_3$ | $-H$ | $-H$ | $-H$ | $-H$ | $-H$ | 1 | O | |
| 50 | $-H$ | $-OCOCH_3$ | $-H$ | $-H$ | $-H$ | $-H$ | 1 | O | |
| 51 | $-H$ | $-H$ | $-OCOCH_3$ | $-H$ | $-H$ | $-H$ | 1 | O | |
| 52 | $-OCOC_2H_5$ | $-H$ | $-H$ | $-H$ | $-H$ | $-H$ | 1 | O | |
| 53 | $-OCOC_3H_7{}^n$ | $-H$ | $-H$ | $-H$ | $-H$ | $-H$ | 1 | O | |
| 54 | $-OCOCH(CH_3)_2$ | $-H$ | $-H$ | $-H$ | $-H$ | $-H$ | 1 | O | |
| 55 | $-OCOC_4H_9{}^n$ | $-H$ | $-H$ | $-H$ | $-H$ | $-H$ | 1 | O | |
| 56 | $-OCOC_5H_{11}{}^n$ | $-H$ | $-H$ | $-H$ | $-H$ | $-H$ | 1 | O | |
| 57 | $-OCOC_6H_{13}{}^n$ | $-H$ | $-H$ | $-H$ | $-H$ | $-H$ | 1 | O | |
| 58 | $-OCOC_7H_{15}{}^n$ | $-H$ | $-H$ | $-H$ | $-H$ | $-H$ | 1 | O | |
| 59 | $-OCOC_6H_5$ | $-H$ | $-H$ | $-H$ | $-H$ | $-H$ | 1 | O | |
| 60 | $-H$ | $-OCOC_6H_5$ | $-H$ | $-H$ | $-H$ | $-H$ | 1 | O | |
| 61 | $-H$ | $-H$ | $-OCOC_6H_5$ | $-H$ | $-H$ | $-H$ | 1 | O | |
| 62 | $-CN$ | $-H$ | $-H$ | $-H$ | $-H$ | $-H$ | 1 | O | A |
| 63 | $-H$ | $-CN$ | $-H$ | $-H$ | $-H$ | $-H$ | 1 | O | single |
| 64 | $-H$ | $-H$ | $-CN$ | $-H$ | $-H$ | $-H$ | 1 | O | bond |
| 65 | $-NO_2$ | $-H$ | $-H$ | $-H$ | $-H$ | $-H$ | 1 | O | |
| 66 | $-H$ | $-NO_2$ | $-H$ | $-H$ | $-H$ | $-H$ | 1 | O | |
| 67 | $-H$ | $-H$ | $-NO_2$ | $-H$ | $-H$ | $-H$ | 1 | O | |
| 68 | $-COOH$ | $-H$ | $-H$ | $-H$ | $-H$ | $-H$ | 1 | O | |
| 69 | $-H$ | $-COOH$ | $-H$ | $-H$ | $-H$ | $-H$ | 1 | O | |
| 70 | $-H$ | $-H$ | $-COOH$ | $-H$ | $-H$ | $-H$ | 1 | O | |
| 71 | $-COOCH_3$ | $-H$ | $-H$ | $-H$ | $-H$ | $-H$ | 1 | O | |
| 72 | $-H$ | $-COOCH_3$ | $-H$ | $-H$ | $-H$ | $-H$ | 1 | O | |
| 73 | $-H$ | $-H$ | $-COOCH_3$ | $-H$ | $-H$ | $-H$ | 1 | O | |
| 74 | $-COOC_2H_5$ | $-H$ | $-H$ | $-H$ | $-H$ | $-H$ | 1 | O | |
| 75 | $-H$ | $-COOC_2H_5$ | $-H$ | $-H$ | $-H$ | $-H$ | 1 | O | |
| 76 | $-H$ | $-H$ | $-COOC_2H_5$ | $-H$ | $-H$ | $-H$ | 1 | O | |
| 77 | $-COOC_3H_7{}^n$ | $-H$ | $-H$ | $-H$ | $-H$ | $-H$ | 1 | O | |
| 78 | $-H$ | $-COOC_3H_7{}^n$ | $-H$ | $-H$ | $-H$ | $-H$ | 1 | O | |
| 79 | $-H$ | $-H$ | $-COOC_3H_7{}^n$ | $-H$ | $-H$ | $-H$ | 1 | O | |
| 80 | $-COOCH(CH_3)_2$ | $-H$ | $-H$ | $-H$ | $-H$ | $-H$ | 1 | O | |
| 81 | $-H$ | $-COOCH(CH_3)_2$ | $-H$ | $-H$ | $-H$ | $-H$ | 1 | O | |
| 82 | $-H$ | $-H$ | $-COOCH(CH_3)_2$ | $-H$ | $-H$ | $-H$ | 1 | O | |
| 83 | $-COOC_4H_9{}^n$ | $-H$ | $-H$ | $-H$ | $-H$ | $-H$ | 1 | O | |
| 84 | $-COOC_5H_{11}{}^n$ | $-H$ | $-H$ | $-H$ | $-H$ | $-H$ | 1 | O | |
| 85 | $-COOC_6H_{13}{}^n$ | $-H$ | $-H$ | $-H$ | $-H$ | $-H$ | 1 | O | |
| 86 | $-COOC_7H_{15}{}^n$ | $-H$ | $-H$ | $-H$ | $-H$ | $-H$ | 1 | O | |
| 87 | $-CONH_2$ | $-H$ | $-H$ | $-H$ | $-H$ | $-H$ | 1 | O | |
| 88 | $-H$ | $-CONH_2$ | $-H$ | $-H$ | $-H$ | $-H$ | 1 | O | |
| 89 | $-H$ | $-H$ | $-CONH_2$ | $-H$ | $-H$ | $-H$ | 1 | O | A |
| 90 | $-CONHCH_3$ | $-H$ | $-H$ | $-H$ | $-H$ | $-H$ | 1 | O | single |
| 91 | $-H$ | $-CONHCH_3$ | $-H$ | $-H$ | $-H$ | $-H$ | 1 | O | bond |
| 92 | $-H$ | $-H$ | $-CONHCH_3$ | $-H$ | $-H$ | $-H$ | 1 | O | |
| 93 | $-CONHC_2H_5$ | $-H$ | $-H$ | $-H$ | $-H$ | $-H$ | 1 | O | |
| 94 | $-CONHC_3H_7{}^n$ | $-H$ | $-H$ | $-H$ | $-H$ | $-H$ | 1 | O | |
| 95 | $-CONHC_4H_9{}^n$ | $-H$ | $-H$ | $-H$ | $-H$ | $-H$ | 1 | O | |
| 96 | $-CONHC_5H_{11}{}^n$ | $-H$ | $-H$ | $-H$ | $-H$ | $-H$ | 1 | O | |
| 97 | $-CONHC_6H_{13}{}^n$ | $-H$ | $-H$ | $-H$ | $-H$ | $-H$ | 1 | O | |
| 98 | $-CONHC_7H_{15}{}^n$ | $-H$ | $-H$ | $-H$ | $-H$ | $-H$ | 1 | O | |
| 99 | $-CONHC_6H_5$ | $-H$ | $-H$ | $-H$ | $-H$ | $-H$ | 1 | O | |
| 100 | $-H$ | $-CONHC_6H_5$ | $-H$ | $-H$ | $-H$ | $-H$ | 1 | O | |
| 101 | $-H$ | $-H$ | $-CONHC_6H_5$ | $-H$ | $-H$ | $-H$ | 1 | O | |
| 102 | $-CON(CH_3)_2$ | $-H$ | $-H$ | $-H$ | $-H$ | $-H$ | 1 | O | |
| 103 | $-H$ | $-CON(CH_3)_2$ | $-H$ | $-H$ | $-H$ | $-H$ | 1 | O | |
| 104 | $-H$ | $-H$ | $-CON(CH_3)_2$ | $-H$ | $-H$ | $-H$ | 1 | O | |

TABLE 1-continued

| Compound No. | R¹ | R² | R³ | R⁴ | R⁵ | R⁶ | n | X | |
|---|---|---|---|---|---|---|---|---|---|
| 105 | $-NH_2$ | $-H$ | $-H$ | $-H$ | $-H$ | $-H$ | 1 | O | |
| 106 | $-H$ | $-NH_2$ | $-H$ | $-H$ | $-H$ | $-H$ | 1 | O | |
| 107 | $-H$ | $-H$ | $-NH_2$ | $-H$ | $-H$ | $-H$ | 1 | O | |
| 108 | $-NHCH_3$ | $-H$ | $-H$ | $-H$ | $-H$ | $-H$ | 1 | O | |
| 109 | $-H$ | $-NHCH_3$ | $-H$ | $-H$ | $-H$ | $-H$ | 1 | O | |
| 110 | $-H$ | $-H$ | $-NHCH_3$ | $-H$ | $-H$ | $-H$ | 1 | O | |
| 111 | $-NHC_2H_5$ | $-H$ | $-H$ | $-H$ | $-H$ | $-H$ | 1 | O | |
| 112 | $-NHC_3H_7^n$ | $-H$ | $-H$ | $-H$ | $-H$ | $-H$ | 1 | O | |
| 113 | $-NHCH(CH_3)_2$ | $-H$ | $-H$ | $-H$ | $-H$ | $-H$ | 1 | O | |
| 114 | $-NHC_4H_9^n$ | $-H$ | $-H$ | $-H$ | $-H$ | $-H$ | 1 | O | A |
| 115 | $-NHC_5H_{11}^n$ | $-H$ | $-H$ | $-H$ | $-H$ | $-H$ | 1 | O | single |
| 116 | $-NHC_6H_{13}^n$ | $-H$ | $-H$ | $-H$ | $-H$ | $-H$ | 1 | O | bond |
| 117 | $-NHC_7H_{15}^n$ | $-H$ | $-H$ | $-H$ | $-H$ | $-H$ | 1 | O | |
| 118 | $-N(CH_3)_2$ | $-H$ | $-H$ | $-H$ | $-H$ | $-H$ | 1 | O | |
| 119 | $-H$ | $-N(CH_3)_2$ | $-H$ | $-H$ | $-H$ | $-H$ | 1 | O | |
| 120 | $-H$ | $-H$ | $-N(CH_3)_2$ | $-H$ | $-H$ | $-H$ | 1 | O | |
| 121 | $-NHCOCH_3$ | $-H$ | $-H$ | $-H$ | $-H$ | $-H$ | 1 | O | |
| 122 | $-H$ | $-NHCOCH_3$ | $-H$ | $-H$ | $-H$ | $-H$ | 1 | O | |
| 123 | $-H$ | $-H$ | $-NHCOCH_3$ | $-H$ | $-H$ | $-H$ | 1 | O | |
| 124 | $-NHCOC_2H_5$ | $-H$ | $-H$ | $-H$ | $-H$ | $-H$ | 1 | O | |
| 125 | $-NHCOC_3H_7^n$ | $-H$ | $-H$ | $-H$ | $-H$ | $-H$ | 1 | O | |
| 126 | $-NHCOCH(CH_3)_2$ | $-H$ | $-H$ | $-H$ | $-H$ | $-H$ | 1 | O | |
| 127 | $-NHCOC_4H_9^n$ | $-H$ | $-H$ | $-H$ | $-H$ | $-H$ | 1 | O | |
| 128 | $-NHCOC_5H_{11}^n$ | $-H$ | $-H$ | $-H$ | $-H$ | $-H$ | 1 | O | |
| 129 | $-NHCOC_6H_{13}^n$ | $-H$ | $-H$ | $-H$ | $-H$ | $-H$ | 1 | O | |
| 130 | $-NHCOC_7H_{15}^n$ | $-H$ | $-H$ | $-H$ | $-H$ | $-H$ | 1 | O | |
| 131 | $-NHCOC_6H_5$ | $-H$ | $-H$ | $-H$ | $-H$ | $-H$ | 1 | O | |
| 132 | $-H$ | $-NHCOC_6H_5$ | $-H$ | $-H$ | $-H$ | $-H$ | 1 | O | |
| 133 | $-H$ | $-H$ | $-NHCOC_6H_5$ | $-H$ | $-H$ | $-H$ | 1 | O | |
| 134 | $-CHO$ | $-H$ | $-H$ | $-H$ | $-H$ | $-H$ | 1 | O | |
| 135 | $-H$ | $-CHO$ | $-H$ | $-H$ | $-H$ | $-H$ | 1 | O | |
| 136 | $-H$ | $-H$ | $-CHO$ | $-H$ | $-H$ | $-H$ | 1 | O | |
| 137 |  | $-H$ | $-H$ | $-H$ | $-H$ | $-H$ | 1 | O | |
| 138 | $-H$ |  | $-H$ | $-H$ | $-H$ | $-H$ | 1 | O | |
| 139 | $-H$ | $-H$ |  | $-H$ | $-H$ | $-H$ | 1 | O | |
| 140 | $-CF_3$ | $-H$ | $-H$ | $-H$ | $-H$ | $-H$ | 1 | O | A |
| 141 | $-H$ | $-CF_3$ | $-H$ | $-H$ | $-H$ | $-H$ | 1 | O | single |
| 142 | $-H$ | $-H$ | $-CF_3$ | $-H$ | $-H$ | $-H$ | 1 | O | bond |
| 143 | $-CCl_3$ | $-H$ | $-H$ | $-H$ | $-H$ | $-H$ | 1 | O | |
| 144 | $-H$ | $-CCl_3$ | $-H$ | $-H$ | $-H$ | $-H$ | 1 | O | |
| 145 | $-H$ | $-H$ | $-CCl_3$ | $-H$ | $-H$ | $-H$ | 1 | O | |
| 146 | $-F$ | $-F$ | $-H$ | $-H$ | $-H$ | $-H$ | 1 | O | |
| 147 | $-F$ | $-H$ | $-F$ | $-H$ | $-H$ | $-H$ | 1 | O | |
| 148 | $-F$ | $-H$ | $-H$ | $-F$ | $-H$ | $-H$ | 1 | O | |
| 149 | $-F$ | $-H$ | $-H$ | $-H$ | $-F$ | $-H$ | 1 | O | |
| 150 | $-H$ | $-F$ | $-H$ | $-F$ | $-H$ | $-H$ | 1 | O | |
| 151 | $-H$ | $-H$ | $-F$ | $-F$ | $-H$ | $-H$ | 1 | O | |
| 152 | $-H$ | $-H$ | $-H$ | $-H$ | $-F$ | $-H$ | 1 | O | |
| 153 | $-F$ | $-H$ | $-F$ | $-H$ | $-F$ | $-H$ | 1 | O | |
| 154 | $-F$ | $-F$ | $-F$ | $-F$ | $-F$ | $-H$ | 1 | O | |
| 155 | $-Cl$ | $-Cl$ | $-H$ | $-H$ | $-H$ | $-H$ | 1 | O | |
| 156 | $-Cl$ | $-H$ | $-Cl$ | $-H$ | $-H$ | $-H$ | 1 | O | |
| 157 | $-Cl$ | $-H$ | $-H$ | $-Cl$ | $-H$ | $-H$ | 1 | O | |
| 158 | $-Cl$ | $-H$ | $-H$ | $-H$ | $-Cl$ | $-H$ | 1 | O | |
| 159 | $-H$ | $-Cl$ | $-Cl$ | $-H$ | $-H$ | $-H$ | 1 | O | |
| 160 | $-H$ | $-Cl$ | $-H$ | $-Cl$ | $-H$ | $-H$ | 1 | O | |
| 161 | $-H$ | $-Cl$ | $-H$ | $-H$ | $-Cl$ | $-H$ | 1 | O | |
| 162 | $-Cl$ | $-H$ | $-Cl$ | $-H$ | $-Cl$ | $-H$ | 1 | O | |
| 163 | $-Cl$ | $-Cl$ | $-Cl$ | $-Cl$ | $-Cl$ | $-H$ | 1 | O | A |

TABLE 1-continued

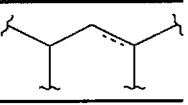

| Compound No. | $R^1$ | $R^2$ | $R^3$ | $R^4$ | $R^5$ | $R^6$ | n | X | |
|---|---|---|---|---|---|---|---|---|---|
| 164 | $-CF_3$ | $-H$ | $-CF_3$ | $-H$ | $-H$ | $-H$ | 1 | O | single bond |
| 165 | $-H$ | $-CF_3$ | $-H$ | $-CF_3$ | $-H$ | $-H$ | 1 | O | |
| 166 | $-Cl$ | $-H$ | $-F$ | $-H$ | $-H$ | $-H$ | 1 | O | |
| 167 | $-Cl$ | $-H$ | $-H$ | $-H$ | $-F$ | $-H$ | 1 | O | |
| 168 | $-F$ | $-CF_3$ | $-H$ | $-H$ | $-H$ | $-H$ | 1 | O | |
| 169 | $-F$ | $-H$ | $-CF_3$ | $-H$ | $-H$ | $-H$ | 1 | O | |
| 170 | $-F$ | $-H$ | $-H$ | $-CF_3$ | $-H$ | $-H$ | 1 | O | |
| 171 | $-F$ | $-H$ | $-H$ | $-H$ | $-CF_3$ | $-H$ | 1 | O | |
| 172 | $-H$ | $-F$ | $-CF_3$ | $-H$ | $-H$ | $-H$ | 1 | O | |
| 173 | $-H$ | $-F$ | $-H$ | $-CF_3$ | $-H$ | $-H$ | 1 | O | |
| 174 | $-NO_2$ | $-NO_2$ | $-H$ | $-H$ | $-H$ | $-H$ | 1 | O | |
| 175 | $-NO_2$ | $-H$ | $-NO_2$ | $-H$ | $-H$ | $-H$ | 1 | O | |
| 176 | $-NO_2$ | $-H$ | $-H$ | $-NO_2$ | $-H$ | $-H$ | 1 | O | |
| 177 | $-NO_2$ | $-H$ | $-H$ | $-H$ | $-NO_2$ | $-H$ | 1 | O | |
| 178 | $-H$ | $-NO_2$ | $-NO_2$ | $-H$ | $-H$ | $-H$ | 1 | O | |
| 179 | $-H$ | $-NO_2$ | $-H$ | $-NO_2$ | $-H$ | $-H$ | 1 | O | |
| 180 | $-H$ | $-NO_2$ | $-H$ | $-H$ | $-NO_2$ | $-H$ | 1 | O | |
| 181 | $-F$ | $-H$ | $-H$ | $-NO_2$ | $-H$ | $-H$ | 1 | O | |
| 182 | $-H$ | $-NO_2$ | $-F$ | $-H$ | $-H$ | $-H$ | 1 | O | |
| 183 | $-H$ | $-H$ | $-H$ | $-H$ | $-H$ | $--$ | 0 | S | |
| 184 | $-H$ | $-H$ | $-H$ | $-H$ | $-H$ | $-H$ | 1 | S | |
| 185 | $-H$ | $-H$ | $-H$ | $-H$ | $-H$ | $-H$ | 2 | S | |
| 186 | $-H$ | $-H$ | $-H$ | $-H$ | $-H$ | $-H$ | 3 | S | A single bond |
| 187 | $-F$ | $-H$ | $-H$ | $-H$ | $-H$ | $-H$ | 1 | S | |
| 188 | $-Cl$ | $-H$ | $-H$ | $-H$ | $-H$ | $-H$ | 1 | S | |
| 189 | $-Br$ | $-H$ | $-H$ | $-H$ | $-H$ | $-H$ | 1 | S | |
| 190 | $-I$ | $-H$ | $-H$ | $-H$ | $-H$ | $-H$ | 1 | S | |
| 191 | $-CH_3$ | $-H$ | $-H$ | $-H$ | $-H$ | $-H$ | 1 | S | |
| 192 | $-C_2H_5$ | $-H$ | $-H$ | $-H$ | $-H$ | $-H$ | 1 | S | |
| 193 | $-C_3H_7^n$ | $-H$ | $-H$ | $-H$ | $-H$ | $-H$ | 1 | S | |
| 194 | $-CH(CH_3)_2$ | $-H$ | $-H$ | $-H$ | $-H$ | $-H$ | 1 | S | |
| 195 | $-C_4H_9^n$ | $-H$ | $-H$ | $-H$ | $-H$ | $-H$ | 1 | S | |
| 196 | $-C_5H_{11}^n$ | $-H$ | $-H$ | $-H$ | $-H$ | $-H$ | 1 | S | |
| 197 | $-C_6H_{13}^n$ | $-H$ | $-H$ | $-H$ | $-H$ | $-H$ | 1 | S | |
| 198 | $-C_7H_{15}^n$ | $-H$ | $-H$ | $-H$ | $-H$ | $-H$ | 1 | S | |
| 199 | $-OCH_3$ | $-H$ | $-H$ | $-H$ | $-H$ | $-H$ | 1 | S | |
| 200 | $-OC_2H_5$ | $-H$ | $-H$ | $-H$ | $-H$ | $-H$ | 1 | S | |
| 201 | $-OC_3H_7^n$ | $-H$ | $-H$ | $-H$ | $-H$ | $-H$ | 1 | S | |
| 202 | $-OCH(CH_3)_2$ | $-H$ | $-H$ | $-H$ | $-H$ | $-H$ | 1 | S | |
| 203 | $-OC_4H_9^n$ | $-H$ | $-H$ | $-H$ | $-H$ | $-H$ | 1 | S | |
| 204 | $-OC_5H_{11}^n$ | $-H$ | $-H$ | $-H$ | $-H$ | $-H$ | 1 | S | |
| 205 | $-OC_6H_{13}^n$ | $-H$ | $-H$ | $-H$ | $-H$ | $-H$ | 1 | S | |
| 206 | $-OC_7H_{15}^n$ | $-H$ | $-H$ | $-H$ | $-H$ | $-H$ | 1 | S | A single bond |
| 207 | $-OCOCH_3$ | $-H$ | $-H$ | $-H$ | $-H$ | $-H$ | 1 | S | |
| 208 | $-OCOC_2H_5$ | $-H$ | $-H$ | $-H$ | $-H$ | $-H$ | 1 | S | |
| 209 | $-OCOC_3H_7^n$ | $-H$ | $-H$ | $-H$ | $-H$ | $-H$ | 1 | S | |
| 210 | $-OCOCH(CH_3)_2$ | $-H$ | $-H$ | $-H$ | $-H$ | $-H$ | 1 | S | |
| 211 | $-OCOC_4H_9^n$ | $-H$ | $-H$ | $-H$ | $-H$ | $-H$ | 1 | S | |
| 212 | $-OCOC_5H_{11}^n$ | $-H$ | $-H$ | $-H$ | $-H$ | $-H$ | 1 | S | |
| 213 | $-OCOC_6H_{13}^n$ | $-H$ | $-H$ | $-H$ | $-H$ | $-H$ | 1 | S | |
| 214 | $-OCOC_7H_{15}^n$ | $-H$ | $-H$ | $-H$ | $-H$ | $-H$ | 1 | S | |
| 215 | $-OCOC_6H_5$ | $-H$ | $-H$ | $-H$ | $-H$ | $-H$ | 1 | S | |
| 216 | $-CN$ | $-H$ | $-H$ | $-H$ | $-H$ | $-H$ | 1 | S | |
| 217 | $-NO_2$ | $-H$ | $-H$ | $-H$ | $-H$ | $-H$ | 1 | S | |
| 218 | $-COOH$ | $-H$ | $-H$ | $-H$ | $-H$ | $-H$ | 1 | S | |
| 219 | $-COOCH_3$ | $-H$ | $-H$ | $-H$ | $-H$ | $-H$ | 1 | S | |
| 220 | $-COOC_2H_5$ | $-H$ | $-H$ | $-H$ | $-H$ | $-H$ | 1 | S | |
| 221 | $-COOC_3H_7^n$ | $-H$ | $-H$ | $-H$ | $-H$ | $-H$ | 1 | S | |
| 222 | $-COOCH(CH_3)_2$ | $-H$ | $-H$ | $-H$ | $-H$ | $-H$ | 1 | S | |
| 223 | $COOC_4H_9^n$ | $-H$ | $-H$ | $-H$ | $-H$ | $-H$ | 1 | S | |
| 224 | $-COOC_5H_{11}^n$ | $-H$ | $-H$ | $-H$ | $-H$ | $-H$ | 1 | S | |
| 225 | $-COOC_6H_{13}^n$ | $-H$ | $-H$ | $-H$ | $-H$ | $-H$ | 1 | S | |
| 226 | $-COOC_7H_{15}^n$ | $-H$ | $-H$ | $-H$ | $-H$ | $-H$ | 1 | S | |
| 227 | $-CO\,NH_2$ | $-H$ | $-H$ | $-H$ | $-H$ | $-H$ | 1 | S | |
| 228 | $-CONHCH_3$ | $-H$ | $-H$ | $-H$ | $-H$ | $-H$ | 1 | S | |
| 229 | $-CONHC_2H_5$ | $-H$ | $-H$ | $-H$ | $-H$ | $-H$ | 1 | S | |
| 230 | $-CONHC_3H_7^n$ | $-H$ | $-H$ | $-H$ | $-H$ | $-H$ | 1 | S | |
| 231 | $-CONHC_4H_9^n$ | $-H$ | $-H$ | $-H$ | $-H$ | $-H$ | 1 | S | |
| 232 | $-CONHC_5H_{11}^n$ | $-H$ | $-H$ | $-H$ | $-H$ | $-H$ | 1 | S | A single bond |
| 233 | $-CONHC_6H_{13}^n$ | $-H$ | $-H$ | $-H$ | $-H$ | $-H$ | 1 | S | |
| 234 | $-CONHC_7H_{15}^n$ | $-H$ | $-H$ | $-H$ | $-H$ | $-H$ | 1 | S | |
| 235 | $-CONHC_8H_5$ | $-H$ | $-H$ | $-H$ | $-H$ | $-H$ | 1 | S | |
| 236 | $-CON(CH_3)_2$ | $-H$ | $-H$ | $-H$ | $-H$ | $-H$ | 1 | S | |
| 237 | $-NH_2$ | $-H$ | $-H$ | $-H$ | $-H$ | $-H$ | 1 | S | |

TABLE 1-continued

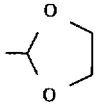

| Compound No. | R¹ | R² | R³ | R⁴ | R⁵ | R⁶ | n | X | |
|---|---|---|---|---|---|---|---|---|---|
| 238 | $-NHCH_3$ | $-H$ | $-H$ | $-H$ | $-H$ | $-H$ | 1 | S | |
| 239 | $-NHC_2H_5$ | $-H$ | $-H$ | $-H$ | $-H$ | $-H$ | 1 | S | |
| 240 | $-NHC_3H_7{}^n$ | $-H$ | $-H$ | $-H$ | $-H$ | $-H$ | 1 | S | |
| 241 | $-NHC_4H_9{}^n$ | $-H$ | $-H$ | $-H$ | $-H$ | $-H$ | 1 | S | |
| 242 | $-NHC_5H_{11}{}^n$ | $-H$ | $-H$ | $-H$ | $-H$ | $-H$ | 1 | S | |
| 243 | $-NHC_6H_{13}{}^n$ | $-H$ | $-H$ | $-H$ | $-H$ | $-H$ | 1 | S | |
| 244 | $-NHC_7H_{15}{}^n$ | $-H$ | $-H$ | $-H$ | $-H$ | $-H$ | 1 | S | |
| 245 | $-N(CH_3)_2$ | $-H$ | $-H$ | $-H$ | $-H$ | $-H$ | 1 | S | |
| 246 | $-NHCOCH_3$ | $-H$ | $-H$ | $-H$ | $-H$ | $-H$ | 1 | S | |
| 247 | $-NHCOC_2H_5$ | $-H$ | $-H$ | $-H$ | $-H$ | $-H$ | 1 | S | |
| 248 | $-NHCOC_3H_7{}^n$ | $-H$ | $-H$ | $-H$ | $-H$ | $-H$ | 1 | S | |
| 249 | $-NHCOC_4H_9{}^n$ | $-H$ | $-H$ | $-H$ | $-H$ | $-H$ | 1 | S | |
| 250 | $-NHCOC_5H_{11}{}^n$ | $-H$ | $-H$ | $-H$ | $-H$ | $-H$ | 1 | S | |
| 251 | $-NHCOC_6H_{13}{}^n$ | $-H$ | $-H$ | $-H$ | $-H$ | $-H$ | 1 | S | |
| 252 | $-NHCOC_7H_{15}{}^n$ | $-H$ | $-H$ | $-H$ | $-H$ | $-H$ | 1 | S | |
| 253 | $-NHCOC_6H_5$ | $-H$ | $-H$ | $-H$ | $-H$ | $-H$ | 1 | S | |
| 254 | $-CHO$ | $-H$ | $-H$ | $-H$ | $-H$ | $-H$ | 1 | S | |
| 255 | (dioxolane) | $-H$ | $-H$ | $-H$ | $-H$ | $-H$ | 1 | S | |
| 256 | $-CF_3$ | $-H$ | $-H$ | $-H$ | $-H$ | $-H$ | 1 | S | A single bond |
| 257 | $-CCl_3$ | $-H$ | $-H$ | $-H$ | $-H$ | $-H$ | 1 | S | |
| 258 | $-F$ | $-F$ | $-H$ | $-H$ | $-H$ | $-H$ | 1 | S | |
| 259 | $-F$ | $-H$ | $-F$ | $-H$ | $-H$ | $-H$ | 1 | S | |
| 260 | $-F$ | $-H$ | $-H$ | $-F$ | $-H$ | $-H$ | 1 | S | |
| 261 | $-F$ | $-H$ | $-H$ | $-H$ | $-F$ | $-H$ | 1 | S | |
| 262 | $-H$ | $-F$ | $-F$ | $-H$ | $-H$ | $-H$ | 1 | S | |
| 263 | $-H$ | $-F$ | $-H$ | $-F$ | $-H$ | $-H$ | 1 | S | |
| 264 | $-H$ | $-F$ | $-H$ | $-H$ | $-F$ | $-H$ | 1 | S | |
| 265 | $-F$ | $-H$ | $-F$ | $-H$ | $-F$ | $-H$ | 1 | S | |
| 266 | $-F$ | $-F$ | $-F$ | $-F$ | $-F$ | $-H$ | 1 | S | |
| 267 | $-Cl$ | $-Cl$ | $-H$ | $-H$ | $-H$ | $-H$ | 1 | S | |
| 268 | $-Cl$ | $-H$ | $-Cl$ | $-H$ | $-H$ | $-H$ | 1 | S | |
| 269 | $-Cl$ | $-H$ | $-H$ | $-Cl$ | $-H$ | $-H$ | 1 | S | |
| 270 | $-Cl$ | $-H$ | $-H$ | $-H$ | $-Cl$ | $-H$ | 1 | S | |
| 271 | $-H$ | $-Cl$ | $-Cl$ | $-H$ | $-H$ | $-H$ | 1 | S | |
| 272 | $-H$ | $-H$ | $-Cl$ | $-Cl$ | $-H$ | $-H$ | 1 | S | |
| 273 | $-H$ | $-Cl$ | $-H$ | $-H$ | $-Cl$ | $-H$ | 1 | S | |
| 274 | $-Cl$ | $-H$ | $-Cl$ | $-H$ | $-Cl$ | $-H$ | 1 | S | |
| 275 | $-Cl$ | $-Cl$ | $-Cl$ | $-Cl$ | $-Cl$ | $-H$ | 1 | S | |
| 276 | $-CF_3$ | $-H$ | $-CF_3$ | $-H$ | $-H$ | $-H$ | 1 | S | |
| 277 | $-H$ | $-CF_3$ | $-H$ | $-CF_3$ | $-H$ | $-H$ | 1 | S | |
| 278 | $-Cl$ | $-H$ | $-F$ | $-H$ | $-H$ | $-H$ | 1 | S | |
| 279 | $-Cl$ | $-H$ | $-H$ | $-H$ | $-F$ | $-H$ | 1 | S | |
| 280 | $-F$ | $-CF_3$ | $-H$ | $-H$ | $-H$ | $-H$ | 1 | S | |
| 281 | $-F$ | $-H$ | $-CF_3$ | $-H$ | $-H$ | $-H$ | 1 | S | |
| 282 | $-F$ | $-H$ | $-H$ | $-CF_3$ | $-H$ | $-H$ | 1 | S | |
| 283 | $-F$ | $-H$ | $-H$ | $-H$ | $-CF_3$ | $-H$ | 1 | S | A single bond |
| 284 | $-H$ | $-F$ | $-CF_3$ | $-H$ | $-H$ | $-H$ | 1 | S | |
| 285 | $-H$ | $-F$ | $-H$ | $-CF_3$ | $-H$ | $-H$ | 1 | S | |
| 286 | $-NO_2$ | $-NO_2$ | $-H$ | $-H$ | $-H$ | $-H$ | 1 | S | |
| 287 | $-NO_2$ | $-H$ | $-NO_2$ | $-H$ | $-H$ | $-H$ | 1 | S | |
| 288 | $-NO_2$ | $-H$ | $-H$ | $-NO_2$ | $-H$ | $-H$ | 1 | S | |
| 289 | $-NO_2$ | $-H$ | $-H$ | $-H$ | $-NO_2$ | $-H$ | 1 | S | |
| 290 | $-H$ | $-NO_2$ | $-NO_2$ | $-H$ | $-H$ | $-H$ | 1 | S | |
| 291 | $-H$ | $-NO_2$ | $-H$ | $-NO_2$ | $-H$ | $-H$ | 1 | S | |
| 292 | $-H$ | $-NO_2$ | $-H$ | $-H$ | $-NO_2$ | $-H$ | 1 | S | |
| 293 | $-F$ | $-H$ | $-H$ | $-NO_2$ | $-H$ | $-H$ | 1 | S | |
| 294 | $-H$ | $-NO_2$ | $-F$ | $-H$ | $-H$ | $-H$ | 1 | S | |
| 295 | $-H$ | $-H$ | $-H$ | $-H$ | $-H$ | — | 0 | O | |
| 296 | $-H$ | $-H$ | $-H$ | $-H$ | $-H$ | $-H$ | 1 | O | |
| 297 | $-H$ | $-H$ | $-H$ | $-H$ | $-H$ | $-H$ | 2 | O | |
| 298 | $-H$ | $-H$ | $-H$ | $-H$ | $-H$ | $-H$ | 3 | O | |
| 299 | $-F$ | $-H$ | $-H$ | $-H$ | $-H$ | $-H$ | 1 | O | |
| 300 | $-H$ | $-F$ | $-H$ | $-H$ | $-H$ | $-H$ | 1 | O | |
| 301 | $-H$ | $-H$ | $-F$ | $-H$ | $-H$ | $-H$ | 1 | O | |
| 302 | $-Cl$ | $-H$ | $-H$ | $-H$ | $-H$ | $-H$ | 1 | O | |
| 303 | $-H$ | $-Cl$ | $-H$ | $-H$ | $-H$ | $-H$ | 1 | O | |
| 304 | $-H$ | $-H$ | $-Cl$ | $-H$ | $-H$ | $-H$ | 1 | O | |
| 305 | $-Br$ | $-H$ | $-H$ | $-H$ | $-H$ | $-H$ | 1 | O | A |

TABLE 1-continued

| Compound No. | $R^1$ | $R^2$ | $R^3$ | $R^4$ | $R^5$ | $R^6$ | n | X | 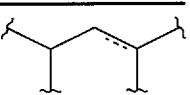 |
|---|---|---|---|---|---|---|---|---|---|
| 306 | —H | —Br | —H | —H | —H | —H | 1 | O | double bond |
| 307 | —H | —H | —Br | —H | —H | —H | 1 | O | |
| 308 | —I | —H | —H | —H | —H | —H | 1 | O | |
| 309 | —H | —I | —H | —H | —H | —H | 1 | O | |
| 310 | —H | —H | —I | —H | —H | —H | 1 | O | |
| 311 | —$CH_3$ | —H | —H | —H | —H | —H | 1 | O | |
| 312 | —H | —$CH_3$ | —H | —H | —H | —H | 1 | O | |
| 313 | —H | —H | —$CH_3$ | —H | —H | —H | 1 | O | |
| 314 | —$C_2H_5$ | —H | —H | —H | —H | —H | 1 | O | |
| 315 | —H | —$C_2H_5$ | —H | —H | —H | —H | 1 | O | |
| 316 | —H | —H | —$C_2H_5$ | —H | —H | —H | 1 | O | |
| 317 | —$C_3H_7^n$ | —H | —H | —H | —H | —H | 1 | O | |
| 318 | —H | —$C_3H_7^n$ | —H | —H | —H | —H | 1 | O | |
| 319 | —H | —H | —$C_3H_7^n$ | —H | —H | —H | 1 | O | |
| 320 | —$CH(CH_3)_2$ | —H | —H | —H | —H | —H | 1 | O | |
| 321 | —H | —$CH(CH_3)_2$ | —H | —H | —H | —H | 1 | O | |
| 322 | —H | —H | —$CH(CH_3)_2$ | —H | —H | —H | 1 | O | |
| 323 | —$C_4H_9^n$ | —H | —H | —H | —H | —H | 1 | O | |
| 324 | —$C_5H_{11}^n$ | —H | —H | —H | —H | —H | 1 | O | |
| 325 | —$C_6H_{13}^n$ | —H | —H | —H | —H | —H | 1 | O | |
| 326 | —$C_7H_{15}^n$ | —H | —H | —H | —H | —H | 1 | O | |
| 327 | —$OCH_3$ | —H | —H | —H | —H | —H | 1 | O | |
| 328 | —H | —$OCH_3$ | —H | —H | —H | —H | 1 | O | |
| 329 | —H | —H | —$OCH_3$ | —H | —H | —H | 1 | O | |
| 330 | —$OC_2H_5$ | —H | —H | —H | —H | —H | 1 | O | |
| 331 | —H | —$OC_2H_5$ | —H | —H | —H | —H | 1 | O | |
| 332 | —H | —H | —$OC_2H_5$ | —H | —H | —H | 1 | O | A double bond |
| 333 | —$OC_3H_7^n$ | —H | —H | —H | —H | —H | 1 | O | |
| 334 | —H | —$OC_3H_7^n$ | —H | —H | —H | —H | 1 | O | |
| 335 | —H | —H | —$OC_3H_7^n$ | —H | —H | —H | 1 | O | |
| 336 | —$OCH(CH_3)_2$ | —H | —H | —H | —H | —H | 1 | O | |
| 337 | —H | —$OCH(CH_3)_2$ | —H | —H | —H | —H | 1 | O | |
| 338 | —H | —H | —$OCH(CH_3)_2$ | —H | —H | —H | 1 | O | |
| 339 | —$OC_4H_9^n$ | —H | —H | —H | —H | —H | 1 | O | |
| 340 | —$OC_5H_{11}^n$ | —H | —H | —H | —H | —H | 1 | O | |
| 341 | —$OC_6H_{13}^n$ | —H | —H | —H | —H | —H | 1 | O | |
| 342 | —$OC_7H_{15}^n$ | —H | —H | —H | —H | —H | 1 | O | |
| 343 | —$OCOCH_3$ | —H | —H | —H | —H | —H | 1 | O | |
| 344 | —H | —$OCOCH_3$ | —H | —H | —H | —H | 1 | O | |
| 345 | —H | —H | —$OCOCH_3$ | —H | —H | —H | 1 | O | |
| 346 | —$OCOC_2H_5$ | —H | —H | —H | —H | —H | 1 | O | |
| 347 | —$OCOC_3H_7^n$ | —H | —H | —H | —H | —H | 1 | O | |
| 348 | —$OCOCH(CH_3)_2$ | —H | —H | —H | —H | —H | 1 | O | |
| 349 | —$OCOC_4H_9^n$ | —H | —H | —H | —H | —H | 1 | O | |
| 350 | —$OCOC_5H_{11}^n$ | —H | —H | —H | —H | —H | 1 | O | |
| 351 | —$OCOC_6H_{13}^n$ | —H | —H | —H | —H | —H | 1 | O | |
| 352 | —$OCOC_7H_{15}^n$ | —H | —H | —H | —H | —H | 1 | O | |
| 353 | —$OCOC_6H_5^n$ | —H | —H | —H | —H | —H | 1 | O | |
| 354 | —H | —$OCOC_6H_5$ | —H | —H | —H | —H | 1 | O | |
| 355 | —H | —H | —$OCOC_6H_5$ | —H | —H | —H | 1 | O | |
| 356 | —CN | —H | —H | —H | —H | —H | 1 | O | |
| 357 | —H | —CN | —H | —H | —H | —H | 1 | O | |
| 358 | —H | —H | —CN | —H | —H | —H | 1 | O | A double bond |
| 359 | —$NO_2$ | —H | —H | —H | —H | —H | 1 | O | |
| 360 | —H | —$NO_2$ | —H | —H | —H | —H | 1 | O | |
| 361 | —H | —H | —$NO_2$ | —H | —H | —H | 1 | O | |
| 362 | —COOH | —H | —H | —H | —H | —H | 1 | O | |
| 363 | —H | —COOH | —H | —H | —H | —H | 1 | O | |
| 364 | —H | —H | —COOH | —H | —H | —H | 1 | O | |
| 365 | —$COOCH_3$ | —H | —H | —H | —H | —H | 1 | O | |
| 366 | —H | —$COOCH_3$ | —H | —H | —H | —H | 1 | O | |
| 367 | —H | —H | —$COOCH_3$ | —H | —H | —H | 1 | O | |
| 368 | —$COOC_2H_5$ | —H | —H | —H | —H | —H | 1 | O | |
| 369 | —H | —$COOC_2H_5$ | —H | —H | —H | —H | 1 | O | |
| 370 | —H | —H | —$COOC_2H_5$ | —H | —H | —H | 1 | O | |
| 371 | —$COOC_3H_7^n$ | —H | —H | —H | —H | —H | 1 | O | |
| 372 | —H | —$COOC_3H_7^n$ | —H | —H | —H | —H | 1 | O | |
| 373 | —H | —H | —$COOC_3H_7^n$ | —H | —H | —H | 1 | O | |
| 374 | —$COOCH(CH_3)_2$ | —H | —H | —H | —H | —H | 1 | O | |
| 375 | —H | —$COOCH(CH_3)_2$ | —H | —H | —H | —H | 1 | O | |
| 376 | —H | —H | —$COOCH(CH_3)_2$ | —H | —H | —H | 1 | O | |
| 377 | —$COOC_4H_9^n$ | —H | —H | —H | —H | —H | 1 | O | |
| 378 | —$COOC_5H_{11}^n$ | —H | —H | —H | —H | —H | 1 | O | |
| 379 | —$COOC_6H_{13}^n$ | —H | —H | —H | —H | —H | 1 | O | |

TABLE 1-continued

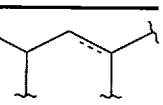

| Compound No. | R¹ | R² | R³ | R⁴ | R⁵ | R⁶ | n | X | |
|---|---|---|---|---|---|---|---|---|---|
| 380 | —COOC$_7$H$_{15}$$^n$ | —H | —H | —H | —H | —H | 1 | O | |
| 381 | —CONH$_2$ | —H | —H | —H | —H | —H | 1 | O | |
| 382 | —H | —CONH$_2$ | —H | —H | —H | —H | 1 | O | A |
| 383 | —H | —H | —CONH$_2$ | —H | —H | —H | 1 | O | double |
| 384 | —CONHCH$_3$ | —H | —H | —H | —H | —H | 1 | O | bond |
| 385 | —H | —CONHCH$_3$ | —H | —H | —H | —H | 1 | O | |
| 386 | —H | —H | —CONHCH$_3$ | —H | —H | —H | 1 | O | |
| 387 | —CONHC$_2$H$_5$ | —H | —H | —H | —H | —H | 1 | O | |
| 388 | —CONHC$_3$H$_7$$^n$ | —H | —H | —H | —H | —H | 1 | O | |
| 389 | —CONHC$_4$H$_9$$^n$ | —H | —H | —H | —H | —H | 1 | O | |
| 390 | —CONHC$_5$H$_{11}$$^n$ | —H | —H | —H | —H | —H | 1 | O | |
| 391 | —CONHC$_6$H$_{13}$$^n$ | —H | —H | —H | —H | —H | 1 | O | |
| 392 | —CONHC$_7$H$_{15}$$^n$ | —H | —H | —H | —H | —H | 1 | O | |
| 393 | —CONHC$_6$H$_5$ | —H | —H | —H | —H | —H | 1 | O | |
| 394 | —H | —CONHC$_6$H$_5$ | —H | —H | —H | —H | 1 | O | |
| 395 | —H | —H | —CONHC$_6$H$_5$ | —H | —H | —H | 1 | O | |
| 396 | —CON(CH$_3$)$_2$ | —H | —H | —H | —H | —H | 1 | O | |
| 397 | —H | —CON(CH$_3$)$_2$ | —H | —H | —H | —H | 1 | O | |
| 398 | —H | —H | —CON(CH$_3$)$_2$ | —H | —H | —H | 1 | O | |
| 399 | —NH$_2$ | —H | —H | —H | —H | —H | 1 | O | |
| 400 | —H | —NH$_2$ | —H | —H | —H | —H | 1 | O | |
| 401 | —H | —H | —NH$_2$ | —H | —H | —H | 1 | O | |
| 402 | —NHCH$_3$ | —H | —H | —H | —H | —H | 1 | O | |
| 403 | —H | —NHCH$_3$ | —H | —H | —H | —H | 1 | O | |
| 404 | —H | —H | —NHCH$_3$ | —H | —H | —H | 1 | O | |
| 405 | —NHC$_2$H$_5$ | —H | —H | —H | —H | —H | 1 | O | |
| 406 | —NHC$_3$H$_7$$^n$ | —H | —H | —H | —H | —H | 1 | O | |
| 407 | —NHCH(CH$_3$)$_2$ | —H | —H | —H | —H | —H | 1 | O | |
| 408 | —NHC$_4$H$_9$$^n$ | —H | —H | —H | —H | —H | 1 | O | A |
| 409 | —NHC$_5$H$_{11}$$^n$ | —H | —H | —H | —H | —H | 1 | O | double |
| 410 | —NHC$_6$H$_{13}$$^n$ | —H | —H | —H | —H | —H | 1 | O | bond |
| 411 | —NHC$_7$H$_{15}$$^n$ | —H | —H | —H | —H | —H | 1 | O | |
| 412 | —N(CH$_3$)$_2$ | —H | —H | —H | —H | —H | 1 | O | |
| 413 | —H | —N(CH$_3$)$_2$ | —H | —H | —H | —H | 1 | O | |
| 414 | —H | —H | —N(CH$_3$)$_2$ | —H | —H | —H | 1 | O | |
| 415 | —NHCOCH$_3$ | —H | —H | —H | —H | —H | 1 | O | |
| 416 | —H | —NHCOCH$_3$ | —H | —H | —H | —H | 1 | O | |
| 417 | —H | —H | —NHCOCH$_3$ | —H | —H | —H | 1 | O | |
| 418 | —NHCOC$_2$H$_5$ | —H | —H | —H | —H | —H | 1 | O | |
| 419 | —NHCOC$_3$H$_7$$^n$ | —H | —H | —H | —H | —H | 1 | O | |
| 420 | —NHCOCH(CH$_3$)$_2$ | —H | —H | —H | —H | —H | 1 | O | |
| 421 | —NHCOC$_4$H$_9$$^n$ | —H | —H | —H | —H | —H | 1 | O | |
| 422 | —NHCOC$_5$H$_{11}$$^n$ | —H | —H | —H | —H | —H | 1 | O | |
| 423 | —NHCOC$_6$H$_{13}$$^n$ | —H | —H | —H | —H | —H | 1 | O | |
| 424 | —NHCOC$_7$H$_{15}$$^n$ | —H | —H | —H | —H | —H | 1 | O | |
| 425 | —NHCOC$_6$H$_5$ | —H | —H | —H | —H | —H | 1 | O | |
| 426 | —H | —NHCOC$_6$H$_5$ | —H | —H | —H | —H | 1 | O | |
| 427 | —H | —H | —NHCOC$_6$H$_5$ | —H | —H | —H | 1 | O | |
| 428 | —CHO | —H | —H | —H | —H | —H | 1 | O | |
| 429 | —H | —CHO | —H | —H | —H | —H | 1 | O | |
| 430 | —H | —H | —CHO | —H | —H | —H | 1 | O | |
| 431 | (1,3-dioxolan-2-yl) | —H | —H | —H | —H | —H | 1 | O | |
| 432 | —H | (1,3-dioxolan-2-yl) | —H | —H | —H | —H | 1 | O | |
| 433 | —H | —H | (1,3-dioxolan-2-yl) | —H | —H | —H | 1 | O | |
| 434 | —CF$_3$ | —H | —H | —H | —H | —H | 1 | O | A |
| 435 | —H | —CF$_3$ | —H | —H | —H | —H | 1 | O | double |
| 436 | —H | —H | —CF$_3$ | —H | —H | —H | 1 | O | bond |
| 437 | —CCl$_3$ | —H | —H | —H | —H | —H | 1 | O | |
| 438 | —H | —CCl$_3$ | —H | —H | —H | —H | 1 | O | |

TABLE 1-continued

| Compound No. | R¹ | R² | R³ | R⁴ | R⁵ | R⁶ | n | X | 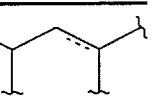 |
|---|---|---|---|---|---|---|---|---|---|
| 439 | —H | —H | —CCl₃ | —H | —H | —H | 1 | O | |
| 440 | —F | —F | —H | —H | —H | —H | 1 | O | |
| 441 | —F | —H | —F | —H | —H | —H | 1 | O | |
| 442 | —F | —H | —H | —F | —H | —H | 1 | O | |
| 443 | —F | —H | —H | —H | —F | —H | 1 | O | |
| 444 | —H | —F | —F | —H | —H | —H | 1 | O | |
| 445 | —H | —F | —H | —F | —H | —H | 1 | O | |
| 446 | —H | —H | —H | —H | —F | —H | 1 | O | |
| 447 | —F | —H | —F | —H | —F | —H | 1 | O | |
| 448 | —F | —F | —F | —F | —F | —H | 1 | O | |
| 449 | —Cl | —Cl | —H | —H | —H | —H | 1 | O | |
| 450 | —Cl | —H | —Cl | —H | —H | —H | 1 | O | |
| 451 | —Cl | —H | —H | —Cl | —H | —H | 1 | O | |
| 452 | —Cl | —H | —H | —H | —Cl | —H | 1 | O | |
| 453 | —H | —Cl | —Cl | —H | —H | —H | 1 | O | |
| 454 | —H | —Cl | —H | —Cl | —H | —H | 1 | O | |
| 455 | —H | —Cl | —H | —Cl | —H | —H | 1 | O | |
| 456 | —Cl | —H | —Cl | —H | —Cl | —H | 1 | O | |
| 457 | —Cl | —Cl | —Cl | —Cl | —Cl | —H | 1 | O | |
| 458 | —CF₃ | —H | —CF₃ | —H | —H | —H | 1 | O | A |
| 459 | —H | —CF₃ | —H | —CF₃ | —H | —H | 1 | O | double |
| 460 | —Cl | —H | —F | —H | —H | —H | 1 | O | bond |
| 461 | —Cl | —H | —H | —H | —F | —H | 1 | O | |
| 462 | —F | —CF₃ | —H | —H | —H | —H | 1 | O | |
| 463 | —F | —H | —CF₃ | —H | —H | —H | 1 | O | |
| 464 | —F | —H | —H | —CF₃ | —H | —H | 1 | O | |
| 465 | —F | —H | —H | —H | —CF₃ | —H | 1 | O | |
| 466 | —H | —F | —CF₃ | —H | —H | —H | 1 | O | |
| 467 | —H | —F | —H | —CF₃ | —H | —H | 1 | O | |
| 468 | —NO₂ | —NO₂ | —H | —H | —H | —H | 1 | O | |
| 469 | —NO₂ | —H | —NO₂ | —H | —H | —H | 1 | O | |
| 470 | —NO₂ | —H | —H | —NO₂ | —H | —H | 1 | O | |
| 471 | —NO₂ | —H | —H | —H | —NO₂ | —H | 1 | O | |
| 472 | —H | —NO₂ | —NO₂ | —H | —H | —H | 1 | O | |
| 473 | —H | —NO₂ | —H | —NO₂ | —H | —H | 1 | O | |
| 474 | —H | —NO₂ | —H | —H | —NO₂ | —H | 1 | O | |
| 475 | —F | —H | —H | —NO₂ | —H | —H | 1 | O | |
| 476 | —H | —NO₂ | —F | —H | —H | —H | 1 | O | |
| 477 | —H | —H | —H | —H | —H | — | 0 | S | |
| 478 | —H | —H | —H | —H | —H | —H | 1 | S | |
| 479 | —H | —H | —H | —H | —H | —H | 2 | S | |
| 480 | —H | —H | —H | —H | —H | —H | 3 | S | A |
| 481 | —F | —H | —H | —H | —H | —H | 1 | S | double |
| 482 | —Cl | —H | —H | —H | —H | —H | 1 | S | bond |
| 483 | —Br | —H | —H | —H | —H | —H | 1 | S | |
| 484 | —I | —H | —H | —H | —H | —H | 1 | S | |
| 485 | —CH₃ | —H | —H | —H | —H | —H | 1 | S | |
| 486 | —C₂H₅ | —H | —H | —H | —H | —H | 1 | S | |
| 487 | —C₃H₇ⁿ | —H | —H | —H | —H | —H | 1 | S | |
| 488 | —CH(CH₃)₂ | —H | —H | —H | —H | —H | 1 | S | |
| 489 | —C₄H₉ⁿ | —H | —H | —H | —H | —H | 1 | S | |
| 490 | —C₅H₁₁ⁿ | —H | —H | —H | —H | —H | 1 | S | |
| 491 | —C₆H₁₃ⁿ | —H | —H | —H | —H | —H | 1 | S | |
| 492 | —C₇H₁₅ⁿ | —H | —H | —H | —H | —H | 1 | S | |
| 493 | —OCH₃ | —H | —H | —H | —H | —H | 1 | S | |
| 494 | —OC₂H₅ | —H | —H | —H | —H | —H | 1 | S | |
| 495 | —OC₃H₇ⁿ | —H | —H | —H | —H | —H | 1 | S | |
| 496 | —OCH(CH₃)₂ | —H | —H | —H | —H | —H | 1 | S | |
| 497 | —OC₄H₉ⁿ | —H | —H | —H | —H | —H | 1 | S | |
| 498 | —OC₅H₁₁ⁿ | —H | —H | —H | —H | —H | 1 | S | |
| 499 | —OC₆H₁₃ⁿ | —H | —H | —H | —H | —H | 1 | S | |
| 500 | —OC₇H₁₅ⁿ | —H | —H | —H | —H | —H | 1 | S | |
| 501 | —OCOCH₃ | —H | —H | —H | —H | —H | 1 | S | A |
| 502 | —OCOC₂H₅ | —H | —H | —H | —H | —H | 1 | S | double |
| 503 | —OCOC₃H₇ⁿ | —H | —H | —H | —H | —H | 1 | S | bond |
| 504 | —OCOCH(CH₃)₂ | —H | —H | —H | —H | —H | 1 | S | |
| 505 | —OCOC₄H₉ⁿ | —H | —H | —H | —H | —H | 1 | S | |
| 506 | —OCOC₅H₁₁ⁿ | —H | —H | —H | —H | —H | 1 | S | |
| 507 | —OCOC₆H₁₃ⁿ | —H | —H | —H | —H | —H | 1 | S | |
| 508 | —OCOC₇H₁₅ⁿ | —H | —H | —H | —H | —H | 1 | S | |
| 509 | —OCOC₆H₅ | —H | —H | —H | —H | —H | 1 | S | |
| 510 | —CN | —H | —H | —H | —H | —H | 1 | S | |
| 511 | —NO₂ | —H | —H | —H | —H | —H | 1 | S | |
| 512 | —COOH | —H | —H | —H | —H | —H | 1 | S | |

TABLE 1-continued

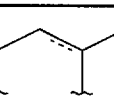

| Compound No. | R¹ | R² | R³ | R⁴ | R⁵ | R⁶ | n | X | |
|---|---|---|---|---|---|---|---|---|---|
| 513 | $-COOCH_3$ | $-H$ | $-H$ | $-H$ | $-H$ | $-H$ | 1 | S | |
| 514 | $-COOC_2H_5$ | $-H$ | $-H$ | $-H$ | $-H$ | $-H$ | 1 | S | |
| 515 | $-COOC_3H_7{}^n$ | $-H$ | $-H$ | $-H$ | $-H$ | $-H$ | 1 | S | |
| 516 | $-COOCH(CH_3)_2$ | $-H$ | $-H$ | $-H$ | $-H$ | $-H$ | 1 | S | |
| 517 | $-COOC_4H_9{}^n$ | $-H$ | $-H$ | $-H$ | $-H$ | $-H$ | 1 | S | |
| 518 | $-COOC_5H_{11}{}^n$ | $-H$ | $-H$ | $-H$ | $-H$ | $-H$ | 1 | S | |
| 519 | $-COOC_6H_{13}{}^n$ | $-H$ | $-H$ | $-H$ | $-H$ | $-H$ | 1 | S | |
| 520 | $-COOC_7H_{15}{}^n$ | $-H$ | $-H$ | $-H$ | $-H$ | $-H$ | 1 | S | |
| 521 | $-CONH_2$ | $-H$ | $-H$ | $-H$ | $-H$ | $-H$ | 1 | S | |
| 522 | $-CONHCH_3$ | $-H$ | $-H$ | $-H$ | $-H$ | $-H$ | 1 | S | |
| 523 | $-CONHC_2H_5$ | $-H$ | $-H$ | $-H$ | $-H$ | $-H$ | 1 | S | |
| 524 | $-CONHC_3H_7{}^n$ | $-H$ | $-H$ | $-H$ | $-H$ | $-H$ | 1 | S | |
| 525 | $-CONHC_4H_9{}^n$ | $-H$ | $-H$ | $-H$ | $-H$ | $-H$ | 1 | S | A |
| 526 | $-CONHC_5H_{11}{}^n$ | $-H$ | $-H$ | $-H$ | $-H$ | $-H$ | 1 | S | double |
| 527 | $-CONHC_6H_{13}{}^n$ | $-H$ | $-H$ | $-H$ | $-H$ | $-H$ | 1 | S | bond |
| 528 | $-CONHC_7H_{15}{}^n$ | $-H$ | $-H$ | $-H$ | $-H$ | $-H$ | 1 | S | |
| 529 | $-CONHC_6H_5$ | $-H$ | $-H$ | $-H$ | $-H$ | $-H$ | 1 | S | |
| 530 | $-CON(CH_3)_2$ | $-H$ | $-H$ | $-H$ | $-H$ | $-H$ | 1 | S | |
| 531 | $-NH_2$ | $-H$ | $-H$ | $-H$ | $-H$ | $-H$ | 1 | S | |
| 532 | $-NHCH_3$ | $-H$ | $-H$ | $-H$ | $-H$ | $-H$ | 1 | S | |
| 533 | $-NHC_2H_5$ | $-H$ | $-H$ | $-H$ | $-H$ | $-H$ | 1 | S | |
| 534 | $-NHC_3H_7{}^n$ | $-H$ | $-H$ | $-H$ | $-H$ | $-H$ | 1 | S | |
| 535 | $-NHC_4H_9{}^n$ | $-H$ | $-H$ | $-H$ | $-H$ | $-H$ | 1 | S | |
| 536 | $-NHC_5H_{11}{}^n$ | $-H$ | $-H$ | $-H$ | $-H$ | $-H$ | 1 | S | |
| 537 | $-NHC_6H_{13}{}^n$ | $-H$ | $-H$ | $-H$ | $-H$ | $-H$ | 1 | S | |
| 538 | $-NHC_7H_{15}{}^n$ | $-H$ | $-H$ | $-H$ | $-H$ | $-H$ | 1 | S | |
| 539 | $-N(CH_3)_2$ | $-H$ | $-H$ | $-H$ | $-H$ | $-H$ | 1 | S | |
| 540 | $-NHCOCH_3$ | $-H$ | $-H$ | $-H$ | $-H$ | $-H$ | 1 | S | |
| 541 | $-NHCOC_2H_5$ | $-H$ | $-H$ | $-H$ | $-H$ | $-H$ | 1 | S | |
| 542 | $-NHCOC_3H_7{}^n$ | $-H$ | $-H$ | $-H$ | $-H$ | $-H$ | 1 | S | |
| 543 | $-NHCOC_4H_9{}^n$ | $-H$ | $-H$ | $-H$ | $-H$ | $-H$ | 1 | S | |
| 544 | $-NHCOC_5H_{11}{}^n$ | $-H$ | $-H$ | $-H$ | $-H$ | $-H$ | 1 | S | |
| 545 | $-NHCOC_6H_{13}{}^n$ | $-H$ | $-H$ | $-H$ | $-H$ | $-H$ | 1 | S | |
| 546 | $-NHCOC_7H_{15}{}^n$ | $-H$ | $-H$ | $-H$ | $-H$ | $-H$ | 1 | S | |
| 547 | $-NHCOC_6H_5$ | $-H$ | $-H$ | $-H$ | $-H$ | $-H$ | 1 | S | |
| 548 | $-CHO$ | $-H$ | $-H$ | $-H$ | $-H$ | $-H$ | 1 | S | |
| 549 | (1,3-dioxolan-2-yl) | $-H$ | $-H$ | $-H$ | $-H$ | $-H$ | 1 | S | |
| 550 | $-CF_3$ | $-H$ | $-H$ | $-H$ | $-H$ | $-H$ | 1 | S | |
| 551 | $-CCl_3$ | $-H$ | $-H$ | $-H$ | $-H$ | $-H$ | 1 | S | |
| 552 | $-F$ | $-F$ | $-H$ | $-H$ | $-H$ | $-H$ | 1 | S | A |
| 553 | $-F$ | $-H$ | $-F$ | $-H$ | $-H$ | $-H$ | 1 | S | double |
| 554 | $-F$ | $-H$ | $-H$ | $-F$ | $-H$ | $-H$ | 1 | S | bond |
| 555 | $-F$ | $-H$ | $-H$ | $-H$ | $-F$ | $-H$ | 1 | S | |
| 556 | $-H$ | $-F$ | $-F$ | $-H$ | $-H$ | $-H$ | 1 | S | |
| 557 | $-H$ | $-F$ | $-H$ | $-F$ | $-H$ | $-H$ | 1 | S | |
| 558 | $-H$ | $-F$ | $-H$ | $-H$ | $-F$ | $-H$ | 1 | S | |
| 559 | $-F$ | $-H$ | $-F$ | $-H$ | $-F$ | $-H$ | 1 | S | |
| 560 | $-F$ | $-F$ | $-F$ | $-F$ | $-F$ | $-H$ | 1 | S | |
| 561 | $-Cl$ | $-Cl$ | $-H$ | $-H$ | $-H$ | $-H$ | 1 | S | |
| 562 | $-Cl$ | $-H$ | $-Cl$ | $-H$ | $-H$ | $-H$ | 1 | S | |
| 563 | $-Cl$ | $-H$ | $-H$ | $-Cl$ | $-H$ | $-H$ | 1 | S | |
| 564 | $-Cl$ | $-H$ | $-H$ | $-H$ | $-Cl$ | $-H$ | 1 | S | |
| 565 | $-H$ | $-Cl$ | $-Cl$ | $-H$ | $-H$ | $-H$ | 1 | S | |
| 566 | $-H$ | $-Cl$ | $-H$ | $-Cl$ | $-H$ | $-H$ | 1 | S | |
| 567 | $-H$ | $-Cl$ | $-H$ | $-H$ | $-Cl$ | $-H$ | 1 | S | |
| 568 | $-Cl$ | $-H$ | $-Cl$ | $-H$ | $-Cl$ | $-H$ | 1 | S | |
| 569 | $-Cl$ | $-Cl$ | $-Cl$ | $-Cl$ | $-Cl$ | $-H$ | 1 | S | |
| 570 | $-CF_3$ | $-H$ | $-CF_3$ | $-H$ | $-H$ | $-H$ | 1 | S | |
| 571 | $-H$ | $-CF_3$ | $-H$ | $-CF_3$ | $-H$ | $-H$ | 1 | S | |
| 572 | $-Cl$ | $-H$ | $-F$ | $-H$ | $-H$ | $-H$ | 1 | S | |
| 573 | $-Cl$ | $-H$ | $-H$ | $-H$ | $-F$ | $-H$ | 1 | S | |
| 574 | $-F$ | $-CF_3$ | $-H$ | $-H$ | $-H$ | $-H$ | 1 | S | |
| 575 | $-F$ | $-H$ | $-CF_3$ | $-H$ | $-H$ | $-H$ | 1 | S | |
| 576 | $-F$ | $-H$ | $-H$ | $-CF_3$ | $-H$ | $-H$ | 1 | S | A |
| 577 | $-F$ | $-H$ | $-H$ | $-H$ | $-CF_3$ | $-H$ | 1 | S | double |
| 578 | $-H$ | $-F$ | $-CF_3$ | $-H$ | $-H$ | $-H$ | 1 | S | bond |
| 579 | $-H$ | $-F$ | $-H$ | $-CF_3$ | $-H$ | $-H$ | 1 | S | |
| 580 | $-NO_2$ | $-NO_2$ | $-H$ | $-H$ | $-H$ | $-H$ | 1 | S | |

TABLE 1-continued

| Compound No. | R¹ | R² | R³ | R⁴ | R⁵ | R⁶ | n | X | |
|---|---|---|---|---|---|---|---|---|---|
| 581 | —NO₂ | —H | —NO₂ | —H | —H | —H | 1 | S | |
| 582 | —NO₂ | —H | —H | —NO₂ | —H | —H | 1 | S | |
| 583 | —NO₂ | —H | —H | —H | —NO₂ | —H | 1 | S | |
| 584 | —H | —NO₂ | —NO₂ | —H | —H | —H | 1 | S | |
| 585 | —H | —NO₂ | —H | —NO₂ | —H | —H | 1 | S | |
| 586 | —H | —NO₂ | —H | —H | —NO₂ | —H | 1 | S | |
| 587 | —F | —H | —H | —NO₂ | —H | —H | 1 | S | |
| 588 | —H | —NO₂ | | —H | —H | —H | 1 | S | |
| 589 | —H | —H | —H | —H | —H | —CH₃ | 1 | O | |
| 590 | —H | —H | —H | —H | —H | —C₂H₅ | 1 | O | |
| 591 | —H | —H | —H | —H | —H | —C₆H₅ | 1 | O | |
| 592 | —F | —H | —H | —H | —H | —CH₃ | 1 | O | |
| 593 | —F | —H | —H | —H | —H | —C₆H₅ | 1 | O | |
| 594 | —H | —H | —F | —H | —H | —CH₃ | 1 | O | A single bond |
| 595 | —H | —H | —F | —H | —H | —C₆H₅ | 1 | O | |
| 596 | —Cl | —H | —H | —H | —H | —CH₃ | 1 | O | |
| 597 | —Cl | —H | —H | —H | —H | —C₆H₅ | 1 | O | |
| 598 | —H | —H | —Cl | —H | —H | —CH₃ | 1 | O | |
| 599 | —H | —H | —Cl | —H | —H | —C₆H₅ | 1 | O | |
| 600 | —H | —H | —F | —H | —H | —C₆H₄ (4-F) | 1 | O | |
| 601 | —H | —H | —Cl | —H | —H | —C₆H₄ (4-Cl) | 1 | O | |
| 602 | —H | —H | —H | —H | —H | —CH₃ | 1 | O | |
| 603 | —H | —H | —H | —H | —H | —C₂H₅ | 1 | O | |
| 604 | —H | —H | —H | —H | —H | —C₆H₅ | 1 | O | |
| 605 | —F | —H | —H | —H | —H | —CH₃ | 1 | O | |
| 606 | —F | —H | —H | —H | —H | —C₂H₅ | 1 | O | A double bond |
| 607 | —H | —H | —F | —H | —H | —CH₃ | 1 | O | |
| 608 | —H | —H | —F | —H | —H | —C₂H₅ | 1 | O | |
| 609 | —Cl | —H | —H | —H | —H | —CH₃ | 1 | O | |
| 610 | —Cl | —H | —H | —H | —H | —C₂H₅ | 1 | O | |
| 611 | —H | —H | —Cl | —H | —H | —CH₃ | 1 | O | |
| 612 | —H | —H | —Cl | —H | —H | —C₂H₅ | 1 | O | |
| 613 | —H | —H | —F | —H | —H | —C₆H₄ (4-F) | 1 | O | |
| 614 | —H | —H | —Cl | —H | —H | —C₆H₄ (4-Cl) | 1 | O | |

TABLE 2

| Compound No. | R¹ | R² | R³ | R⁴ | R⁵ | R⁶ | n | X | |
|---|---|---|---|---|---|---|---|---|---|
| 615 | —H | —H | —H | —H | —H | — | 0 | O | |
| 616 | —H | —H | —H | —H | —H | —H | 1 | O | |
| 617 | —H | —H | —H | —H | —H | —H | 2 | O | |
| 618 | —H | —H | —H | —H | —H | —H | 3 | O | |
| 619 | —F | —H | —H | —H | —H | —H | 1 | O | |
| 620 | —H | —H | —H | —F | —H | —H | 1 | O | |
| 621 | —Cl | —H | —H | —H | —H | —H | 1 | O | |
| 622 | —H | —H | —Cl | —H | —H | —H | 1 | O | |
| 623 | —Br | —H | —H | —H | —H | —H | 1 | O | |
| 624 | —H | —H | —Br | —H | —H | —H | 1 | O | |
| 625 | —CH₃ | —H | —H | —H | —H | —H | 1 | O | A single bond |
| 626 | —H | —H | —CH₃ | —H | —H | —H | 1 | O | |
| 627 | —OCH₃ | —H | —H | —H | —H | —H | 1 | O | |
| 628 | —H | —H | —OCH₃ | —H | —H | —H | 1 | O | |
| 629 | —OCOCH₃ | —H | —H | —H | —H | —H | 1 | O | |
| 630 | —H | —H | —OCOCH₃ | —H | —H | —H | 1 | O | |
| 631 | —CN | —H | —H | —H | —H | —H | 1 | O | |
| 632 | —H | —H | —CN | —H | —H | —H | 1 | O | |
| 633 | —NO₂ | —H | —H | —H | —H | —H | 1 | O | |
| 634 | —H | —H | —NO₂ | —H | —H | —H | 1 | O | |
| 635 | —COOH | —H | —H | —H | —H | —H | 1 | O | |
| 636 | —H | —H | —COOH | —H | —H | —H | 1 | O | |
| 637 | —COOCH₃ | —H | —H | —H | —H | —H | 1 | O | |
| 638 | —H | —H | —COOCH₃ | —H | —H | —H | 1 | O | |
| 639 | —CONH₂ | —H | —H | —H | —H | —H | 1 | O | |
| 640 | —H | —H | —CONH₂ | —H | —H | —H | 1 | O | |
| 641 | —CONHCH₃ | —H | —H | —H | —H | —H | 1 | O | |
| 642 | —H | —H | —CONHCH₃ | —H | —H | —H | 1 | O | |
| 643 | —NH₂ | —H | —H | —H | —H | —H | 1 | O | |
| 644 | —H | —H | —NH₂ | —H | —H | —H | 1 | O | |
| 645 | —NHCH₃ | —H | —H | —H | —H | —H | 1 | O | |

TABLE 2-continued

| Compound No. | R¹ | R² | R³ | R⁴ | R⁵ | R⁶ | n | X | |
|---|---|---|---|---|---|---|---|---|---|
| 646 | −H | −H | −NHCH₃ | −H | −H | −H | 1 | O | |
| 647 | −NHCOCH₃ | −H | −H | −H | −H | −H | 1 | O | |
| 648 | −H | −H | −NHCOCH₃ | −H | −H | −H | 1 | O | |
| 649 | −CHO | −H | −H | −H | −H | −H | 1 | O | |
| 650 | −H | −H | −CHO | −H | −H | −H | 1 | O | A |
| 651 | −CF₃ | −H | −H | −H | −H | −H | 1 | O | single |
| 652 | −H | −H | −CF₃ | −H | −H | −H | 1 | O | bond |
| 653 | −CCl₃ | −H | −H | −H | −H | −H | 1 | O | |
| 654 | −H | −H | −CCl₃ | −H | −H | −H | 1 | O | |
| 655 | −F | −H | −F | −H | −H | −H | 1 | O | |
| 656 | −F | −H | −H | −H | −F | −H | 1 | O | |
| 657 | −F | −H | −F | −H | −F | −H | 1 | O | |
| 658 | −F | −F | −F | −F | −F | −H | 1 | O | |
| 659 | −Cl | −H | −Cl | −H | −H | −H | 1 | O | |
| 660 | −Cl | −H | −H | −H | −Cl | −H | 1 | O | |
| 661 | −Cl | −H | −Cl | −H | −Cl | −H | 1 | O | |
| 662 | −Cl | −Cl | −Cl | −Cl | −Cl | −H | 1 | O | |
| 663 | −CF₃ | −H | −CF₃ | −H | −H | −H | 1 | O | |
| 664 | −Cl | −H | −F | −H | −H | −H | 1 | O | |
| 665 | −Cl | −H | −H | −H | −F | −H | 1 | O | |
| 666 | −F | −H | −H | −H | −CF₃ | −H | 1 | O | |
| 667 | −H | −H | −H | −H | −H | — | 0 | O | |
| 668 | −H | −H | −H | −H | −H | −H | 1 | O | |
| 669 | −H | −H | −H | −H | −H | −H | 2 | O | |
| 670 | −H | −H | −H | −H | −H | −H | 3 | O | |
| 671 | −F | −H | −H | −H | −H | −H | 1 | O | |
| 672 | −H | −H | −F | −H | −H | −H | 1 | O | |
| 673 | −Cl | −H | −H | −H | −H | −H | 1 | O | |
| 674 | −H | −H | −Cl | −H | −H | −H | 1 | O | |
| 675 | −Br | −H | −H | −H | −H | −H | 1 | O | |
| 676 | −H | −H | −Br | −H | −H | −H | 1 | O | |
| 677 | −CH₃ | −H | −H | −H | −H | −H | 1 | O | |
| 678 | −H | −H | −CH₃ | −H | −H | −H | 1 | O | A |
| 679 | −OCH₃ | −H | −H | −H | −H | −H | 1 | O | double |
| 680 | −H | −H | −OCH₃ | −H | −H | −H | 1 | O | bond |
| 681 | −OCOCH₃ | −H | −H | −H | −H | −H | 1 | O | |
| 682 | −H | −H | −OCOCH₃ | −H | −H | −H | 1 | O | |
| 683 | −CN | −H | −H | −H | −H | −H | 1 | O | |
| 684 | −H | −H | −CN | −H | −H | −H | 1 | O | |
| 685 | −NO₂ | −H | −H | −H | −H | −H | 1 | O | |
| 686 | −H | −H | −NO₂ | −H | −H | −H | 1 | O | |
| 687 | −COOH | −H | −H | −H | −H | −H | 1 | O | |
| 688 | −H | −H | −COOH | −H | −H | −H | 1 | O | |
| 689 | −COOCH₃ | −H | −H | −H | −H | −H | 1 | O | |
| 690 | −H | −H | −COOCH₃ | −H | −H | −H | 1 | O | |
| 691 | −CONH₂ | −H | −H | −H | −H | −H | 1 | O | |
| 692 | −H | −H | −CONH₂ | −H | −H | −H | 1 | O | |
| 693 | −CONHCH₃ | −H | −H | −H | −H | −H | 1 | O | |
| 694 | −H | −H | −CONHCH₃ | −H | −H | −H | 1 | O | |
| 695 | −NH₂ | −H | −H | −H | −H | −H | 1 | O | |
| 696 | −H | −H | −NH₂ | −H | −H | −H | 1 | O | |
| 697 | −NHCH₃ | −H | −H | −H | −H | −H | 1 | O | |
| 698 | −H | −H | −NHCH₃ | −H | −H | −H | 1 | O | |
| 699 | −NHCOCH₃ | −H | −H | −H | −H | −H | 1 | O | |
| 700 | −H | −H | −NHCOCH₃ | −H | −H | −H | 1 | O | |
| 701 | −CHO | −H | −H | −H | −H | −H | 1 | O | |
| 702 | −H | −H | −CHO | −H | −H | −H | 1 | O | |
| 703 | −CF₃ | −H | −H | −H | −H | −H | 1 | O | A |
| 704 | −H | −H | −CF₃ | −H | −H | −H | 1 | O | double |
| 705 | −CCl₃ | −H | −H | −H | −H | −H | 1 | O | bond |
| 706 | −H | −H | −CCl₃ | −H | −H | −H | 1 | O | |
| 707 | −F | −H | −F | −H | −H | −H | 1 | O | |
| 708 | −F | −H | −H | −H | −F | −H | 1 | O | |
| 709 | −F | −H | −F | −H | −F | −H | 1 | O | |
| 710 | −F | −F | −F | −F | −F | −H | 1 | O | |
| 711 | −Cl | −H | −Cl | −H | −H | −H | 1 | O | |
| 712 | −Cl | −H | −H | −H | −Cl | −H | 1 | O | |
| 713 | −Cl | −H | −Cl | −H | −Cl | −H | 1 | O | |
| 714 | −Cl | −Cl | −Cl | −Cl | −Cl | −H | 1 | O | |
| 715 | CF₃ | −H | −CF₃ | −H | −H | −H | 1 | O | |
| 716 | −Cl | −H | −F | −H | −H | −H | 1 | O | |
| 717 | −Cl | −H | −H | −H | −F | −H | 1 | O | |
| 718 | −F | −H | −H | −H | −CF₃ | −H | 1 | O | |

TABLE 3

| Compound No. | R¹ | R² | R³ | R⁴ | R⁵ | R⁶ | n | X | A |
|---|---|---|---|---|---|---|---|---|---|
| 719 | −H | −H | −H | −H | −H | — | 0 | O | |
| 720 | −H | −H | −H | −H | −H | −H | 1 | O | |
| 721 | −H | −H | −H | −H | −H | −H | 2 | O | |
| 722 | −H | −H | −H | −H | −H | −H | 3 | O | |
| 723 | −F | −H | −H | −H | −H | −H | 1 | O | |
| 724 | −H | −H | −F | −H | −H | −H | 1 | O | |
| 725 | −Cl | −H | −H | −H | −H | −H | 1 | O | |
| 726 | −H | −H | −Cl | −H | −H | −H | 1 | O | |
| 727 | −Br | −H | −H | −H | −H | −H | 1 | O | |
| 728 | −H | −H | −Br | −H | −H | −H | 1 | O | |
| 729 | −CH₃ | −H | −H | −H | −H | −H | 1 | O | |
| 730 | −H | −H | −CH₃ | −H | −H | −H | 1 | O | A single bond |
| 731 | −OCH₃ | −H | −H | −H | −H | −H | 1 | O | |
| 732 | −H | −H | −OCH₃ | −H | −H | −H | 1 | O | |
| 733 | −OCOCH₃ | −H | −H | −H | −H | −H | 1 | O | |
| 734 | −H | −H | −OCOCH₃ | −H | −H | −H | 1 | O | |
| 735 | −CN | −H | −H | −H | −H | −H | 1 | O | |
| 736 | −H | −H | −CN | −H | −H | −H | 1 | O | |
| 737 | −NO₂ | −H | −H | −H | −H | −H | 1 | O | |
| 738 | −H | −H | −NO₂ | −H | −H | −H | 1 | O | |
| 739 | −COOH | −H | −H | −H | −H | −H | 1 | O | |
| 740 | −H | −H | −COOH | −H | −H | −H | 1 | O | |
| 741 | −COOCH₃ | −H | −H | −H | −H | −H | 1 | O | |
| 742 | −H | −H | −COOCH₃ | −H | −H | −H | 1 | O | |
| 743 | −CONH₂ | −H | −H | −H | −H | −H | 1 | O | |
| 744 | −H | −H | −CONH₂ | −H | −H | −H | 1 | O | |
| 745 | −CONHCH₃ | −H | −H | −H | −H | −H | 1 | O | |
| 746 | −H | −H | −CONHCH₃ | −H | −H | −H | 1 | O | |
| 747 | −NH₂ | −H | −H | −H | −H | −H | 1 | O | |
| 748 | −H | −H | −NH₂ | −H | −H | −H | 1 | O | |
| 749 | −NHCH₃ | −H | −H | −H | −H | −H | 1 | O | |
| 750 | −H | −H | −NHCH₃ | −H | −H | −H | 1 | O | |
| 751 | −NHCOCH₃ | −H | −H | −H | −H | −H | 1 | O | |
| 752 | −H | −H | −NHCOCH₃ | −H | −H | −H | 1 | O | |
| 753 | −CHO | −H | −H | −H | −H | −H | 1 | O | |
| 754 | −H | −H | −CHO | −H | −H | −H | 1 | O | |
| 755 | −CF₃ | −H | −H | −H | −H | −H | 1 | O | |
| 756 | −H | −H | −CF₃ | −H | −H | −H | 1 | O | |
| 757 | −CCl₃ | −H | −H | −H | −H | −H | 1 | O | |
| 758 | −H | −H | −CCl₃ | −H | −H | −H | 1 | O | |
| 759 | −F | −H | −F | −H | −H | −H | 1 | O | |
| 760 | −F | −H | −H | −H | −F | −H | 1 | O | |
| 761 | −F | −H | −F | −H | −F | −H | 1 | O | |
| 762 | −F | −F | −F | −F | −F | −H | 1 | O | |
| 763 | −Cl | −H | −H | −H | −Cl | −H | 1 | O | |
| 764 | −Cl | −H | −H | −H | −Cl | −H | 1 | O | |
| 765 | −Cl | −H | −Cl | −H | −Cl | −H | 1 | O | |
| 766 | −Cl | −Cl | −Cl | −Cl | −Cl | −H | 1 | O | |
| 767 | −CF₃ | −H | −CF₃ | −H | −H | −H | 1 | O | |
| 768 | −Cl | −H | −F | −H | −H | −H | 1 | O | |
| 769 | −Cl | −H | −H | −H | −F | −H | 1 | O | |
| 770 | −F | −H | −H | −H | −CF₃ | −H | 1 | O | |

TABLE 4

| Compound No. | R¹ | R² | R³ | R⁴ | R⁶ | n | X | A |
|---|---|---|---|---|---|---|---|---|
| 771 | −H | −H | −H | −H | — | 0 | O | |
| 772 | −H | −H | −H | −H | −H | 1 | O | |
| 773 | −H | −H | −H | −H | −H | 2 | O | |
| 774 | −H | −H | −H | −H | −H | 3 | O | |
| 775 | −CH₃ | −H | −H | −H | −H | 1 | O | |
| 776 | −H | −CH₃ | −H | −H | −H | 1 | O | |
| 777 | −H | −H | −CH₃ | −H | −H | 1 | O | |
| 778 | −H | −H | −H | −CH₃ | −H | 1 | O | |
| 779 | −H | −H | −C₂H₅ | −H | −H | 1 | O | |
| 780 | −CH₃ | −H | −H | −H | −H | 2 | O | |
| 781 | −H | −H | −CH₃ | −H | −H | 2 | O | |
| 782 | −H | −H | −H | −CH₃ | −H | 2 | O | A single |
| 783 | −H | −H | −C₂H₅ | −H | −H | 2 | O | |

TABLE 4-continued

| Compound No. | $R^1$ | $R^2$ | $R^3$ | $R^4$ | $R^6$ | n | X | ![chain] |
|---|---|---|---|---|---|---|---|---|
| 784 | —H | —H | —H | —H | — | 0 | S | bond |
| 785 | —H | —H | —H | —H | —H | 1 | S | |
| 786 | —H | —H | —H | —H | —H | 2 | S | |
| 787 | —H | —H | —H | —H | —H | 3 | S | |
| 788 | —CH$_3$ | —H | —H | —H | —H | 1 | S | |
| 789 | —H | —CH$_3$ | —H | —H | —H | 1 | S | |
| 790 | —H | —H | —CH$_3$ | —H | —H | 1 | S | |
| 791 | —H | —H | —H | —CH$_3$ | —H | 1 | S | |
| 792 | —H | —H | —C$_2$H$_5$ | —H | —H | 1 | S | |
| 793 | —CH$_3$ | —H | —H | —H | —H | 2 | S | |
| 794 | —H | —H | —CH$_3$ | —H | —H | 2 | S | |
| 795 | —H | —H | —H | —CH$_3$ | —H | 2 | S | |
| 796 | —H | —H | —C$_2$H$_5$ | —H | —H | 2 | S | |
| 797 | —H | —H | —H | —H | — | 0 | O | |
| 798 | —H | —H | —H | —H | —H | 1 | O | |
| 799 | —H | —H | —H | —H | —H | 2 | O | |
| 800 | —H | —H | —H | —H | —H | 3 | O | |
| 801 | —CH$_3$ | —H | —H | —H | —H | 1 | O | |
| 802 | —H | —CH$_3$ | —H | —H | —H | 1 | O | |
| 803 | —H | —H | —CH$_3$ | —H | —H | 1 | O | |
| 804 | —H | —H | —H | —CH$_3$ | —H | 1 | O | |
| 805 | —H | —H | —C$_2$H$_5$ | —H | —H | 1 | O | |
| 806 | —CH$_3$ | —H | —H | —H | —H | 2 | O | |
| 807 | —H | —H | —CH$_3$ | —H | —H | 2 | O | |
| 808 | —H | —H | —H | —CH$_3$ | —H | 2 | O | A |
| 809 | —H | —H | —C$_2$H$_5$ | —H | —H | 2 | O | double |
| 810 | —H | —H | —H | —H | — | 0 | S | bond |
| 811 | —H | —H | —H | —H | —H | 1 | S | |
| 812 | —H | —H | —H | —H | —H | 2 | S | |
| 813 | —H | —H | —H | —H | —H | 3 | S | |
| 814 | —CH$_3$ | —H | —H | —H | —H | 1 | S | |
| 815 | —H | —CH$_3$ | —H | —H | —H | 1 | S | |
| 816 | —H | —H | —CH$_3$ | —H | —H | 1 | S | |
| 817 | —H | —H | —H | —CH$_3$ | —H | 1 | S | |
| 818 | —H | —H | —C$_2$H$_5$ | —H | —H | 1 | S | |
| 819 | —CH$_3$ | —H | —H | —H | —H | 2 | S | |
| 820 | —H | —H | —CH$_3$ | —H | —H | 2 | S | |
| 821 | —H | —H | —H | —CH$_3$ | —H | 2 | S | |
| 822 | —H | —H | —C$_2$H$_5$ | —H | —H | 2 | S | |

<2> The method of preparing the compounds of the present invention

The method of preparing the compounds of the present invention is explained for three cases classified depending on the kinds of the group represented by a ring A.

(1) The case wherein the ring A is 2,4-thiazolidinedione

The compound represented by the above formula (I) wherein the ring A is 2,4-thiazolidinedione can be prepared with the following five kinds of synthetic methods.

(Synthetic method-1)

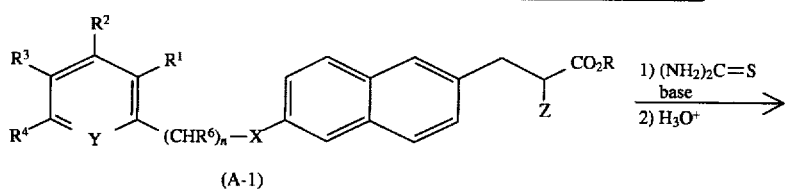

(A-1)

-continued
(Synthetic method-1)

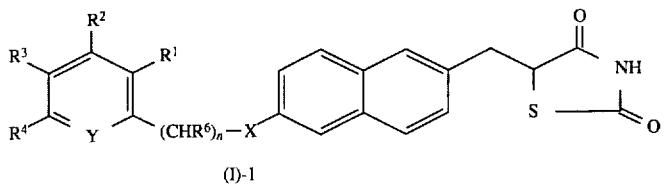

(I)-1

In the above formulae, X, Y, n, $R^1$, $R^2$, $R^3$, $R^4$ and $R^6$ are as defined above; Z represents halogen atom such as fluorine, chlorine, bromine, iodine or the like; and R represents a lower alkyl such as methyl, ethyl or the like.

In the reaction of the conversion of compound (A-1) into compound (I)-1, compound (A-1) is first reacted with thiourea in the presence of a base to form a 2-imino-4-thiazolidinone ring. At this time, sodium acetate, potassium acetate, sodium carbonate, potassium carbonate or the like can be used as a base, and an alcohol such as methanol, ethanol, propanol, methoxyethanol, ethoxyethanol or the like, dimethylsulfoxide (DMSO), dimethylformamide (DMF) or the like can be used as a solvent. Then, the 2-imino-4-thiazolidinone ring may be converted to a 4-thiazolidinedione ring by hydrolysis under acidic conditions to obtain compound (I)-1.

the like; and M represents a metal such as Li, Na, K, Mg or the like.

The reaction for the conversion of compound (B-1) to compound (I)-1 is carried out by reacting the former compound with a metal salt of a dianion of 2,4-thiazolidinone. As a metal salt, a salt of an alkali metal such as lithium, sodium, potassium or the like, or an alkaline earth metal such as magnesium or the like can be used. The solvents to be used include an inert solvent such as diethyl ether, tetrahydrofuran (THF), dioxane, dimethoxymethane or the like.

(Synthetic method-2)

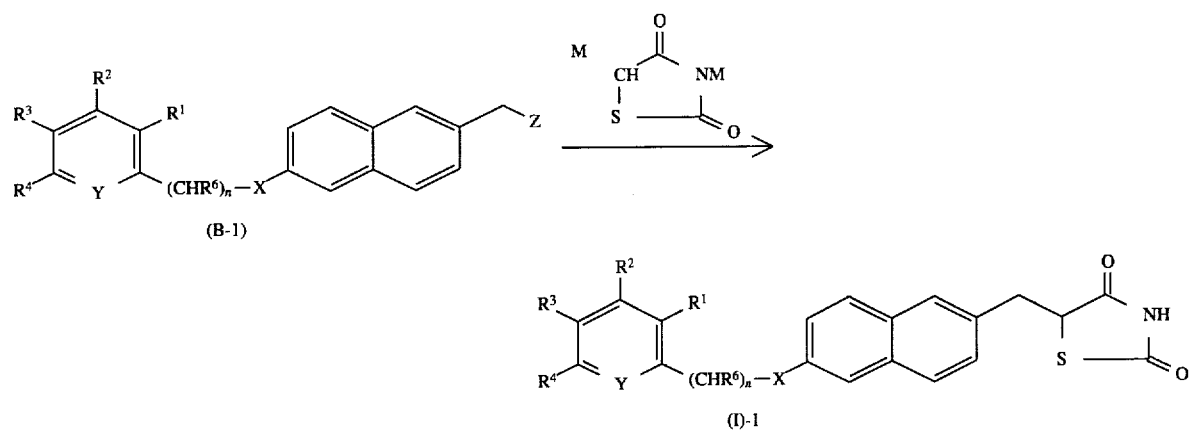

In the above formulae, X, Y, n, $R^1$, $R^2$, $R^3$, $R^4$ and $R^6$ are as defined above; Z represents a leaving group such as chlorine, bromine, iodine, $OSO_2CH_3$, $OSO_2C_6H_5(P\text{-}CH_3)$ or (Synthetic method-3)

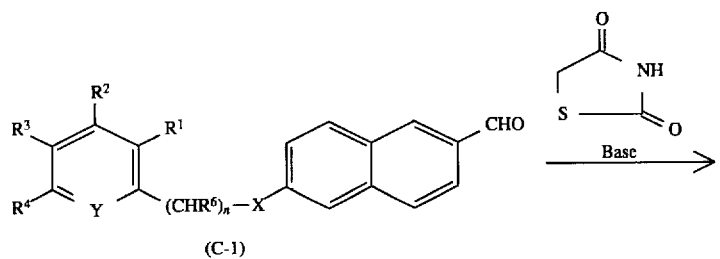

(Synthetic method-3)

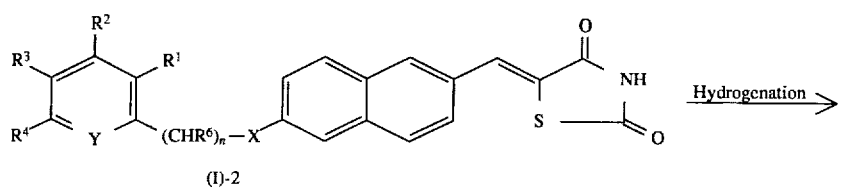

(I)-2

Hydrogenation →

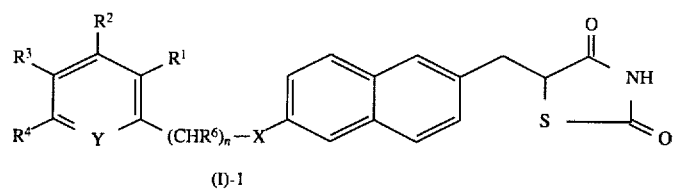

(I)-1

In the above formulae, X, Y, n, $R^1$, $R^2$, $R^3$, $R^4$ and $R^6$ are as defined above.

Compound (I)-2 can be obtained by condensing compound (C-1) with 2,4-thiazolidinone in the presence of a base under dehydration. In this case, as a base, an inorganic base such as sodium hydroxide, potassium hydroxide, sodium carbonate, potassium carbonate, sodium acetate, potassium acetate or the like, or an amine such as triethylamine, pyridine, piperidine, pyrrolidine, N-methylpiperidine, N-methylmorpholine or the like can be used, and as a solvent, an alcohol such as methanol, ethanol, 1-propanol, 2-propanol or the like can be used. Sometimes the reaction can be conducted without a solvent.

Compound (I)-1 can be synthesized by catalytically hydrogenating compound (I)-2 under hydrogen or in the presence of cyclohexene using as a catalyst a transition metal catalyst such as palladium, platinum, rhodium or the like, or a carrier holding it. At that time, as a solvent, an alcohol such as methanol, ethanol, 1-propanol, 2-propanol or the like, THF, dioxane, acetic acid or the like can be used.

Compound (I)-1 or (I)-2 wherein the dotted line in compound (I)-1 does not represent a bond and the dotted line in compound (I)-2 represents a bond can be synthesized by reacting compound (D-1) or (E-1) wherein the dotted line in compound (D-1) does not represent a bond and the dotted line in compound (E-1) represents a bond, respectively with alcohol compound (D-2) at the presence of triphenylphosphine and diethyl azodicarboxylate. At this time, as a solvent, toluene, THF, diethyl ether or dioxane can be used.

(Synthetic method-4)

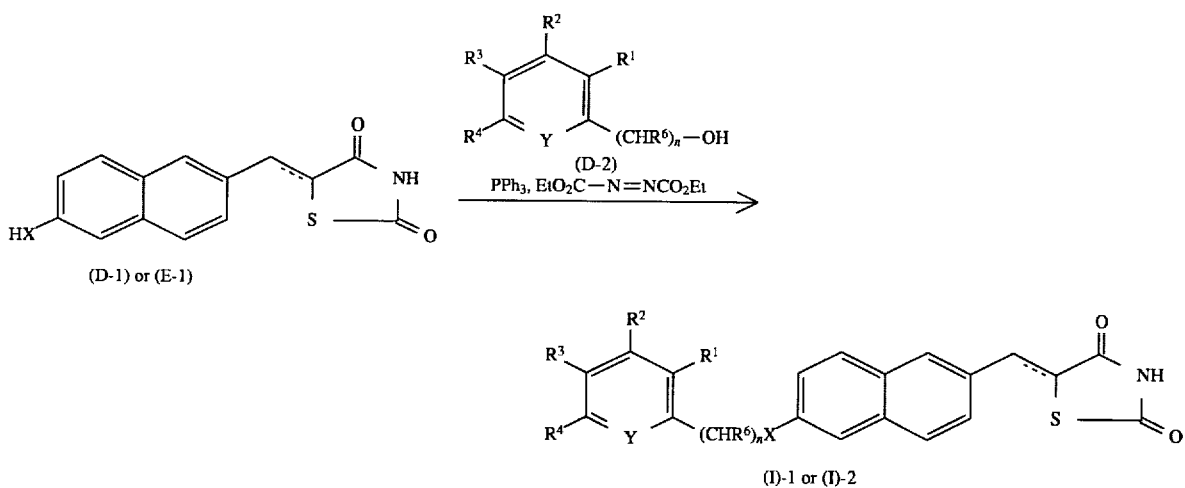

In the above formulae, X, Y, $R^1$, $R^2$, $R^3$, $R^4$, $R^6$, n and dotted lines are as defined above.

(Synthetic method-5)

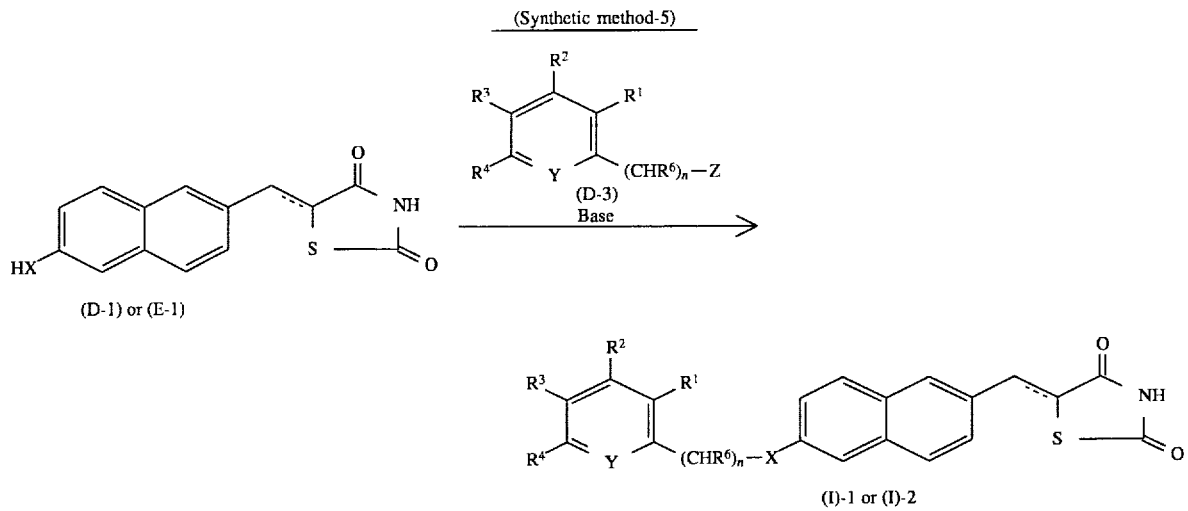

In the above formulae, X, Y, $R^1$, $R^2$, $R^3$, $R^4$, $R^6$, n, Z and dotted lines are as defined above.

Compound (I)-1 or (I)-2 can be synthesized by reacting compound (D-1) or (E-1) respectively with halide (D-3) in the presence of a base. At this time, sodium hydride, potassium hydride, potassium carbonate, potassium carbonate, sodium carbonate or the like is used as a base, and THF, dioxane, diethyl ether, DMF, DMSO, N-methylpyrrolidone or the like is used as a solvent.

(2) The case wherein the ring A is rhodanine

The compound represented by the above formula (I) wherein the group A is rhodanine can be prepared by the following two kinds of synthetic methods.

(Synthetic method-6)

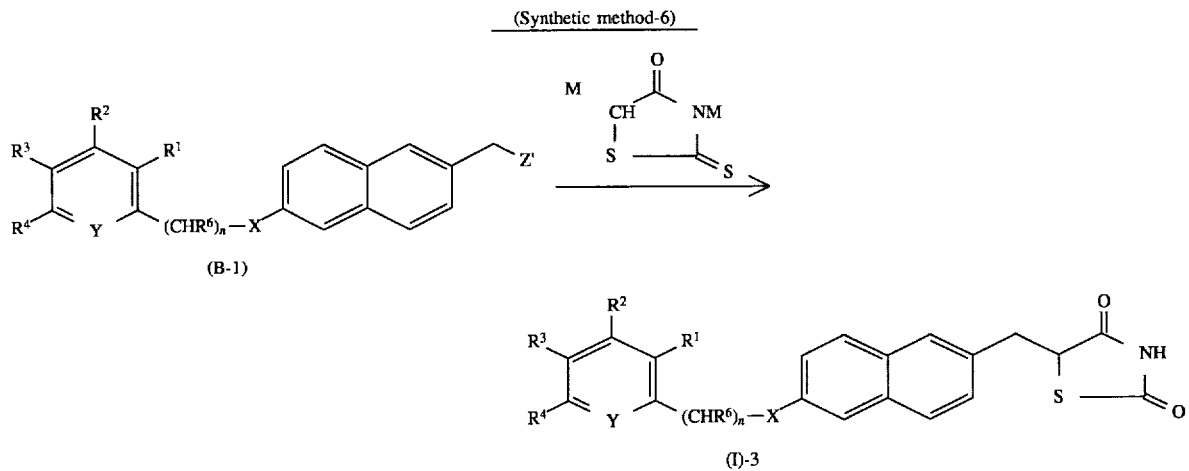

In the above formulae, X, Y, n, $R^1$, $R^2$, $R^3$, $R^4$, $R^6$, Z' and M are as defined above.

The reaction for the conversion of compound (B-1) into compound (I)-3 is performed by reacting compound (B-1) with a metal salt of a dianion of rhodanine. Solvents used include inert solvents such as diethyl ether, THF, dioxane, dimethoxymethane and the like.

(Synthetic method-7)

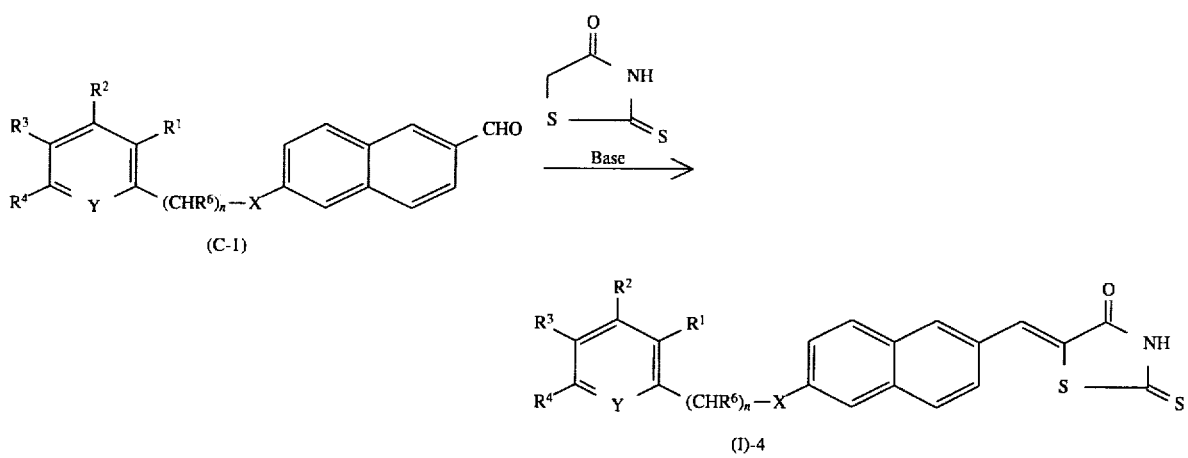

In the above formulae, X, Y, n, $R^1$, $R^2$, $R^3$, $R^4$, and $R^6$ are as defined above.

The reaction for the conversion of compound (C-1) into compound (I)-4 is carried out by condensing compound (C-1) with rhodanine with dehydrating in the presence of a base. Bases used include inorganic bases such as sodium hydroxide, potassium hydroxide, sodium carbonate, potassium carbonate, sodium acetate, potassium acetate and the like, and amines such as triethylamine, pyridine, piperidine, pyrrolidine, N-methylpiperidine, N-methylmorpholine and the like. Solvents used include alcohols such as methanol, ethanol, 1-propanol, 2-propanol and the like. Sometimes the reaction can also be conducted without a solvent.

(3) The case wherein the ring A is 5-tetrazole

The compound represented by the above formula I wherein the group A is 5-tetrazole can be prepared by the following synthetic method.

The reaction for the conversion of the compound (F-1) into compound (I)-5 can be carried out by reacting compound (F-1) with sodium azide and ammonium chloride. At this time, polar solvents such as DMF, DMSO and the like can be used.

<3> Methods of preparation of starting materials and intermediates in the preparation of the compounds of the present invention The starting material (A-1) in-Synthetic method-1 described above can be prepared for example by the following synthetic method.

(Synthetic method-8)

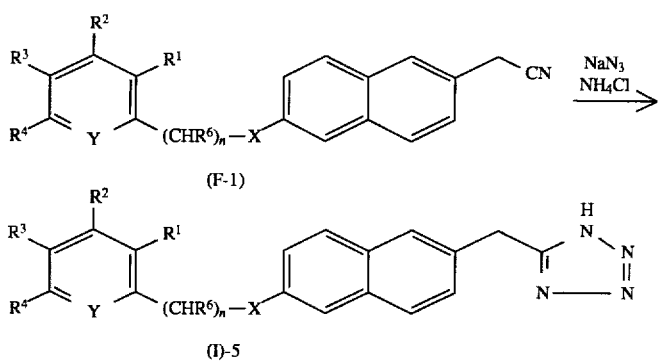

In the above formulae, X, Y, n, $R^1$, $R^2$, $R^3$, $R^4$, and $R^6$ are as defined above.

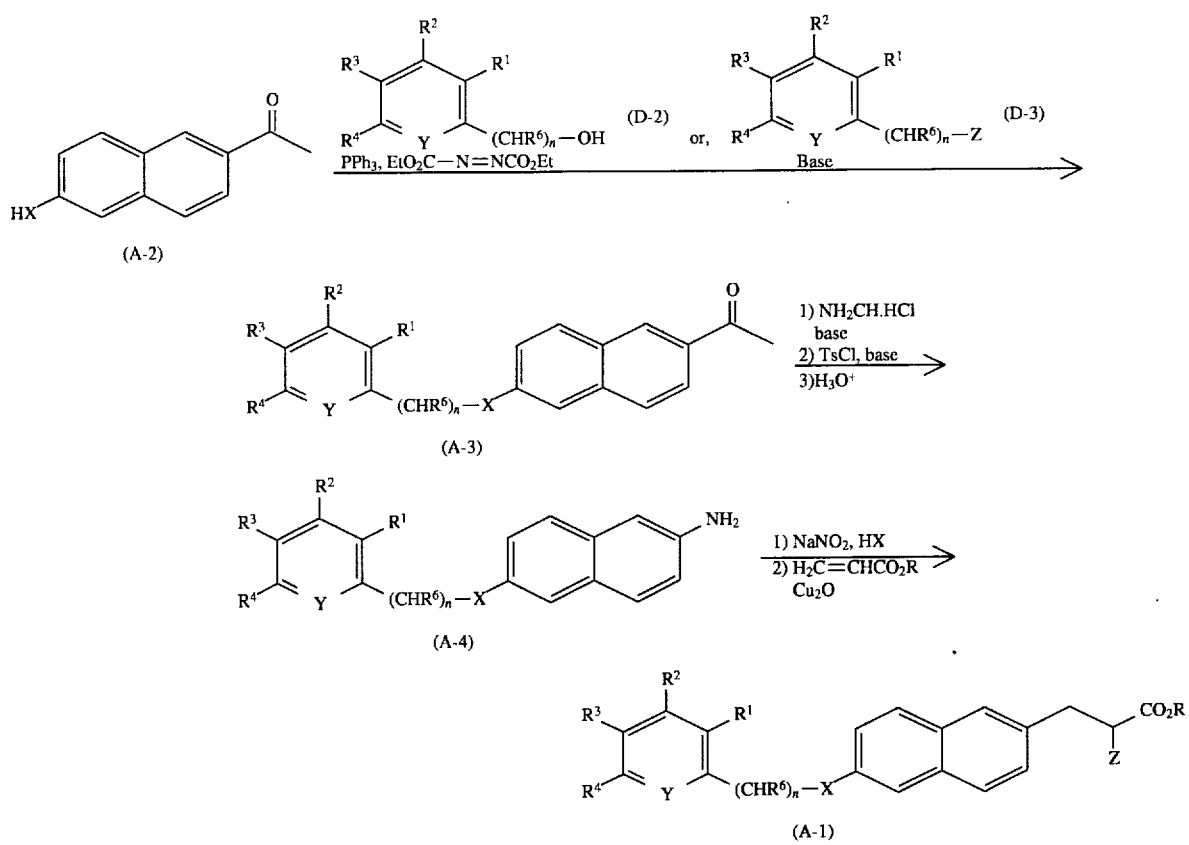

(Synthetic method of starting materials-1)

In the above formulae, X, Y, n, $R^1$, $R^2$, $R^3$, $R^4$, $R^6$, Z and R are as defined above.

The reaction for the conversion of compound (A-2) into compound (A-3) is carried out by reacting compound (A-2) with alcohol (D-2) in the presence of triphenylphosphine and diethyl azodicarboxylate. At this time, as a solvent, toluene, THF, diethyl ether, dioxane or the like is used. Compound (A-3) can be also synthesized by reacting compound (A-2) with halide (D-3) in the presence of a base.

Bases to be used include sodium hydride, potassium hydride, potassium carbonate and sodium carbonate. When n=0, a transition metal such as palladium, copper or the like is added occasionally as a catalyst, and THF, dioxane, diethyl ether, DMF, DMSO, N-methylpyrrolidone or the like is used as a solvent.

The reaction for the conversion of compound (A-3) into compound (A-4) is first started by converting the acetyl group of compound (A-3) into an oxime group using hydroxylamine hydrochloride and a base. At this time, sodium carbonate, potassium carbonate, sodium acetate, potassium acetate, sodium methoxide, sodium ethoxide or the like is used as a base and water, methanol, ethanol, acetone, a mixture thereof or the like is used as a solvent. Subsequently, the oxime group is reacted with p-toluenesulfonyl chloride in the presence of a base to convert into an aminoacetyl group by the Beckmann rearrangement. At this time, a tertiary amine such as pyridine, triethylamine or the like is used as a base. Dichloromethane, dichloroethane or the like is used as a solvent. Next, the amineacetyl group is hydrolyzed under acidic conditions to be converted into an amino group.

The reaction for the conversion of compound (A-4) into compound (A-1) is carried out by reacting the amino group of compound (A-4) with sodium nitrite in the presence of aqueous solution of hydrogen chloride, hydrogen bromide or hydrogen iodide to form a diazonium salt followed by reacting the diazonium salt with an acrylate ester in the presence of cuprous oxide catalyst. At this time, water or a mixture of water and acetone is used as a solvent.

Starting materials (B-1), (C-1) and (F-1) in Synthetic methods 2, 3, 6, 7 and 8 described above can be prepared by for example the following synthetic methods.

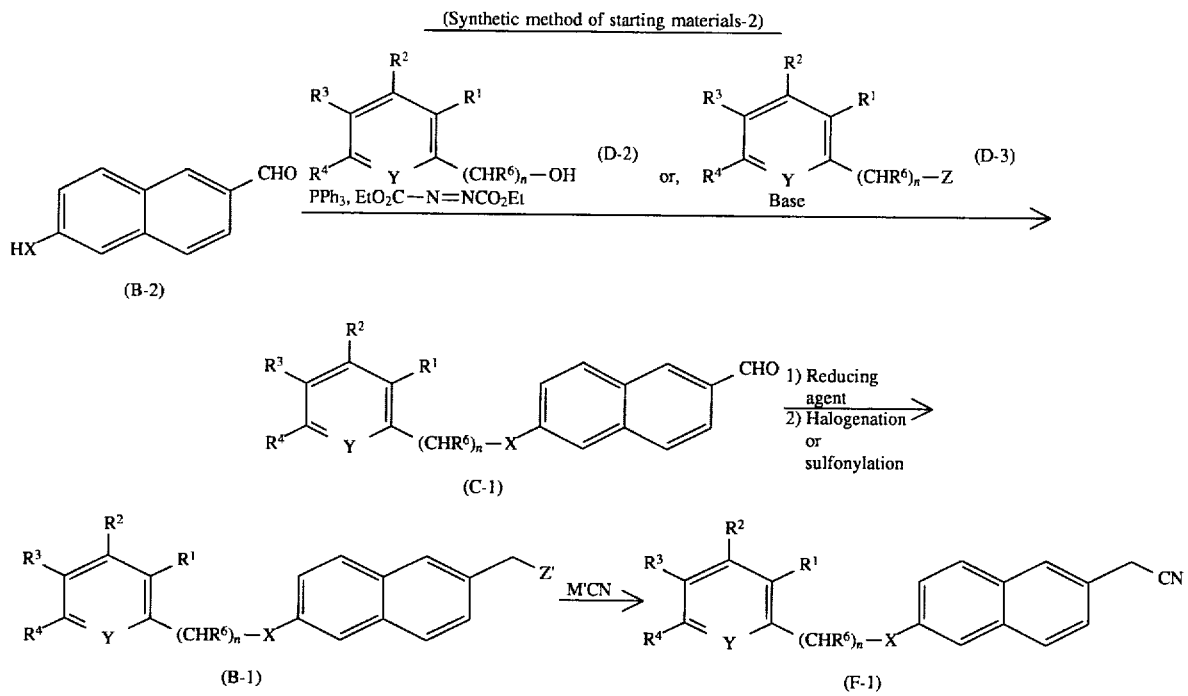

(Synthetic method of starting materials-2)

In the above formulae, X, Y, n, $R^1$, $R^2$, $R^3$, $R^4$, $R^6$, Z and Z' are as defined above and M' represents a metal such as sodium, potassium or the like.

The reaction for the conversion of compound (B-2) into compound (C-1) is performed by reacting compound (B-2) with alcohol (D-2) in the presence of triphenylphosphine and diethyl azodicarboxylate. At this time, toluene, THF, diethyl ether, dioxane or the like is used as a solvent. Compound (C-1) can be also obtained by reacting compound (B-2) with halide (D-3) in the presence of a base. At this time, sodium hydride, potassium hydride, potassium carbonate, sodium carbonate or the like is used as the base, and when n=0 a transition metal such as palladium, copper or the like is added as a catalyst sometimes. THF, dioxane, diethyl ether, DMF, DMSO, N-methylpyrrolidone or the like is used as a solvent.

In the reaction for the conversion of compound (C-1) into compound (B-1), the formyl group in compound (C-1) is first converted into a hydroxyl group using a reducing agent. At this time, sodium borohydride, lithium aluminium hydride, diisobutylalminium hydride or the like is used as a reducing agent. An inert solvent such as diethyl ether, THF, dioxane, dimethoxymethane, toluene or the like is used as a solvent, and as the case may be an alcohol such as ethanol, methanol, 1-propanol, 2-propanol or the like is used.

Next the above hydroxyl group is halogenated using a suitable halogenating agent for example, thionyl halide such as thionyl chloride, thionyl bromide or the like, phosphorus oxychloride, a halogenated hydroacid such as hydrobromic acid or the like, carbon tetrachloride, carbontetrabromide, bromine, iodine or the like: or sulfonated using a suitable sulfonating agent for example, sulfonyl chloride such as methanesulfonyl chloride, p-toluenesulfonyl chloride or the like, methanesulfonic anhydride, p-toluenesulfonic anhydride, trifluoromethanesulfonic anhydride or the like to obtain compound (B-1).

The reaction for the conversion of compound (B-1) into compound (F-1) can be performed by reacting compound (B-1) with sodium cyanide or potassium cyanide. At this time, DMF, DMSO, methanol, ethanol, dioxane, dimethoxymethane or the like is used as a solvent.

Starting materials (D-1), or (E-1) in Synthetic methods- 4 and 5 described above can be prepared by, for example, the following synthetic methods.

(Synthetic method of starting materials-3)

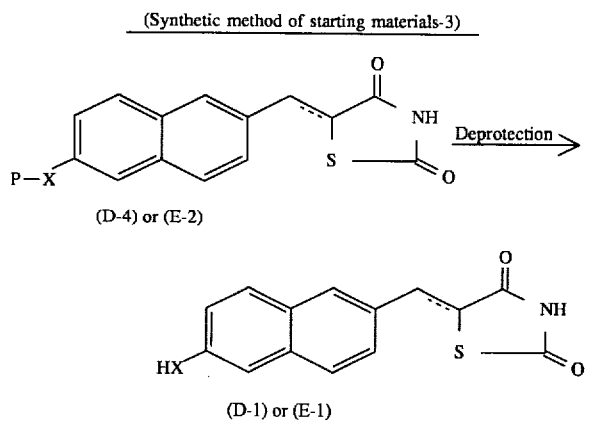

In the above formulae, X and the dotted lines are as defined above, and P represents a protecting group such as methoxymethyl, ethoxymethyl, 1-(1-ethoxy)-ethyl, 2-tetrahydropyranyl, trimethylsilyl, t-butyldimethylsilyl, trityl or the like.

Compounds (D-1) and (E-1) can be synthesized by deprotecting compounds (D-4) and (E-2) respectively wherein the dotted line in compound (D-4) does not represent a bond and the dotted line in compound (E-2) represents a bond under acidic conditions or in the presence of fluoride anions. At this time, methanol, ethanol, acetone, THF, dioxane, DMF, DMSO or a mixture of these solvents and water is used as a solvent.

Compound (E-2) can be also prepared by for example the following synthetic method.

(Synthetic method of intermediates-1)

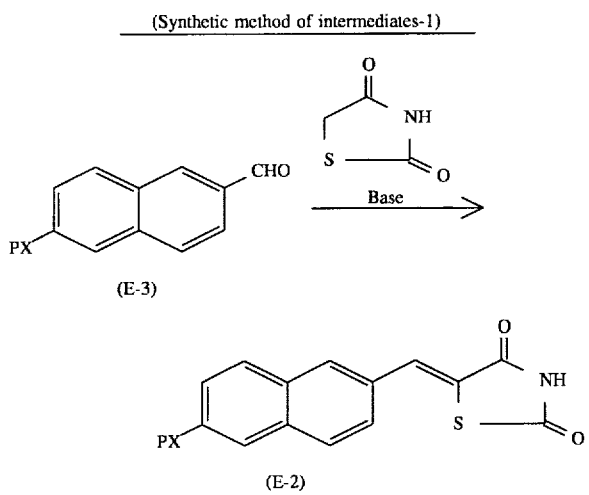

(E-3)

(E-2)

The reaction for the conversion of compound (E-3) into compound (E-2) is carried out by condensing compound (E-3) with 2,4-thiazolidinedione in the presence of a base under dehydration. At this time, bases to be used include inorganic bases such as sodium hydroxide, potassium hydroxide, sodium carbonate, potassium carbonate, sodium acetate, potassium acetate and the like and amines such as triethylamine, pyridine, piperidine, pyrrolidine, N-methylpiperidine, N-methylmorpholine and the like. Solvents used include alcohols such as methanol, ethanol, 1-propanol, 2-propanol and the like and sometimes the reaction can be also performed without solvent.

Compound (D-4) can be also prepared for example by two following methods.

(Synthetic method of intermediates-2)

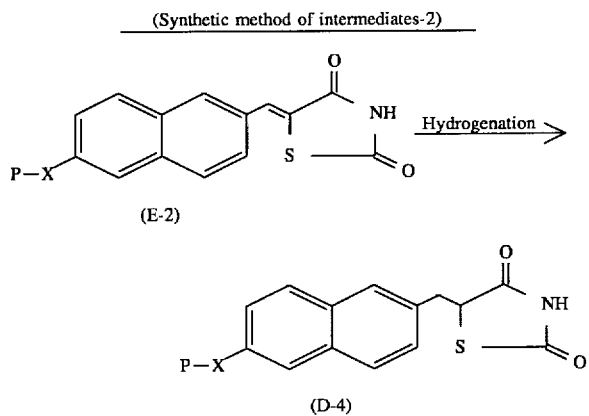

(E-2)

(D-4)

In the above formulae, X and P are as defined above.

The reaction for the conversion of compound (E-2) into compound (D-4) can be carried out by catalytically hydrogenating compound (E-2) with a transition metal catalyst such as palladium, platinum, rhodium or the like, or a catalyst which carrys said metal, under hydrogen or in the presence of cyclohexene. At this time, an alcohol such as methanol, ethanol, 1-propanol, 2-propanol or the like, THF, dioxane, acetic acid or the like is used as a solvent.

(Synthetic method of intermediates-3)

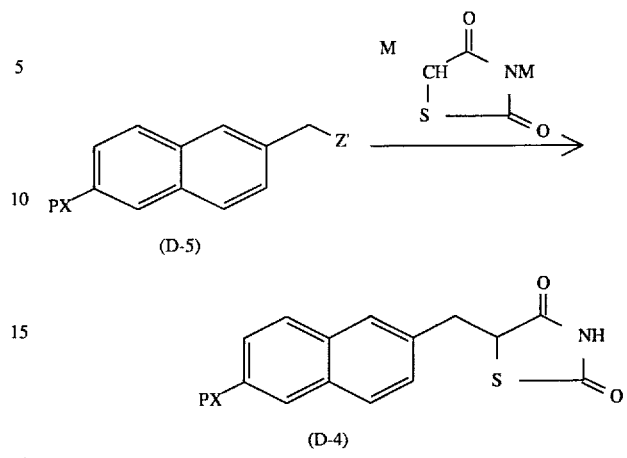

(D-5)

(D-4)

In the above formulae, X, P, Z' and M are as defined above.

The reaction for the conversion of compound (D-5) into compound (D-4) is conducted by reacting compound (D-5) with a metal salt of a dianion of 2,4-thiazolidinedione. Metal salts used include those of alkali metals such as lithium, sodium, potassium and the like and alkaline earth metals such as magnesium and the like. Solvents used include inert solvents such as diethyl ether, THF, dioxane, dimethoxymethane and the like.

<4> Use of the compounds of the present invention

The compounds of the present invention have excellent effects on reduction of blood sugar and blood lipid levels and can be used as medicaments. They can be formulated to various preparations suitable for various administration routes, using conventional carriers. For example, for oral administration, they are formulated in the form of tablet, capsule, granule, powder, liquid preparation and the like. Conventional excipients, binders, lubricants, coloring matters, disintegrators and the like can be used upon preparing solid preparations for oral administration.

Excipients include, for example, lactose, starch, talc, magnesium stearate, microcrystalline cellulose, methyl cellulose, carboxymethyl cellulose, glycerol, sodium alginate and arabic gum. Binders used include polyvinyl alcohol, polyvinylether, ethyl cellulose, arabic gum, shellac and sucrose, and lubricants used include magnesium stearate, and talc. Further, coloring materials and disintegrators known in the art can be used. Tablets may be coated by well known methods.

Liquid preparations may be aqueous or oily suspension, solution, syrup, elixir and the like, and they can be prepared by conventional methods. When injectable preparations are formulated, to the compounds of the present invention are added pH regulating agent, buffering agent, stabilizing agent, isotonicity, local anesthetic and the like and then preparations for subcutaneous, intramuscular or intravenous injections can be made by conventional methods. When a suppository is made, oily bases such as cacao butter, polyethylene glycols, Witepsol® (Dynamite Nobel Company) and the like may be used as base.

The dosage of such preparations is varied depending upon the condition, body weight, age, etc. of the patient and is not the same for all the patients. Preferably it is set such that the dosage of the compounds of the present invention is in the range of about 0.01 to 2000 mg/day per adult patient. The preparation is preferably divided and administered from one to four times per day.

EXAMPLE

The present invention will be more specifically explained by the following Preparations, Examples and Experiments. However, the present invention is not limited to such Preparation, Examples and Experiments in any aspects.

Preparation 1

Synthesis of 6-(2-pyridyl)-methyloxy-2-acetylnaphthalene

To a solution of 6-hydroxy-2-acetylnaphthalene (1.04 g) in DMF (20 ml) were added sodium hydride (60%, 0.65 g) and 2-picolyl chloride hydrochloride (1.28 g) under ice-cooling and the resultant-mixture was stirred at room temperature for 12 hours. The reaction mixture was partitioned between toluene and water. The organic layer was washed with a saturated saline solution and dried over anhydrous magnesium sulfate. After concentration in vacuo, the residue was subjected to column chromatography on silica gel eluting with ethyl acetate/hexane to obtain the title compound (1.17 g, yield =75.5%). The NMR spectrum is as follows.

NMR (CDCl$_3$); 2.70 (s, 3H), 5.35 (s, 2H), 7.23–7.27 (m, 2H), 7.33 (dd, 1H, J=2, 6 Hz, 9.1 Hz), 7.56 (d, 1H, J=7.8 Hz), 7.72 (dd, 1H, J=1, 9 Hz 7.6 Hz), 7.77 (d, 1H, J=1.4 Hz), 7.8 9 (d, 1H, J=8.9 Hz), 8.00 (dd, 1H, J=1.8 Hz 8.7 Hz), 8.41 (s, 1H), 8.65 (dd, 1H, J=0.9 Hz, 6.0 Hz)

Preparation 2

Synthesis of 6-(2-pyridyl)-methyloxy-2-(1-hydroxyiminoethyl)-naphthalene

To a solution of 6-(2-pyridyl)-methoxy-2-acetylnaphthalene (1.17 g) in methanol (50 ml) was added a solution of hydroxylamine hydrochloride (0.59 g) and potassium carbonate (1.17 g) in water (10 ml) and the resultant-mixture was heated under reflux with stirring for 3 hours.

After cooling to room temperature, water (50 ml) was added to the mixture. The precipitated solid was filtered off and dried in vacuo with heating to obtain the title compound (1.22 g), The NMR spectrum is as follows.

NMR (DMSO d-6); 2.24 (s, 3H), 5.30 (s, 2H), 7.28 (dd, 1H, J=2.5 Hz, 9.0 Hz), 7.37 (dd, 1H, J=1.8 Hz, 6.8Hz), 7.42 (d, 1H, J=2.5 Hz), 7.58 (d, 1H, J=7.8 Hz), 7.74 (d, 1H, J=8.8 Hz), 7.81–7.93 (m, 3H), 8.05 (s, 1H), 8.59 (dd, 1H, J=0.8 Hz, 4.8Hz), 11.2 (s, 1H)

Preparation 3

Synthesis of 2-acetylamino-6-(2-pyridylmethyloxy)naphthalene

To a solution of 2-(2-pyridylmethyloxy)-6-(1-hydroxyiminoethyl)-naphthalene (1.23 g) in pyridine (15 ml) was added p-toluenesulfonyl chloride (1.45 g) and the resultant-mixture was stirred at room temperature for 24 hours. The reaction mixture was made acid with hydrochloric acid and extracted with ethyl acetate. The organic layer was washed with an aqueous solution of sodium hydroxide and a saturated saline solution, dried over anhydrous magnesium sulfate, and concentrated in vacuo to obtain a residue. The residue was subjected to column chromatography on silica gel eluting with CHCl$_3$/MeOH to obtain the title compound (0.76 g, yield=62%). The NMR spectrum is as follows.

$^1$H-NMR (DMSO d-6); 2.07 (s, 3H), 5.26 (s, 2H), 7.22(dd, 1H, J=2.5 Hz, 9.0 Hz), 7.32–7.36 (m, 2H), 7.50–7.57 (m, 2H), 7.69–7.76 (m. 2H), 7.81(dt, 1H, J=1.5 Hz, 7.5 Hz), 8.20(s, 1H), 8.59(dd, 1H, J=0.5 Hz, 3.8 Hz), 10.03 (s, 1H)

Preparation 4

Synthesis of 2-amino-6-(2-pyridylmethyloxy)naphthalene

To a solution of 2-acetylamino-6-(2-pyridylmethyloxy)-naphthalene (0.76 g,) in 2-methoxyethanol (15 ml) was added 1N-hydrochloric acid (15 ml) and the resulting mixture was stirred with heating under reflux for 3 hours. After completion of the reaction, the reaction mixture was cooled to room temperature, made basic with an aqueous solution of sodium hydroxide, and then extracted with ethyl acetate. The organic layer was washed with a saturated saline solution, dried over anhydrous magnesium sulfate, and concentrated in vacuo to obtain the title compound (0.65 g) as the crude product. The NMR spectrum is as follows.

$^1$H-NMR (CDCl$_3$); 5.28 (s, 2H), 6.90–6.97 (m, 2H), 7.10 (d, 1H, 2.5 Hz), 7.16–7.25 (m, 2H), 7.52–7.58 (m, 3H), 7.71 (dt, 1H, J=1.8 Hz, 7.8 Hz), 8.61 (dd, 1H, J=0.5 Hz, 3.8 Hz)

Preparation 5

Synthesis of methyl 3-[6-(2-methylpyridyloxy)naphthyl]-methyl-2-chloro-propionate To a solution of 2-amino-6-(2-pyridylmethyloxy)naphthalene (0.65 g) in acetone (10 ml) were added concentrated hydrochloric acid (0.65 ml) and a solution of sodium nitrite (0.22 g) in water (1 ml). The resultant mixture was stirred under ice-cooling for 30 minutes. Methyl acrylate (1.4 ml) and cuprous oxide were then added to the mixture, and the latter was vigorously stirred for about 3 hours. After reaction, the reaction mixture was made basic with an aqueous solution of sodium hydroxide and extracted with ethyl acetate. The organic layer was washed with a saturated saline solution, dried over anhydrous magnesium sulfate, and concentrated in vacuo to obtain a residue.

The resulting residue was subjected to column chromatography on silica gel eluting with chloroform/methanol to obtain the title compound (0.22 g, yield=24%). The NMR spectrum is as follows.

NMR (CDCl$_3$); 3.29 (dd, 1H, J=7.5 Hz, 14.0 Hz), 3.53 (dd, 1H, J=7.5 Hz, 4.0 Hz), 3.73 (s, 3H), 4.52 (t, 1H, J=7.4 Hz), 5.32 (s, 2H), 7.18–7.31 (m, 4H), 7.54–7.75 (m, 5H), 8.62 (dd, 1H, J=0.5 Hz, 3.8 Hz)

Example 1

Synthesis of 5-[6-(2-pyridylmethyloxy)-2-naphthyl]-methyl-thiazolidine-2,4-dione (compound No. 772 in Table-4)

To a solution of methyl 3-[6-(2-pyridylmethyloxy)-naphthyl]-methyl-2-chloro-propionate (0.22 g) in 2-methoxyethanol (5 ml) were added thiourea (95 mg) and sodium acetate (76 mg) and the resultant mixture was stirred at 80° C. for 3 hours. After it had been confirmed by TLC that the starting material had disappeared, 1N hydrochloric acid (2.5 ml) was added to the mixture and it was stirred with heating under reflux for 6 hours.

After reaction, the mixture was cooled to room temperature, made basic with an aqueous solution of sodium hydroxide and extracted with ethyl acetate. The organic layer was washed with a saturated saline solution, dried over anhydrous magnesium sulfate and concentrated in vacuo to obtain a residue. The resulting residue was subjected to column chromatography on silica gel eluting with chloroform/methanol to obtain an amorphous solid. The solid was recrystallized from ethyl acetate to obtain the title compound (131 mg, yield=58%). The NMR spectrum, IR spectrum and melting point are as follows.

NMR (DMSO d-6); 3.21 (dd, 1H, J=4.6 Hz, 12.5 Hz), 3.51 (dd, 1H, J=4.6 Hz, 12.5 Hz), 4.95 (dd, 1H, J=4.1 Hz, 8.5 Hz), 5.28 (s, 2H), 7.26 (dd, 1H, J=2.5 Hz, 9.0 Hz), 7.33–7.39 (m, 3H), 7.56 (d, 1H, J=7.9 Hz), 7.67 (s, 1H), 7.72–7.87 (m, 3H), 8.59 (dd, 1H, J=0.5 Hz, 3.8 Hz), 12.02 (s, 1H)

IR (KBγ); 3054, 2796, 1742, 1703, 1601, 1483, 1437 1395, 1312, 1267, 1229 cm$^{-1}$ m.p.; 225°–227° C.

The compounds of Examples 2 and 3 were obtained with the method similar to that in Example 1.

The spectral data and yield of such products are described in Table 5.

Preparation 6

Synthesis of 6-(2-fluorobenzyloxy)-2-naphthylmethyl alcohol 6-(2-fluorobenzyloxy)-2-naphthylaldehyde (1.07 g) was dissolved in a mixed solvent of ethanol/THF (1:1) (22 ml). Sodium borohydride (144 mg) was added to the solution and it was stirred at room temperature for 1 hour.

After reaction, 1N hydrochloric acid was added to the above mixture, and the resultant mixture was extracted with chloroform. The organic layer was washed with a saturated saline solution, dried over anhydrous magnesium sulfate and concentrated in vacuo to obtain the title compound (1.07 g) as the crude product. The product was used in the next reaction without purification. The NMR spectrum is as follows.

NMR (CDCl$_3$); 4.82 (s, 2H), 5.25 (s, 2H), 7.08–7.35 (m, 5H), 7.45 (dd, 1H, J=1.5 Hz, 8.4 Hz), 7.56 (dt, 1H, J=1.5 Hz, 7.4 Hz), 7.73–7.77 (m, 3H)

Preparation 7

Synthesis of 6-(2-fluorobenzyloxy)-2-naphthylmethyl iodide

To a solution of 6-(2-fluorobenzyloxy)-2-naphthyl-methylalcohol (1.07 g) in THF (20 ml) were added triphenylphosphine (1.51 g) and imidazole (0.39 g), and a solution of iodine (1.21 g) in THF (10 ml) was gradually and dropwise added thereto under ice-cooling. Further the resulting mixture was stirred under ice-cooling for 30 minutes.

After reaction, ethyl acetate was added to the above mixture. The resulting mixture was washed with an aqueous solution of sodium hydrogenthiosulfate and a saturated saline solution, dried over anhydrous magnesium sulfate, and concentrated in vacuo to obtain a residue. The residue was subjected to column chromatography on silica gel eluting with ethyl acetate/hexane to obtain the title compound (0.24 g, yield=16%).

Example 4

Synthesis of 5-[6-(2-fluorobenzyloxy)-2-naphthyl]-methyl-thiazolidine-2,4-dione (Compound No. 5 in Table-1)

To a solution of 2,4-thiazolidinedione (108 mg) in THF (5 ml) was added hexamethylphosphoric triamide (0.5 ml) and the resulting mixture was cooled to −30° C., and n-butyl-lithium (1.6M, a solution in hexane) (1.1 ml) was added thereto. The mixture was stirred at −30° C. for 30 minutes and a solution of 6-(2-fluorobenzyloxy)-2-naphthylmethyl iodide (0.24 g) in THF (3 ml) was added. The resulting mixture was gradually warmed from −30° C. to room temperature and stirred for 6 hours. After reaction, ethyl acetate was added to the above reaction mixture. The organic layer was washed with an aqueous solution of ammonium chloride and a saturated saline solution, dried over anhydrous magnesium sulfate, and concentrated in vacuo to obtain a residue. The residue was subjected to column chromatography on silica gel eluting with ethyl acetate/ hexane to obtain an amorphous solid. The solid was recrystallized from ethyl acetate/hexane to obtain the title compound (152 mg, yield=65%). The NMR spectrum, IR spectrum and melting point are as follows.

NMR (DMSO d-6); 3.23 (dd, 1H, J=9.5 Hz, 14.0 Hz), 3.51 (dd, 1H, J=4.3 Hz, 14.0 Hz), 4.9 g (dd, 1H, J=4.3 Hz, 9.5 Hz), 5.24 (s, 2H), 7.20–7.30 (m, 4H), 7.38 (t, 1H, J=8.8 Hz), 7.45 (s 1H), 7.61 (t 1H, J=7.5 Hz), 7.70 (s 1H), 7.76 (d 1H, J=5.8 Hz), 7.79 (d 1H, J=6.0 Hz), 12.03 (s 1H),

IR (KBγ); 3254, 3055, 1759, 1674, 1607, 1493, 1393, 1325, 1269, 1231 m.p. :150°–151° C.

Compounds of Examples 5, 6, 7, 8, 9, 10 and 11 were obtained by a method similar to that described in Example 4. These compounds are represented by the following formula (I-e).

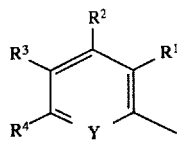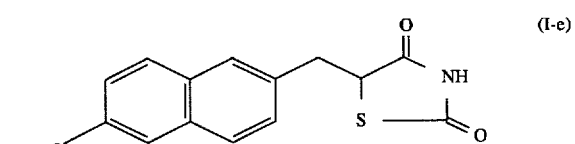

The spectral data and yield values of the above compounds are described in Table 5 together with those of the compounds obtained in Examples 2 and 3.

TABLE 5

| Example No. | R³-R⁴-Y / R²-R¹-(CHR⁶)ₙ— substituent | mp (°C.) Yield (%) | NMR (ppm) | IR (cm⁻¹) |
|---|---|---|---|---|
| 2 | benzyl | 181~183 58 | 3.23(dd, 1H, J=9.4Hz, 14.2Hz)<br>3.51(dd, 1H, J=4.4Hz, 14.1Hz)<br>4.99(dd, 1H, J=4.4Hz, 9.4Hz)<br>5.20(s, 2H)<br>7.22(dd, 1H, J=2.5Hz, 8.9Hz)<br>7.33–7.52 (m, 7H)<br>7.67(s, 1H), 7.70(d, 1H, J=9.5Hz)<br>7.78(d, 1H, J=9.5Hz), 12.41(s, 1H) | 3260, 3063<br>1759, 1691<br>1606, 1504<br>1454, 1391<br>1336, 1263<br>1231 |
| 3 | phenyl | 137~138 32 | 3.24(dd, 1H, J=4.8Hz, 14.2Hz)<br>3.53(dd, 1H, J=4.1Hz, 13.9Hz)<br>5.01(dd, 1H, J=4.5Hz, 9.0Hz)<br>7.08(dd, 2H, J=0.8Hz, 7.7Hz)<br>7.17 (t, 1H, J=7.3Hz)<br>7.27(dd, 1H, J=2.3Hz, 8.9Hz)<br>7.30–7.50 (m, 4H)<br>7.77(d, 2H, J=8.8Hz)<br>7.91(d, 1H, J=8.9Hz) | 3431, 3260<br>3059, 1745<br>1685, 1591<br>1491, 1475<br>1323, 1228<br>1143 |
| 5 | 3-F-benzyl | 156~159 83 | 3.23(dd, 1H, J=9.3Hz, 14.1Hz)<br>3.51(dd, 1H, J=4.3Hz, 14.1Hz)<br>4.98(dd, 1H, J=4.3Hz, 9.3Hz)<br>5.23(s, 2H), 7.16–7.46(m, 7H)<br>7.68(s, 1H), 7.74(d, 1H, J=8.5Hz)<br>7.79(d, 1H, J=9.1Hz), 12.03(s, 1H) | 3179, 3057<br>1755, 1692<br>1607, 1487<br>1460, 1381<br>1335, 1262<br>1233 |
| 6 | 4-F-benzyl | 151~153 76 | 3.23(dd, 1H, J=9.4Hz, 14.2Hz)<br>3.51(dd, 1H, J=4.3Hz, 14.2Hz)<br>4.98(dd, 1H, J=4.3Hz, 9.4Hz)<br>5.18(s, 2H), 7.19–7.58(m, 5H)<br>7.70(d, 1H, J=13.7Hz)<br>7.78(d, 1H, J=9.4Hz | 3256, 3061<br>1763, 1691<br>1607, 1512<br>1391, 1333<br>1271, 1231 |
| 7 | 2-Cl-benzyl | 171~173 23 | 3.23(dd, 1H, J=9.0Hz, 14.6Hz)<br>3.50(dd, 1H, J=4.2Hz, 14.6Hz)<br>4.99(dd, 1H, J=4.2Hz, 9.0Hz)<br>5.22(s, 2H)<br>7.21–7.48(m, 5H)<br>7.63–7.82(m, 5H) | 3204, 3063<br>1757, 1682<br>1605, 1395<br>1335, 1263<br>1233, 1155 |
| 8 | 4-Cl-benzyl | 150~152 23 | 3.21(dd, 1H, J=9.3Hz, 18.0Hz)<br>3.51(dd, 1H, J=4.3Hz, 18.0Hz)<br>4.98(dd, 1H, J=4.3Hz, 9.3Hz)<br>5.20(s, 2H)<br>7.22(dd, 1H, J=2.3Hz, 8.8Hz)<br>7.35–7.55(m, 4H)<br>7.67–7.77(m, 5H), 12.04(s, 1H) | 3158, 3054<br>1744, 1701<br>1605, 1491<br>1393, 1337<br>1267, 1229 |
| 9 | 2-Br-benzyl | 158~161 52 | 3.27(dd, 1H, J=9.0Hz, 18.3Hz)<br>3.52(dd, 1H, J=4.3Hz, 18.3Hz)<br>5.26(s, 2H)<br>7.24(d, 1H, J=9.0Hz)<br>7.35–7.43(m, 5H)<br>7.52–7.82(m, 4H), 12.04(s, 1H) | 3204, 3061<br>1757, 1682<br>1604, 1393<br>1335, 1263<br>1231, 1026 |
| 10 | 2-CF₃-benzyl | 149~151 88 | 3.24(dd, 1H, J=9.3Hz, 14.0Hz)<br>3.53(dd, 1H, J=4.3Hz, 14.0Hz)<br>4.99(dd, 1H, J=4.3Hz, 9.3Hz)<br>5.33(s, 2H)<br>7.22(dd, 1H, J=2.3Hz, 9.3Hz)<br>7.35–7.41(m, 2H)<br>7.60(t, 1H, J=7.8Hz)<br>7.69–7.83(m, 6H), 12.04(s, 1H) | 3142, 3044<br>1765, 1707<br>1607, 1452<br>1397, 1314<br>1269, 1230<br>1182 |
| 11 | 4-CF₃-benzyl | 162~164 64 | 3.24(dd, 1H, J=9.3Hz, 14.0Hz)<br>3.51(dd, 1H, J=4.3Hz, 14.0Hz)<br>4.98(dd, 1H, J=4.3Hz, 9.3Hz)<br>5.34(s, 2H)<br>7.25(dd, 1H, J=2.3Hz, 9.0Hz)<br>7.35–7.40(m, 1H)<br>7.68–7.82(m, 8H), 12.03(s, 1H) | 3162, 3056<br>1753, 1699<br>1607, 1481<br>1397, 1323<br>1261, 1209 |

Preparation 8

Synthesis of 5-(6-hydroxy-2-naphthyl-methyl-thiazolidine-2,4-dione

To a solution of 5-(t-butyldimethylsilyloxy-2-naphthyl)-methyl-thiazolidine-2,4-dione (897 mg) in DMF (7 ml) were added potassium fluoride (269 mg) and 47% hydrobromic acid (0.12 ml). The reaction mixture was stirred at room temperature for 1.5 hours, and then the reaction mixture was added to 3N hydrochloric acid (50 ml) and extracted with chloroform.

The organic layers were collected, washed with a saturated saline solution and concentrated to obtain a crude product. The product was subjected to column chromatography on silica gel eluting with chloroform/methanol to obtain the title compound (250 mg, yield=40%). The NMR spectrum is as follows.

$^1$H NMR (2.50 M Hz, DMSO); 3.20 (dd, 1H, J=9.3 Hz, 14.3 Hz), 3.48 (dd, 1H, J=4.3 Hz, 1.40 Hz), 4.97 (dd, 1H, J=4.3 Hz, 9.3 Hz), 7.06 (d, 1H, J=8.4 Hz), 7.08 (s, 1H), 7.27 (d, 1H, J=8.5 Hz), 7.60 (s, 1H), 7.62 (d, 1H, J=9.0 Hz), 7.69 (d, 1H, J=9.0 Hz)

Example 12

Synthesis of 5-[6-(2,4,6-trifluorobenzyloxy)-2-naphthyl]-methyl-thiazolidine-2,4-dione (compound No. 153 in Table 1)

To a suspension of sodium hydride in DMF (6 ml) which had been washed three times with hexane was added dropwise a solution of (6-hydroxy-2-naphthyl)-methyl-thiazolidinedione (250 mg) in DMF (1 ml) followed by 2,4,6-trifluorobenzyl bromide (149 mg). The resulting mixture was stirred at room temperature for 2 hours. The reaction mixture was added to an aqueous saturated ammonium chloride solution, and the mixture was extracted with ethyl acetate.

The resultant organic layers was washed with a saturated saline solution and concentrated to obtain a residue. The residue was subjected to column chromatography on silica gel eluting with ethyl acetate/hexane to obtain the title compound (97 mg, yield=39%). The spectral data and melting point are as follows.

$^1$H NMR (CDCl$_3$, 2.50 Hz); 3.27 (dd, 1H, J=9.8 Hz, 14.1 Hz), 3.68 (dd, 1H, J=3.9 Hz, 14.0 Hz), 4.62 (dd, 1H, J=4.0 Hz, 9.9 Hz), 5.18 (s, 2H), 6.6814 6.78 (m, 2H), 7.17–7.34 (m, 3H), 7.55–7.75 (m, 3H), 9.71 (s, 1H), 12.03 (s, 1H),

IR; 1688, 1667, 1630, 1606, 1227, 1122, 1017, 845 cm$^{-1}$ m.p.; 166°–167° C.

Preparation 9

Synthesis of 6-benzyloxy-2-naphthylaldehyde 6-benzyloxy-2-naphthylaldehyde (0.36 g) was dissolved in a mixture of THF (10 ml) and DMF (1 ml). The solution was cooled to 0° C., and 60% sodium-hydride in oil (0.23 g) was added thereto. The resulting mixture was stirred at 0° C. for 30 minutes, and then benzyl bromide (1 ml) was slowly added dropwise. After addition, the resulting mixture was warmed to room temperature and stirred for 5 hours.

After reaction, methanol (0.5 ml) and water (5 ml) were poured into the reaction mixture and it was extracted three times with ethyl acetate (50 ml). The ethyl acetate layer was washed with a saturated saline solution, dried over MgSO$_4$, and the ethyl acetate was distilled off. The oily residue was subjected to column chromatography on silica gel (30 g) eluting with hexane/ethyl acetate. The resulting solution was concentrated and dried to obtain the objective title compound (220 mg, yield=40%). The NMR spectrum is as follows.

$^1$H NMR (DMSO); 5.27 (s, 2H), 7.34–7.44 (m, 5H), 7.50–7.56 (m, 3H), 7.84 (d, 1H, J=8.8 Hz), 7.93 (d, 1H, J=8.3 Hz), 8.08 (d, 1H, J=9.0 Hz), 8.49 (s, 1H), 10.07 (s, 1H),

Preparation 10

Synthesis of 6-(2-fluorobenzyloxy)-2-naphthylaldehyde 6-hydroxy-2-naphthylaldehyde (520 mg) and triphenylphosphine (0.87 g) was dissolved in THF (20 ml), and then 2-fluorobenzyl alcohol (0.49 ml) was added thereto. The reaction mixture was stirred, and diethyl azodicarboxylate (0.57 ml) was slowly added. The mixture was stirred at room temperature for 36 hours.

After reaction, the solvent was distilled off, and the residue was subjected to column chromatography on silica gel (50 g) eluting with hexane/ethyl acetate. The combined solutions were concentrated, and dried to obtain the objective title compound (654 mg, yield=81%). The NMR spectrum is as follows.

$^1$H NMR (CDCl$_3$); 5.41 (s, 2H), 7.22 (d, 1H, J=2.5 Hz), 7.32 (dd, 1H, J=9.0 Hz 2.5 Hz), 7.44 (t, 1H, J=7.8 Hz), 7.58 (t, 1H, J=8.3 Hz), 7.72 (d, 2H, J=8.5 Hz), 7.78 (d, 1H, J=8.5 Hz), 7.8–8.0 (m, 2H), 8.26 (s, 1H), 10.09 (s, 1H),

Example 13

Synthesis of 5-(6-benzyloxy-2-naphthyl)-methylene-thiazolidine-2,4-dione (Compound No. 294 in Table-1)

A mixture of 6-benzyloxy-2-naphthylaldehyde (220 mg), 2,4-thiazolidinedione (128 mg) and sodium acetate (0.17 g) was heated at 115° C. for 30 minutes. After reaction, the reaction mixture was allowed to cool to room temperature, washed with water and acetone (0.5 ml), and extracted with ethyl acetate. The extract was dried and the solvent was distilled off. The resulting product was recrystallized from ethyl acetate to obtain the title compound (140 mg, yield= 46%). The spectral data are as follows.

$^1$H NMR (DMSO); 5.23 (s, 2H), 7.27(dd, 1H, J=8.9 Hz, 2.5 Hz), 7.3–7.5 (m, 4H), 7.51 (d, 2H, J=6.7 Hz), 7.62 (d, 2H, J=9.3 Hz), 7.86 (d, 1H, J=8.7 Hz), 7.91 (d, 1H, J=9.1 Hz), 8.02 (s, 1H),

IR (KBγ);

3437, 3028, 1689, 1599, 1566, 1307, 1267, 1213 cm$^{-1}$, m.p.; 2.91° C. (decomposition)

Example 15

Synthesis of 5-[6-(2-fluorobenzyloxy)-2-naphthyl]-methylene-thiazolidine-2,4-dione (compound No. 299 in Table 1)

A mixture of 6-(2-fluorobenzyloxy)-2-naphthylaldehyde (300 mg), 2,4-thiazolidinedione (144 mg) and sodium acetate (226 mg) was heated at 120° C. for 30 minutes, allowed to cool to room temperature on standing, washed with acetic acid (1 ml), water (10 ml) and ethyl acetate (10 ml), and filtered. The resulting precipitate was recrystallized from ethyl acetate to obtain the title compound (361 mg, yield=89%). The spectral data and melting point are as follows.

¹H NMR (DMSO); 5.27 (s, 2H), 7.2–7.3 (m, 3H), 7.43 (t, 1H, J=7.9 Hz), 7.51 (d, 1H, J=2.2 Hz), 7.6–7.7 (m, 3H), 7.90 (t, 2H, J=8.5 Hz), 8.04 (s, 1H)

IR (KBγ);

3435, 3124, 3022, 2775, 1786, 1691, 1585, 1493, 1394, 1325, 1271, 1190, 1008 cm⁻¹, m.p.; 247° C. (decomposition)

The compounds of Examples 14, 16–39, 41, 43–56 were obtained by methods similar to that described in Examples 13 and 15. These compounds were represented by the following formula (I-f).

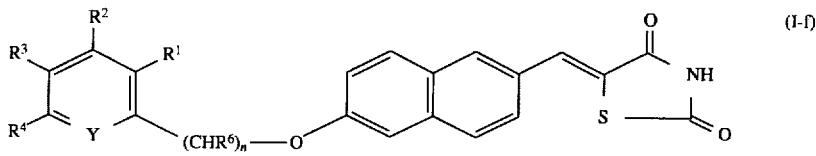

(I-f)

The spectral data and yield values of the above compounds are described in Table 6 wherein Me, Ac and Ph represent methyl, acetyl and phenyl, respectively.

TABLE 6

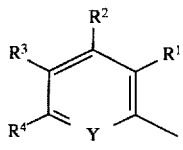

| Example No. | (substituent structure) | mp (°C.) Yield (%) | NMR (ppm) | IR (cm⁻¹) |
|---|---|---|---|---|
| 14 | phenyl-CH₂CH₂– | 195–197<br>89 | 3.10(t, 2H, J=6.9Hz)<br>4.31(t, 2H, J=7.0Hz)<br>7.14(dd, 1H, J=2.6Hz, 9.2Hz)<br>7.23(d, 1H, J=6.8Hz)<br>7.28–7.38(m, 7H)<br>7.60(d, 1H, J=8.3Hz)<br>7.78–7.84(m, 2H), 7.93.(s, 1H) | 3422, 3059<br>3026, 2926<br>1689, 1564<br>1309, 1271<br>1182, 1026 |
| 16 | 3-F-phenyl-CH₂– | 195<br>(Decomposition)<br>82 | 5.25(s, 2H), 7.17(t, 1H, J=8.7Hz)<br>7.26(d, 1H, J=10.7Hz)<br>7.35(d, 2H, J=7.9Hz)<br>7.41–7.50(m, 3H)<br>7.63(d, 1H, J=8.6Hz)<br>7.83(d, 1H, J=8.7Hz)<br>7.88(d, 1H, J=9.1Hz), 7.97(s, 1H) | 3022, 2893<br>1691, 1593<br>1568, 1309<br>1273, 1211<br>1186 |
| 17 | 4-F-phenyl-CH₂– | 261<br>(Decomposition)<br>62 | 5.22(s, 2H), 7.20–7.30(m, 3H)<br>7.47(s, 1H), 7.50–7.70(m, 2H)<br>7.67(d, 2H, J=9.1Hz)<br>7.90(m, 2H), 8.04(s, 1H) | 3431, 3128<br>3026, 2787<br>1730, 1689<br>1593, 1514<br>1329, 1222<br>1178, 1157 |
| 18 | 2-Cl-phenyl-CH₂– | 244<br>(Decomposition)<br>84 | 5.30(s, 2H)<br>7.31(d, 1H, J=8.5Hz)<br>7.38–7.42(m, 2H)<br>7.52(brs, 2H), 7.62–7.66(m, 2H)<br>7.78(s, 1H)<br>7.92(d, 1H, J=8.2Hz)<br>7.96(d, 1H, J=8.7Hz), 8.08(s, 1H) | 3427, 3136<br>3024, 2793<br>1734, 1689<br>1587, 1323<br>1271, 1182 |
| 19 | 4-Cl-phenyl-CH₂– | 260<br>70 | 5.61(s, 2H)<br>7.66(d, 1H, J=8.4Hz)<br>7.84(brs, 3H)<br>7.90(d, 2H, J=8.0Hz)<br>7.99(d, 1H, J=9.1Hz), 8.19(s, 1H)<br>8.26(d, 1H, J=8.6Hz)<br>8.32(d, 1H, J=8.9Hz), 8.45(s, 1H) | 3447, 3105<br>2982, 2791<br>1741, 1687<br>1581, 1334<br>1271, 1184<br>1170 |
| 20 | 2-Br-phenyl-CH₂– | 300 or over<br>36 | 5.25(s, 2H)<br>7.27–7.90(m, 10H)<br>8.02(s, 1H) | 3429, 1690<br>1599, 1568<br>1395, 1312<br>1273, 1208<br>1181, 1026 |

TABLE 6-continued

| Example No. | $R^3$ $R^4$ $Y$ $R^2$ $R^1$ $(CHR^6)_n$— | mp (°C.) Yield (%) | NMR (ppm) | IR (cm$^{-1}$) |
|---|---|---|---|---|
| 21 | 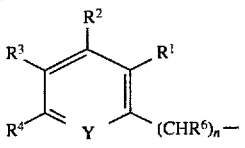 | 208 (Decomposition) 51 | 5.23(s, 2H) 7.29(d, 1H, J=7.8Hz) 7.47(d, 3H, J=7.5Hz) 7.60(d, 2H, J=7.8Hz) 7.65(s, 1H), 7.77(s, 1H) 7.89(d, 1H, J=9.1Hz) 7.94(d, 1H, J=9.3Hz), 8.07(s, 1H) | 3445, 3107 2987, 1741 1687, 1583 1475, 1334 1269, 1184 1170 |
| 22 | 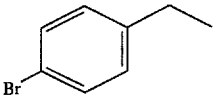 | 266~268 (Decomposition) 70 | 2.37(s, 3H), 5.22(s, 2H) 7.25(m, 4H), 7.44(s, 1H) 7.49(d, 2H, J=2.1Hz) 7.65(d, 1H, J=8.4Hz) 7.87(t, 2H, J=7.5Hz, J=8.3Hz) 7.98(s, 1H) | 3429, 3059 3026, 1689 1599, 1566 1394, 1311 1273, 1211 1176 |
| 23 | 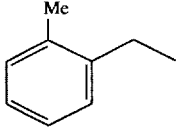 | 222~223 76 | 2.33(s, 3H), 5.20(s, 2H) 7.16(s, 1H), 7.20-7.40(m, 4H) 7.48(s, 1H) 7.63(d, 1H, J=8.3Hz) 7.81(s, 1H), 7.88-7.96(m, 2H) 8.08(s, 1H) | 3425, 3132 3022, 1745 1693, 1606 1340, 1263 1186, 997 |
| 24 | 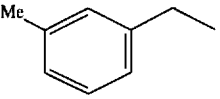 | 194 (Decomposition) 52 | 2.30(s, 3H), 5.19(s, 2H) 7.21(d, 2H, J=7.7Hz) 7.28(d, 1H, J=9.0Hz) 7.39(d, 2H, J=7.9Hz) 7.47(s, 1H), 7.63(d, 1H, J=8.5Hz) 7.82(s, 1H), 7.89(d, 1H, J=8.9Hz) 7.94(d, 1H, J=9.1Hz), 8.08(s, 1H) | 3443, 3169 3051, 1743 1689, 1606 1586, 1336 1265, 1180 |
| 25 | 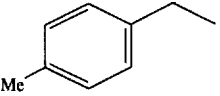 | 283~284 (Decomposition) 86 | 3.85(s, 3H), 5.19(s, 2H) 6.99(t, 1H, J=6.7Hz) 7.09(d, 1H, J=8.2Hz) 7.23(d, 1H, J=9.1Hz) 7.33-7.49(m, 4H) 7.64(d, 1H, J=8.7Hz) 7.84(d, 1H, J=3.6Hz) 7.87(d, 1H, J=4.3Hz), 7.98(s, 1H) | 3431, 3059 1689, 1602 1562, 1413 1311, 1275 1246, 1114 1041 |
| 26 | 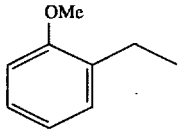 | 236 (Decomposition) 66 | 3.76(s, 3H), 5.22(s, 2H) 6.91(dd, 1H, J=7.5Hz, 2.0Hz) 7.08(brs, 2H), 7.27-7.35(m, 2H) 7.46(s, 1H), 7.63(d, 1H, J=8.5Hz) 7.76(s, 1H), 7.89(d, 1H, J=8.7Hz) 7.94(d, 1H, J=9.2Hz), 8.07(s, 1H) | 3445, 3121 3018, 2779 1739, 1682 1585, 1479 1332, 1273 1186, 1151 |
| 27 | 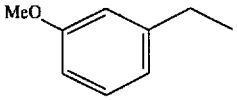 | 221~223 (Decomposition) 57 | 3.76(s, 3H), 5.15(s, 2H) 6.97(d, 2H, J=8.3Hz) 7.25(d, 1H, J=9.3Hz) 7.45(d, 3H, J=8.0Hz) 7.63(d, 2H, J=10.6Hz) 7.89(m, 2H), 8.02(s, 1H) | 3429, 3009 1687, 1610 1516, 1304 1251, 1174 1032 |
| 28 | 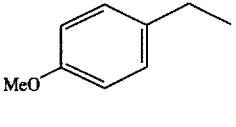 | 234~238 (Decomposition) 43 | 3.39(s, 3H), 5.22(s, 2H) 5.28(s, 2H), 7.03(t, 1H, J=7.2Hz) 7.16(d, 1H, J=8.1Hz) 7.25(dd, 1H, J=9.0Hz, 2.3Hz) 7.33(t, 1H, J=6.8Hz) 7.46-7.51(m, 2H) 7.63(t, 2H, J=3.4Hz) 7.89(dd, 2H, J=9.0Hz, 5.2Hz) 8.02(s, 1H) | 3427, 2953 1689, 1593 1566, 1494 1309, 1271 1178, 1153 999 |
| 29 | 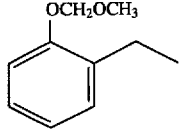 | 213 (Decomposition) 68 | 3.36(s, 3H), 5.16(s, 2H) 5.18(s, 2H), 7.04(d, 2H, J=7.5Hz) 7.26(d, 1H, J=9.2Hz) 7.40-7.50(m, 3H) 7.62(d, 1H, J=8.1Hz) 7.80(s, 1H), 7.87-7.95(m, 2H) 8.07(s, 1H) | 3454, 3138 3016, 1741 1685, 1591 1514, 1327 1271, 1242 1186, 1003 |

TABLE 6-continued

| Example No. | (structure: R³, R², R¹, R⁴, Y, (CHR⁶)ₙ—) | mp (°C.) Yield (%) | NMR (ppm) | IR (cm⁻¹) |
|---|---|---|---|---|
| 30 | 2-CN-benzyl | 164~167 (Decomposition) 53 | 5.38(s, 2H) 7.28(dd, 1H, J=9.0Hz, 2.2Hz) 7.52(s, 1H) 7.57–7.67(m, 4H) 7.73–7.82(m, 2H) 7.91(m, 3H), 8.03(s, 1H) | 3435, 2226 1689, 1599 1566, 1396 1311, 1273 1186, 1022 |
| 31 | 3-CN-benzyl | 256~258 (Decomposition) 63 | 5.31(s, 2H) 7.33(dd, 1H, J=9.0Hz, 2.1Hz) 7.48(s, 1H), 7.63(t, 2H, J=7.4Hz) 7.81(brs, 2H), 7.85(s, 1H) 7.89(d, 1H, J=4.2Hz) 7.94(d, 1H, J=5.6Hz), 7.99(s, 1H) 8.09(s, 1H) | 3433, 3134 3028, 2789 2231, 1732 1687, 1589 1479, 1327 1273, 1186 |
| 32 | 4-CN-benzyl | 240 (Decomposition) 39 | 5.37(s, 2H) 7.33(d, 1H, J=8.6Hz) 7.47(s, 1H), 7.60–7.70(m, 3H) 7.81(s, 1H), 7.89(d, 3H, J=8.2Hz) 7.97(d, 1H, J=8.8Hz) 8.09(s, 1H) | 3431, 3204 3061, 2235 1741, 1705 1595, 1394 1305, 1271 1188, 1151 |
| 33 | 2-NO₂-benzyl | 241 (Decomposition) 76 | 5.61(s, 2H) 7.30(d, 1H, J=8.6Hz) 7.46(s, 1H), 7.64(brs, 3H) 7.70–7.90(m, 4H) 8.04(s, 1H) 8.16(d, 1H, J=7.7Hz) | 3431, 3059 2920, 1689 1599, 1566 1529, 1340 1309, 1271 1182 |
| 34 | 3-NO₂-benzyl | 180 (Decomposition) 92 | 5.41(s, 2H), 7.33(d, 1H, J=7.6Hz) 7.49(s, 1H), 7.60–7.80(m, 2H) 7.80–8.10(m, 3H) 8.20(d, 1H, J=8.0Hz) 8.38(s, 1H) | 3431, 3059 1691, 1535 1348, 1315 1273, 1186 |
| 35 | 4-NO₂-benzyl | 195 (Decomposition) 40 | 5.43(s, 2H), 7.35(d, 1H, J=8.8Hz) 7.49(s, 1H), 7.64(d, 1H, J=8.6Hz) 7.79(d, 3H, J=6.6Hz) 7.89(d, 1H, J=8.5Hz) 7.97(d, 1H, J=9.0Hz) 8.08(s, 1H), 8.28(d, 1H, J=8.4Hz) | 3431, 3302 3051, 1741 1705, 1593 1516, 1341 1271, 1186 |
| 36 | 3-HOOC-benzyl | 289 (Decomposition) 52 | 5.34(s, 1H), 7.33(d, 1H, J=7.5Hz) 7.50(s, 1H), 7.56(d, 1H, J=7.8Hz) 7.63(d, 1H, J=8.3Hz) 7.76(d, 1H, J=7.4Hz) 7.84(s, 1H), 7.89–7.89(m, 3H) 8.08(d, 2H, J=4.7Hz) | 3435, 3142 3047, 2361 1734, 1682 1593, 1319 1271, 1186 1155 |
| 37 | 4-HOOC-benzyl | 226~228 (Decomposition) 71 | 5.35(s, 2H) 7.34(d, 1H, J=8.7Hz) 7.48(s, 1H), 7.62(d, 3H, J=7.6Hz) 7.85(s, 1H), 7.90(d, 2H, J=8.9Hz) 7.97(d, 2H, J=8.3Hz) 8.10(s, 1H) | 3422, 3020 1738, 1685 1591, 1394 1350, 1273 1184, 1012 |
| 38 | 3-MeOOC-benzyl | 195 (Decomposition) 79 | 3.86(s, 3H), 5.34(s, 2H) 7.31(dd, 1H, J=8.9Hz, 2.4Hz) 7.47(d, 1H, J=2.1Hz) 7.57(t, 1H, J=7.7Hz) 7.64(d, 1H, J=8.5Hz), 7.72(s, 1H) 7.79(d, 1H, J=7.6Hz) 7.88(d, 1H, J=8.7Hz) 7.94(d, 2H, J=8.9Hz) 8.08(d, 2H, J=10.2Hz), 8.31(s, 1H) | 3429, 3192 3063, 1693 1597, 1394 1302, 1274 1205 |
| 39 | 4-MeOOC-benzyl | 228 (Decomposition) 63 | 3.85(s, 3H), 5.35(s, 2H) 7.33(dd, 1H, J=9.0Hz, 2.3Hz) 7.46(s, 1H), 7.60–7.70(m, 3H) 7.75(s, 1H), 7.88(d, 1H, J=8.7Hz) 7.90–8.00(m, 3H), 8.07(s, 1H) | 3435, 3184 3063, 2957 1711, 1597 1394, 1275 1186, 1018 |

TABLE 6-continued

| Example No. | $R^2$, $R^3$, $R^1$, $R^4$, Y, $(CHR^6)_n$— | mp (°C.) Yield (%) | NMR (ppm) | IR (cm$^{-1}$) |
|---|---|---|---|---|
| 41 | 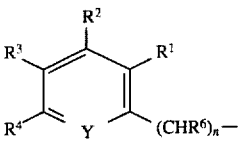 AcO— | 212 (Decomposition) 69 | 2.27(s, 3H), 5.24(s, 2H) 7.16(d, 2H, J=8.5Hz) 7.29(dd, 1H, J=8.9Hz, 2.3Hz) 7.48(d, 1H, J=2.1Hz) 7.57(d, 2H, J=8.5Hz) 7.64(dd, 1H, J=8.6Hz, 1.6Hz) 7.71(s, 1H), 7.91(m, 2H) 8.05(s, 1H) | 3439, 3036 1741, 1689 1593, 1271 1219, 1186 1016 |
| 43 | 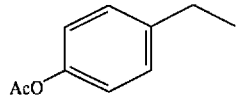 AcNH— | 200 (Decomposition) 62 | 2.03(s, 3H), 5.16(s, 2H) 7.28(d, 1H, J=10.0Hz) 7.42(d, 2H, J=8.3Hz) 7.48(s, 1H), 7.60(d, 2H, J=8.0Hz) 7.64(s, 1H), 7.83(s, 1H) 7.92(t, 2H, J=9.9Hz) 8.09(s, 1H), 9.99(s, 1H) | 3302, 3126 3034, 2775 1739, 1685 1589, 1523 1331, 1271 1184, 1001 |
| 44 | 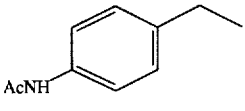 PhNHCO— | 249 (Decomposition) 91 | 5.35(s, 1H), 7.09(t, 1H, J=7.5Hz) 7.29–7.37(m, 3H), 7.46(s, 1H) 7.53(s, 1H), 7.60–7.70(m, 3H) 7.76(d, 2H, J=8.1Hz) 7.84(d, 1H, J=8.8Hz) 7.91(d, 1H, J=8.9Hz) 7.90–8.00(m, 3H) | 3306, 3055 1649, 1601 1545, 1442 1325, 1265 1178 |
| 45 | 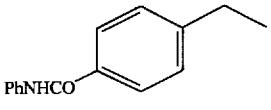 | 251 (Decomposition) 63 | 3.92–3.98(m, 2H) 3.99–4.05(m, 2H) 5.26(s, 2H), 5.73(s, 1H) 7.28(dd, 1H, J=9.0Hz, 2.4Hz) 7.44–7.48(m, 3H) 7.53(d, 2H, J=8.2Hz) 7.63(d, 2H, J=11.2Hz) 7.86(d, 1H, J=8.7Hz) 7.92(d, 1H, J=9.1Hz), 8.04(s, 1H) | 3433, 3140 3030, 2885 1739, 1687 1595, 1564 1394, 1305 1271, 1184 1082, 1018 |
| 46 | 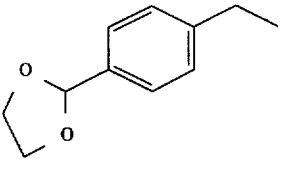 | 225~226 (Decomposition) 43 | 5.37(s, 2H) 7.29(dd, 1H, J=9.0Hz, 1.7Hz) 7.51(s, 1H), 7.60–7.70(m, 2H) 7.75(t, 1H, J=7.1Hz) 7.83(m, 3H), 7.95(t, 2H, J=9.1Hz) 8.11(s, 1H) | 3437, 3030 2779, 1739 1693, 1593 1315, 1271 1118, 1033 |
| 47 | 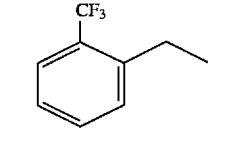 | 266~267 (Decomposition) 63 | 5.36(s, 2H) 7.33(d, 1H, J=9.5Hz) 7.50(s, 1H) 7.62–7.75(m, 4H) 7.82–7.92(m, 3H) 7.96(d, 1H, J=8.9Hz) 8.08(s, 1H) | 3427, 3117 3016, 2777 1743, 1691 1585, 1332 1273, 1203 1188, 1155 1114 |
| 48 | 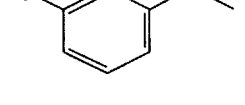 | 206 (Decomposition) 47 | 5.36(s, 2H) 7.30(d, 1H, J=8.4Hz) 7.45(s, 1H), 7.58–7.65(m, 2H) 7.75(d, 4H, J=3.8Hz) 7.85(d, 1H, J=9.0Hz) 7.92(d, 1H, J=9.1Hz), 8.02(s, 1H) | 3429, 3022 1691, 1608 1566, 1267 1213, 1172 1122, 1068 1018 |
| 49 | 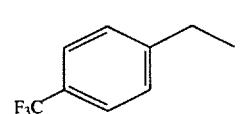 | 279~282 54 | 5.26(s, 2H) 7.18–7.29(m, 3H) 7.52–7.68(m, 3H) 7.90–7.99(m, 3H) 8.13(s, 1H) | 3135, 3034 1738, 1678 1591, 1470 1331, 1186 1152, 1055 |
| 50 | 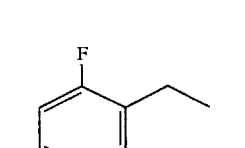 | 232~235 27 | 5.31(s, 2H) 7.25(dd, 1H, J=2.5Hz, 9.0Hz) 7.63–7.74(m, 5H), 7.91(s, 1H) 7.97(d, 1H, J=8.5Hz) 7.98(d, 1H, J=9.3Hz) 7.99(s, 1H), 12.61(s, 1H) | 3140, 3036 1736, 1692 1591, 1321 1188, 1171 1127, 1009 |

TABLE 6-continued

| Example No. | R² R³—⟨⟩—R¹ / R⁴ Y (CHR⁶)ₙ— | mp (°C.) Yield (%) | NMR (ppm) | IR (cm⁻¹) |
|---|---|---|---|---|
| 51 | F, F, F substituted phenyl-ethyl | 253~255 / 72 | 5.23(s, 2H), 7.24–7.35(m, 3H) 7.59(d, 1H, J=2.3Hz) 7.66(d, 1H, J=7.0Hz) 7.90–7.99(m, 2H), 8.16(s, 1H) 12.61(s, 1H) | 3154, 3057 1748, 1682 1624, 1591 1505, 1443 1325, 1269 |
| 52 | F, F, F, F, F substituted phenyl-ethyl | 239~240 / 39 | 5.35(s, 2H) 7.27(d, 1H, J=8.7Hz) 7.61(s, 1H) 7.67(d, 1H, J=8.8Hz) 7.87(s, 1H) 7.97(t, 2H, J=9.5Hz), 8.13(s, 1H) | 3443, 3155 3057, 1747 1703, 1664 1606, 1597 1471, 1392 1182, 1138 |
| 53 | naphthyl-methyl | 263 (Decomposition) / 83 | 5.33(s, 2H) 7.30–7.40(m, 2H) 7.49(s, 1H), 7.58(d, 1H, J=8.0Hz) 7.63(d, 1H, J=9.0Hz) 7.80–8.00(s, 4H) 8.11(s, 1H), 8.60(d, 1H, J=5.3Hz) | 3435, 2924 1709, 1601 1392, 1292 1267, 1188 1149, 1093 |
| 54 | pyridyl-ethyl | 166~167 (Decomposition) / 27 | 3.25(t, 2H, J=7.1Hz) 4.49(t, 2H, J=6.5Hz) 7.12(dd, 1H, J=2.3Hz, 9.2Hz) 7.24(t, 1H, J=6.1Hz) 7.37(d, 1H, J=2.0Hz) 7.40(d, 1H, J=7.9Hz) 7.50–7.70(m, 1H) 7.73(dt, 1H, J=1.7Hz, 9.4Hz) 7.83(d, 2H, J=8.7Hz), 7.95(s, 1H) 8.51(d, 1H, J=4.7Hz) | 3431, 2926 1697, 1566 1413, 1298 1261, 1155 1018 |
| 55 | phenyl-CH(Me) | 271 (Decomposition) / 61 | 1.60(d, 3H, J=5.0Hz) 5.68(g, 1H, J=6.5Hz) 7.19–7.26(m, 3H), 7.31(s, 1H) 7.35(t, 2H, J=3.4Hz) 7.47(d, 2H, J=7.0Hz) 7.56(d, 1H, J=8.6Hz) 7.68(d, 1H, J=8.75Hz) 7.80(d, 1H, J=9.7Hz), 7.90(s, 1H) | 3429, 3065 3032, 1666 1608, 1564 1413, 1307 1267, 1232 1187 |
| 56 | bis(4-chlorophenyl)-CH(Me) | 202 (Decomposition) / 13 | 6.80(s, 1H), 7.34(d, 2B, J=7.7Hz) 7.43(d, 4H, J=8.4Hz), 7.49(s, 1H) 7.54–7.60(m, 5H) 7.72(d, 1H, J=8.4Hz) 7.88(d, 1H, J=9.4Hz), 7.96(s, 1H) | 3369, 3173 3059, 1745 1689, 1676 1593, 1491 1178, 1012 |

Example 40

Synthesis of 5-[6-(4-formylbenzyloxy)-2-naphthyl]-methylene-thiazolidine-2,4-dione (compound No. 430 in Table 1)

5-{6-[4-(1,3-ethylenedioxy)-methylbenzyloxy]-2naphthyl}-methylene-thiazoline-2,4-dione (157 mg) obtained in Example 45 was suspended in acetone (90 ml) and then p-toluenesulfonic acid (10 mg) was added to the suspension. The resultant suspension was stirred at room temperature for 36 hours. After reaction, the acetone was distilled off. The resulting residue was recrystallized from hexane/ethyl acetate, washed with water and dried to obtain the title compound (80 mg, yield=57%). The spectral data and melting point are as follows.

¹H NMR (DMSO); 5.38 (s, 2H), 7.34 (d, 1H, J=9.0 Hz), 7.49 (s, 1H), 7.63 (d, 1 H, J=8.5 Hz), 7.72 (d, 2H, J=7.8 Hz), 7.8–8.0 (m, 5H), 10.01 (s, 1H)

IR (KBγ);

3126, 3026, 2779, 1738, 1697, 1595, 1396, 1273, 1186 cm⁻¹, m.p. ; 281° C. (decomposition)

Example 42

Synthesis of 5-[6-(3-aminobenzyloxy)-2-naphthyl]-methylene-thiazolidine-2,4-dione (compound No. 400 in Table 1)

5-[6-(3-nitrobenzyloxy)-2-naphthyl]-methylene-thiazoline-2,4-dione (300 mg) obtained in Example 34 was suspended in a mixture of methanol (50 ml) and methoxyethanol (75 ml) and then palladium on carbon (0.4 g) was added to the suspension under an inert atmosphere. After replacing the atmosphere with a hydrogen atmosphere, the resulting suspension was stirred overnight at room temperature at ordinary pressure.

After reaction, methanol (100 ml) was added, and the reaction mixture was vigorously stirred to dissolve the objective material, and filtered through celite. The solvent was distilled off. The resulting residue was recrystallized from ethyl acetate to obtain the title compound (130 mg, yield=49%). The spectral data and melting point are as follows.

$^1$H NMR (DMSO); 5.07 (s, 2H), 6.51 (d, 1H, J=8.5 Hz), 6.61 (d, 1H, J=7.8 Hz), 6.67 (s, 1H), 7.02 (t, 1H, J=7.8 Hz), 7.24 (dd, 1H, J=9.0, 2.3 Hz), 7.41 (s, 1H), 7.62 (d, 2H, J=6.5 Hz), 7.84 (d, 1H, J=8.5 Hz), 7.90 (d, 1H, J=9.0 Hz), 8.02 (s, 1H)

IR (KBγ);

3437, 3030, 1689, 1597, 1560, 1307, 1269, 1186, 1020 cm$^{-1}$, m.p.; 227°–229° C. (decomposition)

Example 57

Synthesis of 5-[6-(2-trifluoromethylbenzyloxy)-2naphthyl]-methylene-2-thioxy-thiazolidine-4-one (compound No. 703 in Table 2)

To a mixture of 6-(2-trifluoromethylbenzyloxy)-2-naphthylaldehyde (594 mg), rhodanine (266 mg) and sodium acetate (443 mg) was added acetic acid (2.3 ml). The mixture was heated to reflux for 2 hours and cooled gradually, and water (10 ml) was added thereto. The resulting mixture was sufficiently stirred and filtered. The resultant solid was recrystallized from ethanol, filtered and dried to obtain the title compound (543 mg, yield=68%). The spectral data and melting point are as follows.

$^1$H NMR (DMSO); 5.38 (s, 2H), 7.31 (dd, 1H, J=9.0 Hz, 2.5 Hz), 7.53 (d, 1H, J=2.2 Hz), 7.58–7.67 (m, 2H), 7.75 (m, 2H), 7.8–7.9 (m, 2H), 7.96 (d, 1H, J=8.7 Hz), 8.02 (d, 1H, J=91 Hz), 8.14 (s, 1H)

IR (KBγ);

3431, 3140, 3055, 2854, 1697, 1585, 1448, 1396, 1317, 1236, 1174, 1126 cm$^{-1}$, m.p.; 221°–224° C.

Preparation 11

Synthesis of 2-(6-benzyloxy)-naphthyl-methyl cyanide 2-(6-Benzyloxy)-naphthyl-methyl chloride (3.0 g) is dissolved in a mixture of DMF (30 ml) and EtOH (30 ml), and potassium cyanide (1.38 g) is added to the solution. The resulting mixture is stirred with heating under reflux for 48 hours. After reaction, the mixture is cooled to room temperature and toluene is added. The organic layer was washed with water and a saturated saline solution, dried over anhydrous magnesium sulfate, and concentrated in vacuo to obtain a residue. To the residue is added ethyl acetate (30 ml). The resulting crystals are washed under heating, cooled and then filtered to obtain the tile compound (2.25 g, yield=78%). The NMR spectrum is as follows.

NMR (CDCl$_3$) 3.88 (s, 2H), 5.19 (s, 2H), 7.22–7.42 (m, 7H), 7.48 (dt, 1H, J=1,5 Hz, 7.0 Hz), 7.73–7.7 6 (m, 3H)

Example 58

Synthesis of 5-(6-benzyloxy-2-naphthyl)-methyl-1-H-tetrazole (compound No. 720 in Table 3).

To a solution of 6-benzyloxy-2-naphthyl-methyl cyanide (0.40 g) in DMF (6 ml) were added sodium azide (0.48 g) and ammonium chloride (0.39 g). The mixture was stirred at 135° C. for 24 hours.

After reaction, the mixture is cooled to room temperature and ethyl acetate was added. The organic layer was washed, dried and concentrated in vacuo to obtain a residue. The resultant residue was subjected to column chromatography on silica gel eluting with chloroform/methanol to obtain an amorphous solid. It was recrystallized from ethyl acetate to obtain the tile compound (0.15 g, yield=32%). The spectral data and melting point are as follows.

NMR (DMSO d-6); 4.46 (s, 2H), 5.20 (s, 2H), 7.22 (dd, 1H, J=2.4 Hz, 9.0 Hz), 7.33–7.42 (m, 5H), 7.50 (d, 2H, J=6.8 Hz), 7.70 (s, 1H), 7.77 (t, 1H, J=7.9 Hz)

IR (KBγ);

3437, 3135, 3036, 2897, 2751, 1607, 1559, 1391, 1263, 1229, 1178 cm$^{-1}$ m.p.; 215°–217°

Example 59

Synthesis of 5-[6-(2-fluorobenzyloxy)-2-naphthyl]-methyl-thiazolidine-2,4-dione sodium salt (sodium salt of compound 5 in Table-1)

5-[6-(2-fluorobenzyloxy)-2-naphthyl]-methyl-thiazolidine-2,4-dione (3.81 g) obtained in Example 4 was suspended in methanol (100 ml) and sodium methoxide (28% methanol solution, 2.2 g) was added thereto. The mixture was stirred at room temperature for 1 hour.

After reaction, ethyl ether (40 ml) was added to the reaction mixture, so that the sodium salt was obtained as crystals. The crystals were washed with ethanol (40 ml) to obtain the title compound (3.70 g, yield=92%). The NMR, IR spectrum and melting point are as follows. NMR (DMSO d-6); 2.77 (dd, 1H, J=10.4 Hz, 13.7 Hz), 3.49 (dd, 1H, J=3.6 Hz, 13.6 Hz), 4.20 (dd, 1H, J=3.5 Hz, 10.6 Hz), 5.22 (S, 1H), 7.10–7.30 (m, 3H), 7.32 (t, 1H, J=6.3 Hz), 7.40–7.50 (m, 2H), 7.62 (t, 2H, J=7.3 Hz), 7.70 (d, 1H, J=8.5 Hz), 7.76 (d, 1H, J=9.0 Hz),

IR (KBγ);

3427, 3042, 1660, 1560, 1491, 1325, 1267, 1232, 1047 m.p.; >300° C. (decomposition)

Test examples

The effect of the compound of the present invention on reducing blood sugar and blood lipid levels based on the ability of improving insulin resistance has been determined by the following test.

KK-Ay male mice of five to six week age were obtained from Nihon CREA. The mice have been bred with a powder feed (MF powders for breeding rats and mice, Oriental Yeast Co.) from 7 days prior to the test. The mice of nine to eighteen week age having body weights of 35 g or more were used for the test.

The blood sugar values were measured by withdrawing blood (20 μl) from animal's tail vein using a heparin-treated capillary, centrifuging the blood to obtain plasma, and measuring the glucose level in the plasma by the glucose-oxidase method. The triglyceride (TG) levels in plasma were measured by the glycerol enzyme method. Five mice in a group having 200 mg/dl or more of the blood sugar level were used for one test.

The test compounds were mixed with powder food such that the average dosage of the former is 10–100 mg/kg/day, and the mixture was administered to the mice for four days. Blood was withdrawn from the animal's tail vein before administration, and five days after administration, and blood sugar and TG levels were measured using the methods mentioned above. The amount of the food ingested was measured every day during the test period, and the average of the amounts for four days was calculated.

The ability of reducing blood sugar level was determined as described below. Namely, the means of the blood sugar values at the time before administration of the test compound in a control group (a group to which the test compound was not administered) and an administration group (a group to which the test compound was administered) (such values are referred to as Mcon and Mad, respectively) and the means of the blood sugar values of the control group and the administration group on 5th day after administration (such values are referred to as Con and Ad, respectively) were determined. The blood sugar lowering effect found in the administration group was expressed by the following formula.

$$\text{Blood sugar lowering effect (\%)} = 1 - \frac{Ad/Mad}{Con/Mcon} \times 100$$

The blood TG lowering-ratio (%) was measured by the same procedure as that described above. All the values were statistically evaluated under significance level P=0.05.

The results are shown in Tables 7 and 8. The data of the known compounds CS-045 [the following formula (II)] and pioglitazone [the following formula (III)] are also listed in the tables.

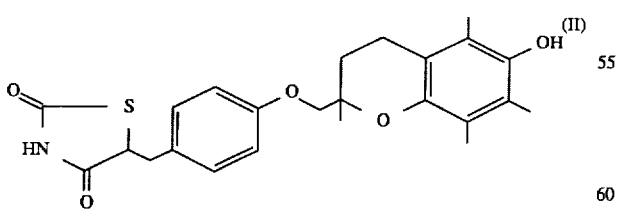

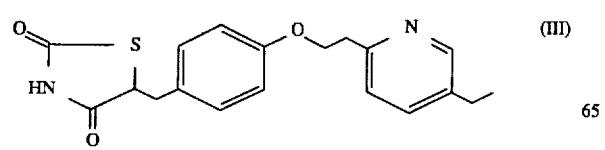

TABLE 7

| Compound (Example No.) | Dose: c.a. 10 mg/kg/day | |
|---|---|---|
| | Blood sugar lowering ratio (%) | TG lowering ratio (%) |
| 1 a) | 31.6** | 56.4 |
| 2 | 27.6** | 9.12* |
| 3 a) | 13.5 | 31.3 |
| 4 | 37.5** | 41.6* |
| 6 | 37.2*** | 37.7* |
| 7 | 33.7* | 28.3 |
| 8 | 10.9 | 9.4 |
| 10 | 56.2*** | 37.2 |
| Pioglitazone | 17.5* | −4.0 |
| CS-045 a) | 40.2** | −18.5 |

(*: p < 0.001, : <0.01, *: <0.05)
a): Dose c.a. 100 mg/kg/day

TABLE 8

| Compound (Example No.) | Dose: c.a. 50 mg/kg/day | |
|---|---|---|
| | Blood sugar lowering ratio (%) | TG lowering ratio (%) |
| 13 a) | 41.5** | 21.0 |
| 14 b) | 35.2** | 19.9 |
| 15 a) | 48.6*** | 38.8 |
| 16 a) | 37.2* | 22.3 |
| 17 a) | 35.9*** | 24.4 |
| 18 | 54.4*** | 53.8* |
| 19 | 34.4*** | 21.7 |
| 21 | 12.7 | 14.7 |
| 22 | 31.2* | 9.5 |
| 32 | 31.7* | 39.6* |
| 33 | 28.9 | 16.0 |
| 35 | 45.8*** | 56.9 |
| 39 | 17.1 | 16.0 |
| 46 | 48.1*** | 51.0** |
| 48 | 58.5*** | 25.6 |
| 49 a) | 39.6** | 43.4*** |
| 50 a) | 41.1* | 27.7** |
| 51 a) | 53.1*** | 46.1** |
| 52 | 45.9*** | 44.2 |
| 53 | 7.6 | 34.5* |
| 55 | 26.3 | 17.4 |

(*: P < 0.001, : <0.01, *: <0.05)
a): Dose c.a. 30 mg/kg/day
b): Dose c.a. 100 mg/kg/day As apparent from the above results, the compounds of the present invention are useful for reducing blood sugar and blood lipid levels in the dosage ranging from 10 to 100 mg/kg/day.

What is claimed is:

1. A naphthalene derivative of the formula:

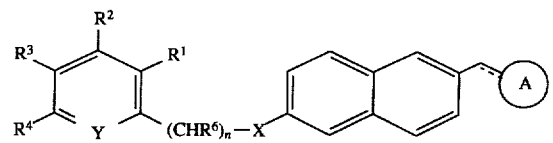

wherein the symbol

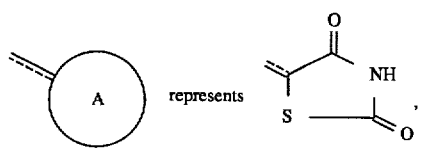

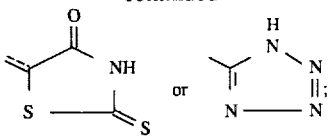

—X— represents —O— or —S—; =Y— represents =CR⁵—; each of $R^1$, $R^2$, $R^3$, $R^4$ and $R^5$ represents independently hydrogen, halogen, $C_1$–$C_8$ alkyl, $C_6$–$C_{12}$ aryl, $C_1$–$C_8$ alkoxy, $C_2$–$C_6$ alkoxyalkoxy, $C_6$–$C_{12}$ aryloxy, $C_2$–$C_9$ alkanoyloxy, $C_7$–$C_{13}$ arylcarbonyloxy, carboxy, $C_2$–$C_9$ alkoxycarbonyl, $C_7$–$C_{13}$ aryloxycarbonyl, carbamoyl, $C_2$–$C_9$ alkylaminocarbonyl, $C_7$–$C_{13}$ arylaminocarbonyl, amino, $C_1$–$C_8$ alkylamino, $C_2$–$C_9$ alkanoylamino, $C_7$–$C_{13}$ arylcarbonylamino, ethylenedioxymethyl, formyl, cyano, nitro or trihalomethyl; $R^6$ represents (1) hydrogen, (2) $C_1$–$C_8$ alkyl which is unsubstituted or is substituted by at least one substituent selected from the group consisting of phenyl, halogen, nitro and cyano, or (3) $C_6$–$C_{12}$ aryl which is unsubstituted or is substituted by at least one substituent selected from the group consisting of $C_1$–$C_8$ alkyl, halogen, nitro and cyano; n represents an integer of 0 to 3; and the dotted and solid lines show that the bond may be a single or double bond; or a pharmaceutically acceptable salt thereof.

2. A compound as claimed in claim 1 wherein each of $R^1$, $R^2$, $R^3$, $R^4$ and $R^5$ represents independently hydrogen, halogen, $C_1$–$C_8$ alkyl, $C_1$–$C_8$ alkoxy, $C_2$–$C_6$ alkoxyalkoxy, $C_2$–$C_9$ alkanoyloxy, $C_7$–$C_{13}$ arylcarbonyloxy, carboxy, $C_2$–$C_9$ alkoxycarbonyl, carbamoyl, $C_2$–$C_9$ alkylaminocarbonyl, $C_7$–$C_{13}$ arylaminocarbonyl, amino, $C_1$–$C_8$ alkylamino, $C_2$–$C_9$ alkanoylamino, $C_7$–$C_{13}$ arylcarbonylamino, ethylenedioxymethyl, formyl, cyano, nitro or trihalomethyl; $R^6$ represents hydrogen, $C_1$–$C_8$ alkyl, or $C_6$–$C_{12}$ aryl which may be substituted by halogen.

3. A compound as claimed in claim 1 wherein X represents —O—; each of $R^1$, $R^2$, $R^3$, $R^4$ and $R^5$ represents independently hydrogen, halogen, $C_1$–$C_5$ alkyl, $C_1$–$C_5$ alkoxy, $C_2$–$C_6$ alkoxyalkoxy, $C_2$–$C_6$ alkanoyloxy, carboxy, $C_2$–$C_6$ alkoxycarbonyl, $C_7$–$C_{13}$ arylaminocarbonyl, amino, $C_2$–$C_6$ alkanoylamino ethylenedioxymethyl, formyl, cyano, nitro or trihalomethyl; $R^6$ represents hydrogen, $C_1$–$C_5$ alkyl or $C_6$–$C_{12}$ aryl which may be substituted by halogen.

4. A compound as claimed in claim 1 characterized in wherein the symbol

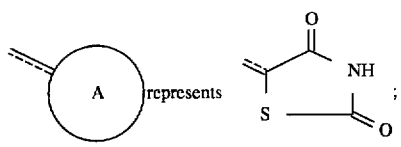

X represents —O—; each of $R^1$, $R^2$, $R^3$ and $R^4$ represents independently hydrogen or halogen; $R^5$ represents hydrogen; $R^6$ represents hydrogen; n represents 1; and the dotted and solid lines represent that the bond is a single bond.

5. A pharmaceutical composition for the treatment of diabetes which comprises an effective amount of a compound or salt thereof as defined in claim 1 and a pharmaceutically acceptable carrier therefor.

6. A method for the treatment of diabetes which comprises administering to a patient in need of such treatment an effective amount of a compound or salt thereof as defined in claim 1.

7. A compound as claimed in claim 1, said compound being 5-[6-(2-fluorobenzyloxy)-2-naphthyl]-methyl-thiazolidine-2,4-dione, or a pharmaceutically acceptable salt thereof.

* * * * *